United States Patent
Scott et al.

(10) Patent No.: US 12,194,084 B2
(45) Date of Patent: *Jan. 14, 2025

(54) MULTI-SUBUNIT VACCINES TO ELICIT BOTH MHC- AND CD1-RESTRICTED T CELL RESPONSES

(71) Applicant: Northwestern University, Evanston, IL (US)

(72) Inventors: Evan A. Scott, Northfield, IL (US); Chyung-Ru Wang, Evanston, IL (US); Shaobin Shang, Evanston, IL (US); Dina Kats, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/645,288

(22) Filed: Dec. 20, 2021

(65) Prior Publication Data
US 2022/0184197 A1    Jun. 16, 2022

Related U.S. Application Data

(63) Continuation of application No. 16/839,861, filed on Apr. 3, 2020, now Pat. No. 11,202,823.

(60) Provisional application No. 62/829,735, filed on Apr. 5, 2019.

(51) Int. Cl.
*A61K 39/04* (2006.01)
*A61K 9/51* (2006.01)
*A61K 39/00* (2006.01)

(52) U.S. Cl.
CPC .............. *A61K 39/04* (2013.01); *A61K 9/51* (2013.01); *A61K 2039/54* (2013.01); *A61K 2039/543* (2013.01); *A61K 2039/55588* (2013.01)

(58) Field of Classification Search
None
See application file for complete search history.

(56) References Cited

U.S. PATENT DOCUMENTS 11,202,823 B2   12/2021   Scott et al.
2018/0022878 A1   1/2018   Scott et al.

FOREIGN PATENT DOCUMENTS

WO          2001075096 A1    10/2001
WO   WO-2012093137 A1 *  7/2012    ............. A61K 31/06
WO   WO-2018217564 A1 * 11/2018   ............. A61K 39/04

OTHER PUBLICATIONS

Dowling et al. J Allergy Clin Immunol, Nov. 2017, pp. 1339-1350.*
Frey et al. Nanomedicine (2018) 13 (14), 1795-1811.*
Anderson et al. J Immunol (2009) 183 (4):2294-2302.*
Shang et al. J Allergy Clin Immunol, Nov. 2017, pp. 1339-1350.*
Velluto et al. Molecular Pharmaceutics 2008 5 (4), 632-642.*
Amselem et al. Polymers for Advanced Technologies, vol. 3, pp. 351-357, 1992.*
Dudala et al. Int J Pharm Investig. Oct.-Dec. 2014; 4(4):149-155.*
Siddiqui S, et al. Role of Group 1 CD1-Restricted T Cells in Infectious Disease. Front Immunol. 2015;6:337.
Sieling PA, Chatterjee D, Porcelli SA, Prigozy TI, Mazzaccaro RJ, Soriano T, et al. CD1-restricted T cell recognition of microbial lipoglycan antigens. Science (New York, NY. 1995;269(5221):227-30.
Silva JM, et al. Immune system targeting by biodegradable nanoparticles for cancer vaccines. J Control Release. 2013; 168(2):179-99.
Stack T, et al. Modulation of Schlemm's canal endothelial cell stiffness via latrunculin loaded block copolymer micelles. J Biomed Mater Res A. 2018;106(7):1771-9.
Stano A, et al.Tunable T cell immunity towards a protein antigen using polymersomes vs. solid-core nanoparticles. Biomaterials. 2013;34(17):4339-46.
Sugita M, et al. Pathways of CD1 and lipid antigen delivery, trafficking, processing, loading, and presentation. Curr Top Microbiol Immunol. 2007;314:143-64.
Tameris M et al. A double-blind, randomised, placebo-controlled, dose-finding trial of the novel tuberculosis vaccine AERAS-402, an adenovirus-vectored fusion protein, in healthy, BCG-vaccinated infants. Vaccine. 2015;33(25):2944-54.
Tameris M et al. Lessons learnt from the first efficacy trial of a new infant tuberculosis vaccine since BCG. Tuberculosis. 2013;93(2):143-9.
Tameris MD, et al. Safety and efficacy of MVA85A, a new tuberculosis vaccine, in infants previously vaccinated with BCG: a randomised, placebo-controlled phase 2b trial. Lancet. 2013;381(9871):1021-8.
Terabe M, et al. Tissue-Specific Roles of NKT Cells in Tumor Immunity. Front Immunol. 2018;9:1838.
Toyohara M, et al. Studies on the effect of isoniazid upon the antituberculous immunity induced by BCG vaccination. Tubercle. 1959;40:184-91.
U.S. Pharmacopeia National Formulary, 1857-1859, (1990).
Van Rhijn I et al. CD1a, CD1b, and CD1c in immunity against mycobacteria. Advances in experimental medicine and biology. 2013;783:181-97.
Van Rhijn I, et al. CD1 and mycobacterial lipids activate human T cells. Immunological reviews. 2015;264(1):138-53.
Van Rhijn I, et al. CD1b-mycolic acid tetramers demonstrate T-cell fine specificity for mycobacterial lipid tails. European journal of immunology. 2017;47(9):1525-34.
Van Rhijn I, et al. Human autoreactive T cells recognize CD1b and phospholipids. Proceedings of the National Academy of Sciences of the United States of America. 2016;113(2):380-5.

(Continued)

*Primary Examiner* — Oluwatosin A Ogunbiyi
(74) *Attorney, Agent, or Firm* — Quarles & Brady LLP

(57) ABSTRACT

Provided herein are subunit vaccine compositions comprising a nanocarrier and a lipid antigen, a peptide antigen or combinations thereof that elicit bother a CD1-restricted and an MHC-restricted T cell response in a subject. Methods for making and using the subunit vaccine compositions are also provided.

13 Claims, 31 Drawing Sheets
(21 of 31 Drawing Sheet(s) Filed in Color)
Specification includes a Sequence Listing.

(56) References Cited

OTHER PUBLICATIONS

Van Rhijn I, et al. The bovine CD1 family contains group 1 CD1 proteins, but No. functional CD1d. Journal of Immunology. 2006;176(8):4888-93.
Vasdekis AE, et al. Precision intracellular delivery based on optofluidic polymersome rupture. ACS nano. 2012;6(9):7850-7.
Viader-Salvadó J.M. G-Om, Garza-González E. Tijerina-Menchaca R. Drug Susceptibility of *Mycobacterium tuberculosis* Through the Mycolic Acid Index. . Gillespie SH (eds) Antibiotic Resistence Methods in Molecular Medicine ™: Humana Press; 2001, 7 pages.
Vincent MS, et al. CD1a-, b-, and c-restricted TCRs recognize both self and foreign antigens. Journal of Immunology. 2005;175(10):6344-51.
Wendorf J, et al. A practical approach to the use of nanoparticles for vaccine delivery. Journal of pharmaceutical sciences. 2006;95(12):2738-50.
Wolf AJ, et al. Initiation of the adaptive immune response to *Mycobacterium tuberculosis* depends on antigen production in the local lymph node, not the lungs. The Journal of experimental medicine. 2008;205(1):105-15.
Wolf BJ, et al. Novel Approaches to Exploiting Invariant NKT Cells in Cancer Immunotherapy. Front Immunol. 2018;9:384.
Yi S, et al. Tailoring Nanostructure Morphology for Enhanced Targeting of Dendritic Cells in Atherosclerosis. ACS Nano. 2016;10(12):11290-303.
Yi, S., et al. "Surface engineered polymersomes for enhanced modulation of dendritic cells during cardiovascular Immunotherapy." Advanced Functional Materials 29.42 (2019): 1904399.
Yoshida M et al. Poly(lactic-co-glycolic acid) enhances maturation of human monocyte-derived dendritic cells. J Biomed Mater Res A. 2004;71(1):45-54.
Yoshida M, et al. Effect of poly(lactic-co-glycolic acid) contact on maturation of murine bone marrow-derived dendritic cells. J Biomed Mater Res A. 2007;80(1):7-12.
Zajonc "The CD1 family: serving lipid antigens to T cells since the Mesozoic era," Immunogenetics, 2016, 68(8):561-576.
Zhao J, et al. Mycolic acid-specific T cells protect against *Mycobacterium tuberculosis* infection in a humanized transgenic mouse model. Elife. 2015;4.
Frey M, et al. Influences of nanocarrier morphology on therapeutic immunomodulation. Nanomedicine, 2018, 13(14):1795-1811.
Gilleron M, et al. Diacylated sulfoglycolipids are novel mycobacterial antigens stimulating CD1-restricted T cells during infection with *Mycobacterium tuberculosis*. The Journal of experimental medicine. 2004;199(5):649-59.
Gold MC, et al. Human mucosal associated invariant T cells detect bacterially infected cells. PLoS Biol. 2010;8(6):e1000407.
Gong J, et al. Isolation of mycobacterium-reactive CD1-restricted T cells from patients with human immunodeficiency virus infection. The Journal of clinical investigation. 1998;101(2):383-9.
Goren MB, et al. Lipids of putative relevance to virulence in *Mycobacterium tuberculosis*: correlation of virulence with elaboration of sulfatides and strongly acidic lipids. Infect Immun. 1974;9(1):142-9.
Goter-Robinson C, et al. Protection against an aerogenic *Mycobacterium tuberculosis* infection in BCG-immunized and DNA-vaccinated mice is associated with early type I cytokine responses. Vaccine. 2006;24(17):3522-9.
Han J, et al. A simple confined impingement jets mixer for flash nanoprecipitation. J Pharm Sci. 2012;101(10):4018-23.
Hava DL, et al. Evasion of peptide, but not lipid antigen presentation, through pathogen-induced dendritic cell maturation. Proc Natl Acad Sci U S A. 2008;105(32):11281-6.
Hiromatsu K, et al. Induction of CD1-restricted immune responses in guinea pigs by immunization with mycobacterial lipid antigens. J Immunol. 2002;169(1):330-9.
International Searching Authority. International Search Report and Written Opinion for application PCT/US2020/026649. Mailed on Jul. 17, 2020.

James CA, et al. CD1b Tetramers Identify T Cells that Recognize Natural and Synthetic Diacylated Sulfoglycolipids from *Mycobacterium tuberculosis*. Cell Chem Biol. 2018;25(4):392-402 e14.
Jelley-Gibbs DM, et al. Unexpected prolonged presentation of influenza antigens promotes CD4 T cell memory generation. J Exp Med. 2005;202(5):697-706.
Kallert S, et al. Liposomal delivery of lipoarabinomannan triggers *Mycobacterium tuberculosis* specific T-cells. Tuberculosis. 2015;95(4):452-62.
Karabin NB, et al. Sustained micellar delivery via inducible transitions in nanostructure morphology. Nat Commun. 2018;9(1):624.
Kasmar AG, et al. CD1b tetramers bind alphabeta T cell receptors to identify a mycobacterial glycolipid-reactive T cell repertoire in humans. The Journal of experimental medicine. 2011;208(9):1741-7.
Kaufmann SH, et al. Novel approaches to tuberculosis vaccine development. Int J Infect Dis. 2017;56:263-7.
Kawasaki N, et al. Targeted delivery of mycobacterial antigens to human dendritic cells via Siglec-7 induces robust T cell activation. J Immunol. 2014;193(4):1560-6.
Larrouy-Maumus G, et al. Protective efficacy of a lipid antigen vaccine in a guinea pig model of tuberculosis. Vaccine. 2017;35(10):1395-402.
Layton ED, et al. Validation of a CD1b tetramer assay for studies of human mycobacterial infection or vaccination. J Immunol Methods. 2018;458:44-52.
Lemmer Y, et al. Mycolic acids, a promising mycobacterial ligand for targeting of nanoencapsulated drugs in tuberculosis. J Control Release. 2015;211:94-104.
Lepore M, et al. Targeting leukemia by CD1c-restricted T cells specific for a novel lipid antigen. Oncoimmunology. 2015;4(3):e970463.
Lis, et al. Autoreactive CD1b-restricted T cells: a new innate-like T-cell population that contributes to immunity against Infection. Blood. 2011;118(14):3870-8.
Lindenstrom T, et al. Tuberculosis subunit vaccination provides long-term protective immunity characterized by multifunctional CD4 memory T cells. J Immunol. 2009;182(12):8047-55.
Ly D, et al. CD1c tetramers detect ex vivo T cell responses to processed phosphomycoketide antigens. The Journal of experimental medicine. 2013;210(4):729-41.
Manjaly Thomas ZR, et al. Aerosol immunisation for TB: matching route of vaccination to route of infection. Transactions of the Royal Society of Tropical Medicine and Hygiene. 2015;109(3):175-81.
Matsunaga I, et al. Mycolyltransferase-mediated glycolipid exchange in Mycobacteria. J Biol Chem. 2008;283(43):28835-41.
Montamat-Sicotte DJ, et al. A mycolic acid-specific CD1-restricted T cell population contributes to acute and memory immune responses in human tuberculosis infection. J Clin Invest. 2011;121(6):2493-503.
Moody DB, et al. CD1c-mediated T-cell recognition of isoprenoid glycolipids in *Mycobacterium tuberculosis* infection. Nature. 2000;404(6780):884-8.
Moody DB, et al. Structural requirements for glycolipid antigen recognition by CD1b-restricted T cells. Science. 1997;278(5336):283-6.
Napoli A, et al. Glucose-oxidase based self-destructing polymeric vesicles. Langmuir. 2004;20(9):3487-91.
Napoli A, et al. Oxidation-responsive polymeric vesicles. Nature Materials. 2004;3:183.
Nikitczuk KP, et al. PLGA-polymer encapsulating tumor antigen and CpG DNA administered into the tumor microenvironment elicits a systemic antigen-specific IFN-gamma response and enhances survival. J Cancer Ther. 2013;4(1):280-90.
Olsen AW, et al. The influence of remaining live BCG organisms in vaccinated mice on the maintenance of immunity to tuberculosis. Scand J Immunol. 2004;60(3):273-7.
Onaca O, et al. Stimuli-responsive polymersomes as nanocarriers for drug and gene delivery. Macromol Biosci. 2009;9(2):129-39.
Ott I, et al. Sulfur-substituted naphthalimides as photoactivatable anticancer agents: DNA interaction, fluorescence imaging, and phototoxic effects in cultured tumor cells. Bioorg Med Chem. 2008;16(15):7107-16.

(56) References Cited

OTHER PUBLICATIONS

Pais VF, et al. OFF-ON-OFF fluorescence switch with T-latch function. Org Lett. 2011;13(20):5572-5.
Panyam J, et al. Rapid endo-lysosomal escape of poly(DL-lactide-co-glycolide) nanoparticles: implications for drug and gene delivery. FASEB J. 2002;16(10):1217-26.
Perdomo C, et al. Mucosal BCG Vaccination Induces Protective Lung-Resident Memory T Cell Populations against Tuberculosis. Mbio. 2016;7(6), 11 pages.
Prasad S, et al. Tolerogenic Ag-PLG nanoparticles induce tregs to suppress activated diabetogenic CD4 and CD8 T cells. J Autoimmun. 2018;89:112-24.
Rodrigues LC, et al. Protective effect of BCG against tuberculous meningitis and miliary tuberculosis: a meta-analysis. Int J Epidemiol. 1993;22(6):1154-8.
Rosenkrands I, et al. Cationic liposomes containing mycobacterial lipids: a new powerful Th1 adjuvant system. Infect Immun. 2005;73(9):5817-26.
Saito G, et al. Synthesis of 1,8-naphthalimide-based probes with fluorescent switch triggered by flufenamic acid. R Soc Open Sci. 2018;5(6):172137.
Sakai S, et al. Defining features of protective CD4 T cell responses to *Mycobacterium tuberculosis*. Curr Opin Immunol. 2014;29:137-42.
Salio M, et al. Biology of CD1- and MR1-restricted T cells. Annual review of immunology. 2014;32:323-66.
Salio M, et al. Modulation of human natural killer T cell ligands on TLR-mediated antigen-presenting cell activation. Proc Natl Acad Sci U S A. 2007;104(51):20490-5.
Schaible UE, et al. Apoptosis facilitates antigen presentation to T lymphocytes through MHC-I and CD1 in tuberculosis. Nature medicine. 2003;9(8):1039-46.
Schiefner et al. "Presentation of lipid antigens by CD1 glycoproteins," Curr Pharm Des. 2009, 15(28):3311-3317.
Scott EA, et al. Dendritic cell activation and T cell priming with adjuvant- and antigen-loaded oxidation-sensitive polymersomes. Biomaterials. 2012;33(26):6211-9.
Scott EA, et al. Overcoming Immune Dysregulation with Immunoengineered Nanobiomaterials. Annu Rev Biomed Eng. 2017;19:57-84.
Shang, S, et al. "Induction of mycobacterium tuberculosis lipid-specific T cell responses by pulmonary delivery of mycolic acid-loaded polymeric micellar Nanocarriers." Frontiers in immunology 9 (2018): 2709.
Shann F. Different Strains of Bacillus Calmette-Guerin Vaccine Have Very Different Effects on Tuberculosis and on Unrelated Infections. Clin Infect Dis. 2015;61(6):960-2.
Aagaard C, et al. Protection and polyfunctional T cells induced by Ag85B-TB10.4/IC31 against *Mycobacterium tuberculosis* is highly dependent on the antigen dose. PloS one. 2009;4(6):e5930.
Achkar JM, et al. B cells and antibodies in the defense against *Mycobacterium tuberculosis* infection. Immunol Rev. 2015;264(1):167-81.
Aguilo N, et al. Pulmonary but Not Subcutaneous Delivery of BCG Vaccine Confers Protection to Tuberculosis- Susceptible Mice by an Interleukin 17-Dependent Mechanism. J Infect Dis. 2016;213(5):831-9.
Allahyari M, et al. Peptide/protein vaccine delivery system based on PLGA particles. Hum Vaccin Immunother. 2016;12(3):806-28.
Allen RP, et al. Latent, Immunosuppressive Nature of Poly(lactic-co-glycolic acid) Microparticles. ACS Biomaterials Science & Engineering. 2018;4(3):900-18.
Allen SD et al. Benchmarking Bicontinuous Nanospheres against Polymersomes for in Vivo Biodistribution and Dual Intracellular Delivery of Lipophilic and Water-Soluble Payloads. ACS Applied Materials & Interfaces. 2018;10 (40):33857-66.
Allen SD et al. Engineering nanomaterials to address cell-mediated inflammation in atherosclerosis. Regen Eng Transl Med. 2016;2(1):37-50.
Allen SD et al. Facile assembly and loading of theranostic polymersomes via multi-impingement flash hanoprecipitation. J Control Release. 2017;262:91-103.
Allen SD et al. On the advancement of polymeric bicontinuous nanospheres toward biomedical applications. Nanoscale Horizons. 2019, 18 pages.
Allen SD et al. Polymersomes scalably fabricated via flash nanoprecipitation are non-toxic in non-human primates and associate with leukocytes in the spleen and kidney following intravenous administration. Nano Research. 2018., 15 pages.
Andersen, C. A. S. et al. "Novel generation mycobacterial adjuvant based on liposome-encapsulated monomycoloyl glycerol from *Mycobacterium bovis* bacillus Calmette-Guerin." The Journal of Immunology 183.4 (2009): 2294-2302.
Bagchi S, et al. CD1b-autoreactive T cells contribute to hyperlipidemia-induced skin inflammation in mice. The Journal of clinical investigation. 2017;127(6):2339-52.
Bagchi S, et al. CD1b-autoreactive T cells recognize phospholipid antigens and contribute to antitumor immunity against a CD1b(+) T cell lymphoma. Oncoimmunology. 2016;5(9):e1213932.
Ballester M, et al. Nanoparticle conjugation and pulmonary delivery enhance the protective efficacy of Ag85B and CpG against tuberculosis. Vaccine. 2011;29(40): 6959-66.
Barral DC, et al. CD1 antigen presentation: how it works. Nature reviews. 2007;7(12):929-41.
Barry CE, 3rd, et al. Mycolic acids: structure, biosynthesis and physiological functions. Prog Lipid Res. 1998;37(2-3):143-79.
Beckman EM, et al. Recognition of a lipid antigen by CD1-restricted alpha beta+ T cells. Nature. 1994;372(6507):691-4.
Beckman EM, et al. CD1c restricts responses of mycobacteria-specific T cells. Evidence for antigen presentation by a second member of the human CD1 family. J Immunol. 1996;157(7):2795-803.
Berge, S. M. et al. Pharmaceutical salts. (1977) J. Pharm. Sci. 66:1-19).
Betts RJ, et al. Contact sensitizers trigger human CD1-autoreactive T-cell responses. Eur J Immunol. 2017;47(7):1171-80.
Beveridge NE, et al. Immunisation with BCG and recombinant MVA85A induces long-lasting, polyfunctional *Mycobacterium tuberculosis*-specific CD4+ memory T lymphocyte populations. Eur J Immunol. 2007;37(11):3089-3100.
Billeskov R, et al. High Antigen Dose Is Detrimental to Post-Exposure Vaccine Protection against Tuberculosis. Front Immunol. 2017;8:1973.
Blaauboer SM, et al. The mucosal adjuvant cyclic di-GMP enhances antigen uptake and selectively activates binocytosis-efficient cells in vivo. Elife. 2015;4, 25 pages.
Bobbala S, et al. Flash nanoprecipitation permits versatile assembly and loading of polymeric bicontinuous cubic hanospheres. Nanoscale. 2018;10(11):5078-88.
Bobbala S, et al. Novel Injectable Pentablock Copolymer Based Thermoresponsive Hydrogels for Sustained Release Vaccines. AAPS J. 2016; 18(1):261-9.
Bobbala S, et al. Poloxamer 407-chitosan grafted thermoresponsive hydrogels achieve synchronous and sustained release of antigen and adjuvant from single-shot vaccines. Immunology & Cell Biology. 2018;96(6):656-65.
Byrne ML, et al. Self-reported parenting style is associated with children's inflammation and immune activation. J Fam Psychol. 2017;31(3):374-80.
Cabral H, et al. Progress of drug-loaded polymeric micelles into clinical studies. J Control Release. 2014;190:465-76.
Cerritelli S, et al. Aggregation behavior of poly(ethylene glycol-bl-propylene sulfide) di- and triblock copolymers in aqueous solution. Langmuir. 2009;25(19):11328-35.
Cerritelli S, et al. Thermodynamic and kinetic effects in the aggregation behavior of a poly(ethylene glycol-b-propylene sulfide-b-ethylene glycol) ABA triblock copolymer. Macromolecules. 2005;38(18):7845-51.
Chancellor A, et al. CD1b-restricted GEM T cell responses are modulated by *Mycobacterium tuberculosis* mycolic acid meromycolate chains. Proceedings of the National Academy of Sciences of the United States of America. 2017;114(51):E10956-E64.

(56) References Cited

OTHER PUBLICATIONS

Chancellor A, et al. The versatility of the CD1 lipid antigen presentation pathway. Immunology. 2018;154(2):196-203.

Christian DA, et al. Polymersome carriers: from self-assembly to siRNA and protein therapeutics. Eur J Pharm Biopharm. 2009;71(3):463-74.

Consonni M, et al. Potential advantages of CD1-restricted T cell immunotherapy in cancer. Mol Immunol. 2018;103:200-8.

Dascher CC, et al. Immunization with a mycobacterial lipid vaccine improves pulmonary pathology in the guinea pig model of tuberculosis. International immunology. 2003;15(8):915-25.

Davenne T, et al. Why don't we have an effective tuberculosis vaccine yet? Expert Rev Vaccines. 2016;15(8):1009-13.

Davidsen J, et al. Characterization of cationic liposomes based on dimethyldioctadecylammonium and synthetic cord factor from *M. tuberculosis* (trehalose 6,6'-dibehenate)-a novel adjuvant inducing both strong CMI and antibody responses. Biochimica et biophysica acta. 2005;1718(1-2):22-31.

De Jong A, et al. CD1a-autoreactive T cells are a normal component of the human alphabeta T cell repertoire. Nat Immunol. 2010;11(12):1102-9.

De Jong A. Activation of human T cells by CD1 and self-lipids. Immunol Rev. 2015;267(1):16-29.

De Lalla C, et al. High-frequency and adaptive-like dynamics of human CD1 self-reactive T cells. Eur J Immunol. 2011;41(3):602-10.

De Libero G, et al. The T-Cell Response to Lipid Antigens of *Mycobacterium tuberculosis*. Front Immunol. 2014;5:219.

Discher BM, et al. Polymersomes: tough vesicles made from diblock copolymers. Science. 1999;284(5417):1143-6.

Dowling DJ, et al. Toll-like receptor 8 agonist nanoparticles mimic immunomodulating effects of the live BCG vaccine and enhance neonatal innate and adaptive immune responses. J Allergy Clin Immunol. 2017;140(5):1339-50.

Du F, et al. Sequential intracellular release of water-soluble cargos from Shell-crosslinked polymersomes. J Control Release. 2018, 25 pages.

Du FF, et al. Immunotheranostic Polymersomes Modularly Assembled from Tetrablock and Diblock Copolymers with Oxidation-Responsive Fluorescence. Cell Mol Bioeng. 2017;10(5):357-70.

Duffy D, et al. Immunological memory transferred with CD4 T cells specific for tuberculosis antigens Ag85B-TB10.4: persisting antigen enhances protection. PLoS One. 2009;4(12):e8272.

Espinosa-Cueto P, et al. Dendritic cells that phagocytose apoptotic macrophages loaded with mycobacterial antigens activate CD8 T cells via cross-presentation. PLoS One. 2017;12(8):e0182126.

Felio K, et al. CD1-restricted adaptive immune responses to Mycobacteria in human group 1 CD1 transgenic mice. The Journal of experimental medicine. 2009;206(11):2497-509.

Garcia MdLA, et al. Protective effect of a lipid-based preparation from *Mycobacterium smegmatis* in a murine model of progressive pulmonary tuberculosis. BioMed research international. 2014;2014:273129.

Gilleron M, et al. Acylation state of the phosphatidylinositol hexamannosides from *Mycobacterium bovis* bacillus Calmette Guerin and *Mycobacterium tuberculosis* H37Rv and its implication in Toll-like receptor response. The Journal of biological chemistry. 2003;278(32):29880-9.

* cited by examiner

FIGS. 5A-5D
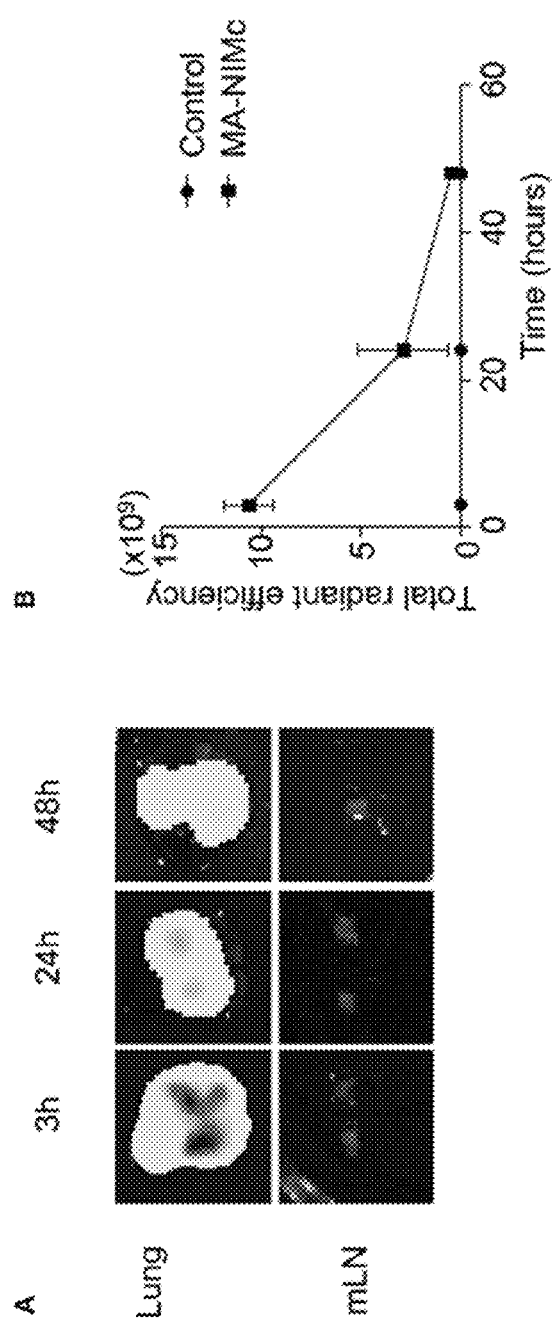
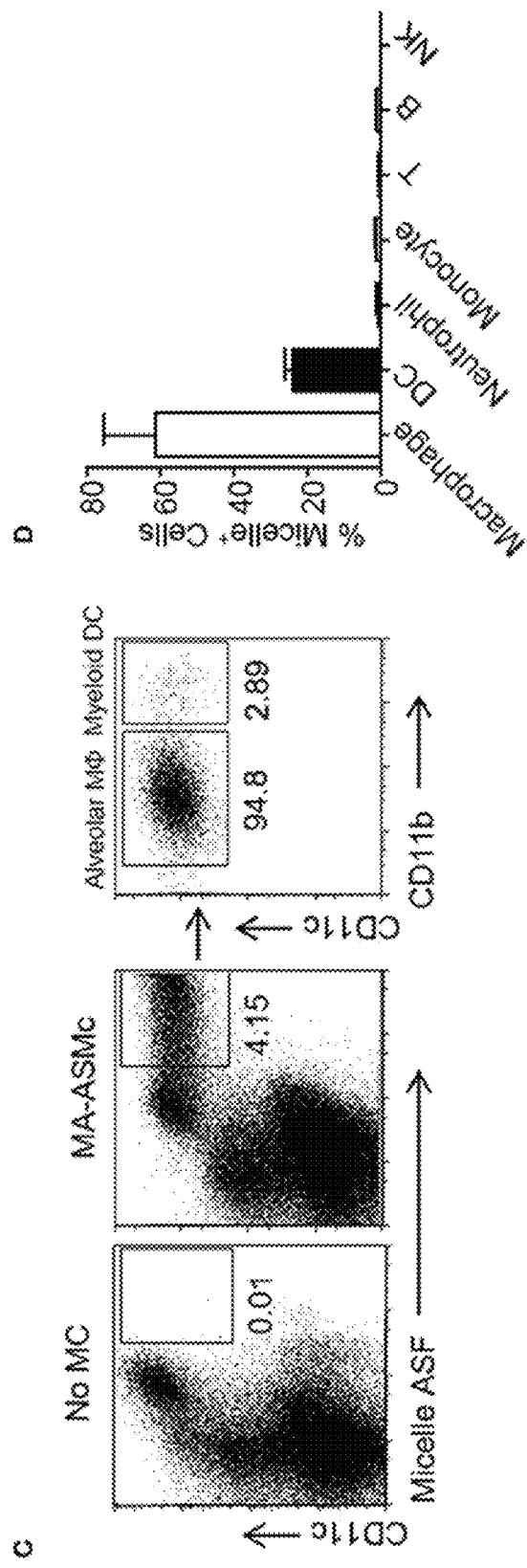

FIGS. 18A-18E
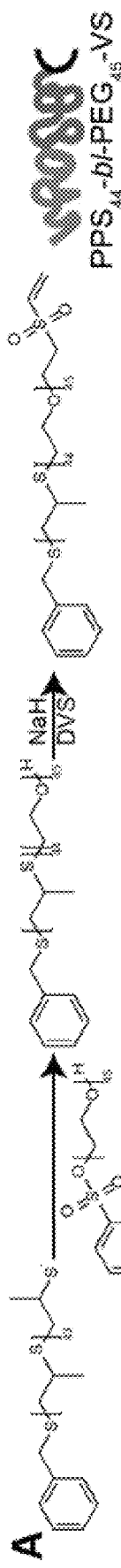
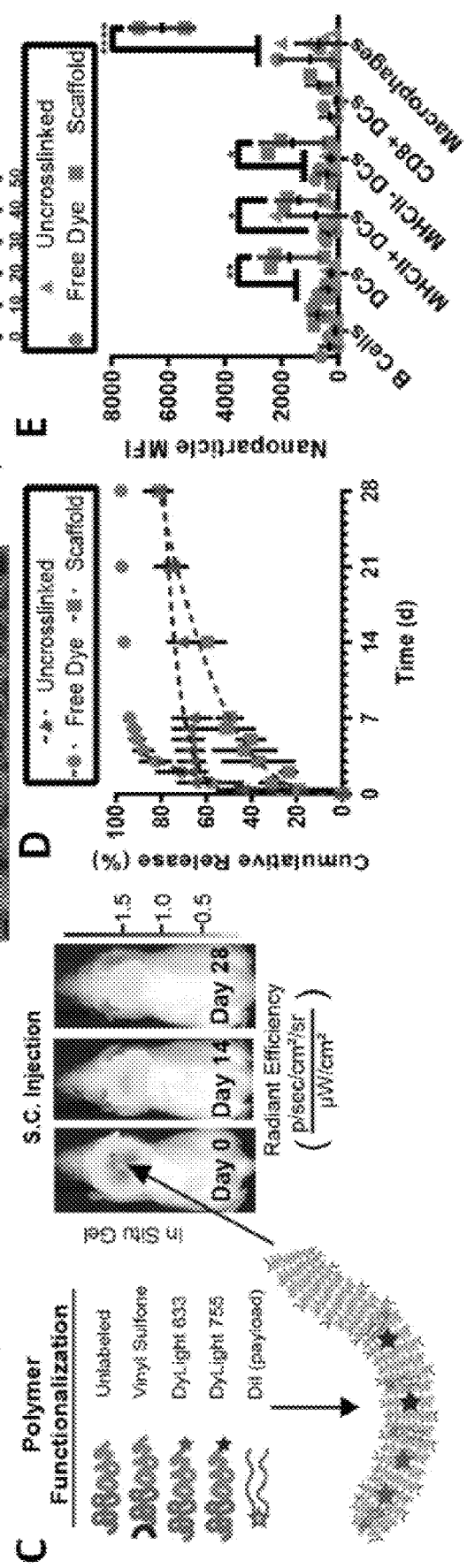

SEQUENCE LISTING

```
<160> NUMBER OF SEQ ID NOS: 1

<210> SEQ ID NO 1
<211> LENGTH: 8
<212> TYPE: PRT
<213> ORGANISM: Mus musculus

<400> SEQUENCE: 1

Ser Ile Ile Asn Phe Glu Lys Leu
1               5
```

MULTI-SUBUNIT VACCINES TO ELICIT BOTH MHC- AND CD1-RESTRICTED T CELL RESPONSES

CROSS-REFERENCE TO RELATED APPLICATIONS

This application is a continuation of U.S. application Ser. No. 16/839,861, filed Apr. 3, 2020, now U.S. Pat. No. 11,202,823, which claims priority to U.S. Provisional Application No. 62/829,735, filed Apr. 5, 2019, each of which are incorporated herein by reference in their entireties.

STATEMENT REGARDING FEDERALLY SPONSORED RESEARCH

This invention was made with government support under grant numbers HL132390, AI131035, AI057460 awarded by the National Institutes of Health and grant number 1453576 awarded by the National Science Foundation. The government has certain rights in the invention.

REFERENCE TO A SEQUENCE LISTING SUBMITTED VIA EFS-WEB

The content of the ASCII text file of the sequence listing named "702581_01747_ST25.txt" which is 0.52 kb in size was created on Apr. 3, 2020 and electronically submitted via EFS-Web herewith the application is incorporated herein by reference in its entirety.

BACKGROUND

Tuberculosis (TB), the disease caused by *Mycobacterium tuberculosis* (Mtb), remains one of the world's deadliest communicable diseases (1). The waxy cell wall of Mtb contains several unique lipids which are highly distinct from mammalian lipids and influence mycobacterial viability, making them attractive targets for immune defense. Indeed, several of lipids derived from the mycobacterial cell wall can be recognized by CD1-restricted T cells (2-7).

The CD1 family of antigen presenting molecules is specialized in presenting lipid/glycolipid antigens to T cells (6, 8). Humans express group 1 CD1 molecules CD1a, CD1b, and CD1c, and the group 2 molecule, CD1d. Mice, however, only express CD1d (8). Among four CD1 isoforms, CD1b presents the largest pool of Mtb-derived lipids, including mycolic acid (MA), the key structural element of Mtb's outer membrane (8, 9). MA broadly distributed within endosomal compartments of dendritic cells MA-specific CD1b-restricted T cells can be detected in the blood (2) and disease sites of tuberculosis patients and demonstrated a memory response upon ex vivo re-stimulation (10). These MA-specific CD1b-restricted T cells are cytotoxic and produce proinflammatory cytokines IFN-γ and TNF-α, crucial to anti-Mtb immunity (2, 11, 12). In addition, adoptive transfer of MA-specific CD1b-restricted T cells confers protection to Mtb infection in a human group 1 CD1 transgenic (hCD1Tg) mouse model (13, 14). These data suggest that MA may be harnessed as components of novel vaccines against Mtb infection.

SUMMARY OF THE INVENTION

In a first aspect, provided herein is a subunit vaccine composition comprising a nanocarrier and a lipid antigen. In some embodiments, the vaccine composition additionally comprises a peptide antigen. In some embodiments, the lipid antigen is a bacterial lipid antigen, and the peptide antigen is a bacterial peptide antigen. In some embodiments, the lipid antigen is a CD1b-presented lipid antigen. In some embodiments, the lipid antigen is selected from the group consisting of mycolic acid (MA), dieoxymycobactin, mannosyl phosphomycoketide, *Mycobacterium tuberculosis* (Mtb) total lipid extract (Tlip), sulfoglycolipid (SGL), phosphatidyl mannoside 2 (PIM2), phosphotidyl mannoside 6 (PIM6), lipoarabinomannan (LAM), trehalose dimycolate (TDM), glucose monomycolate (GMM). In some embodiments, the peptide antigen is specific to Mtb. In some embodiments, the peptide antigen is selected from the group consisting of *Mycobacterium Tuberculosis* major secretory protein antigen 85A (Ag85A), Antigen 85B (Ag85B), Mtb early secretory antigenic target 6 (ESAT-6), and Low Molecular Weight Protein Antigen 7 EsxH (Protein TB10.4).

In some embodiments, the nanocarrier comprises poly (ethylene glycol)-bl-poly(propylene sulfide) (PEG-bl-PPS). In some embodiments, the nanocarrier is selected from the group consisting of a micelle, a filomicelle, a polymersome, and a bicontinuous nanosphere. In some embodiments, the nanocarrier is a bicontinuous nanosphere. In some embodiments, the nanocarrier is a filomicelle. In some embodiments, the filomicelle comprises vinyl sulfone modified PEG-bl-PPS (VS-PEG-bl-PPS). In some embodiments, the filomicelle is crosslinked to form a hydrogel. In some embodiments, the VS-PEG-bl-PPS is crosslinked with thiol modified poly(ethylene glycol).

In a second aspect, provided herein is a hydrogel depot comprising a multi-subunit vaccine described herein.

In a third aspect, provided herein is a composition comprising a subunit vaccine of as described herein and a pharmaceutically acceptable carrier.

In a fourth aspect, provided herein is a composition comprising a hydrogel as described herein and a pharmaceutically acceptable carrier.

In some embodiments, any of the the compositions described herein may additionally comprise an adjuvant.

In a fifth aspect, provided herein is a method of eliciting an immune response comprising administering a subunit vaccine as described herein to a subject in an effective amount to elicit an immune response. In some embodiments, the subunit vaccine is administered by subcutaneous, intradermal, or intramuscular injection. In some embodiments, the subunit vaccine is administered intranasally.

BRIEF DESCRIPTION OF DRAWINGS

The patent or patent application file contains at least one drawing in color. Copies of this patent or patent application publication with color drawings will be provided by the Office upon request and payment of the necessary fee.

(FIG. 1A) The structure of mycolic acid (MA) loaded PEG-PPS-ASF micelles (MA-ASMc) is represented as a cartoon. Load of MA results in protonation of the fluorophore to decrease fluorescence. (FIG. 1B) Representative images of MA-ASMc nanocarriers visualized by cryogenic transmission electron microscopy. (FIG. 1C) Dynamic light scattering measurements of MA-ASMc hydrodynamic diameter. Error bars represent standard deviation (SD), n=6. (FIG. 1D) Micelles were made with different loadings of MA and fluorescence was measured. Micelles at all concentration of MA>6.25 µg MA/10 mg PEG-PPS-ASF (1:558 molar ratio) showed a 30% decrease in fluorescence. ***, P<0.001.

(FIG. 2A) Live BMDCs were imaged by confocal microscopy at different time points after pulsing with 1 mg/ml of either MA-ASMc or vehicle micelles (V-ASMc) for 4 hours. Lysosomes were stained with Lysotracker (red); Micelles appear in green. Magnification is 100×. Arrows indicate points of co-localization (yellow). (FIG. 2B) The fluorescence intensity of cells incubated with either MA-ASMc or V-ASMc was measured at time points of 4 h, 8 h and 24 h. The ratio of cell fluorescence (MA-ASMc/V-ASMc) significantly increased and remained stable after 4 h, suggesting release of MA from nanocarriers between 4 h and 8 h. ***, P<0.001.

(FIG. 3A) Representative dot-plot of activated DN1 cells expressing CD69 and CD25 responding to MA-ASMc stimulation. (FIG. 3B) The percentage of CD25$^+$CD69$^+$ DN1 T cells activated by BMDCs pulsed with MA-ASMc for different length of times. (FIG. 3C) The number of IFN-γ-producing DN1 T cells activated by BMDCs pulsed with MA-ASMc for different length of time.

(FIG. 4A) The percentage of CD25$^+$CD69$^+$NN1 T cells activated by different concentrations of MA-ASMc, free MA and V-ASMc; (n=4) (FIG. 4B) The concentration of IFN-γ produced by DN1 T cells in response to stimulation of different concentrations of MA-ASMc, free MA and V-ASMc; (n=4). (FIGS. 4C and 4D) CBA cytokine analysis of DN1 stimulated for 48 h with hCD1Tg MHC II deficient BMDC pulsed with (FIG. 4C) MA-ASMc or V-ASMc or (FIG. 4D) pulsed with MA-ASMc and treated with CD1b Ab or isotype control; (n=4). *, P<0.05; , P<0.01; *, P<0.001; ****, P<0.0001.

FIGS. 5A-5D show MA-Mc are mainly retained in the lung after pulmonary delivery and taken up by alveolar macrophages and myeloid DCs. The in vivo bio-distribution of Dylight 750 conjugated (NIMc) or ASF-labeled micelles (ASMc) in different organs was visualized by In Vivo imaging system (IVIS) (FIGS. 5A and 5B) and tracked by flow cytometry (FIGS. 5C and 5D) after pulmonary administration. (FIG. 5A) and (FIG. 5B) The kinetics (FIG. 5A) and intensity (FIG. 5B) of MA-NIMc in the lung and mediastinal lymph nodes (mLN) were visualized by IVIS from 3 to 48 h after i.n. delivery. (FIG. 5C) MA-ASMc-carrying cells in the lungs of unimmunized vs immunized mice were examined by flow cytometry. (FIG. 5D) The percentage of different leukocyte subsets carrying MA-ASMc in the lung of mice (n=3) 24 h after pulmonary delivery. Data are representative from three repeat experiments.

(FIG. 6A) Schematic diagram of experimental design. (FIG. 6B) Representative dot plots and percentage of DN1 T cells in the MLN of recipient mice unimmunized (n=3) or immunized with MA-ASMc via intratracheal (I.T., n=4), intranasal (I.N., n=3) and subcutaneous (S.C., n=4) route. (FIG. 6C) Representative dot plot of DN1 T cells from MLNs of V-ASMc (n=5) vs MA-ASMc-immunized (n=6) hCD1Tg mice. (FIG. 6D) Proliferation and (FIG. 6E) activation of DN1 T cells were compared in V-ASMc (n=3) vs MA-ASMc-immunized (n=4) hCD1Tg mice by flow cytometry. Data are representative of three experiments. (FIG. 6F) Percent expression of CD44/CD62 and (FIG. 6G) representative histogram of CCR7 and CD103 expression (black line) on DN1 T cells in the lung (n=4). Grey solid areas indicate isotype controls. (FIG. 6H) Representative intracellular cytokine staining of IFN-γ, TNF-α, and IL-2 in DN1 T cells from the spleen after phorbol 12-myristate 13-acetate (PMA) and ionomycin (INO) stimulation (n=4). , P<0.01; *, P<0.001.

(FIG. 9A) The fluorophore has an absorbance maximum at 395 nm and an emission maximum at 505 nm. (FIG. 9B) Fluorescence of empty (V-ASMc) or MA-loaded acid sensitive fluorophore tagged micelles (MA-ASMc) was measured at different pH values. Fluorescence drops after pH 3. All error bars represent SD, n=3.

(FIG. 12A) The comparison of bio-distribution of MA-NIMc delivered by intranasal vs intravenous route 3 h after delivery in different organs; (FIG. 12B) The kinetic bio-distribution of MA-NIMC from 3 to 48 hours after i.n. delivery in different organs.

(FIG. 17D) TEM images of PS and BCN with or without 2 wt % ethyl eosin loaded. Arrows identify example nanoparticles. Scale bar=200 nm. (FIG. 17E) SAXS data with labeled Bragg peaks for BCN formed via three separate methods demonstrate a cubic mesophase. (FIG. 17F) DLS number distribution of PS and BCN diameters. (FIG. 17G) BCN display oxidation-triggered release of payloads at relevant intracellular concentrations of reactive oxygen species. (FIG. 17H) Fold increase of pyrene fluorescence at 390 nm upon excitation at 331 nm in 1×PBS or in the presence of pre-formed BCN or PS. (FIG. 17I) NP number per μg of polymer for PS and BCN. (FIG. 17J) Loading efficiency of FITC-BSA and DiD in PS and BCN when dual loaded. *p<0.001, ***p<0.0001. N=3. (K) Activation of DC following a 14 h incubation with BCN loaded with TLR4 agonist MPLA and protein antigen ovalbumin (Ova). Surface expression of MHC/peptide (SIINFEKL; SEQ ID NO:1) complexes was quantified using a fluorescent antibody.

FIGS. 18A-18E show filamentous hydrogel depot (FM-depot) for sustained controlled delivery of nanocarrier vaccines. (FIG. 18A) Synthesis of vinyl sulfone (VS) functionalized PEG-b-PPS to allow crosslinking of self-assembled filomicelles (FM). FM-depots bud micellar (MC) drug loaded delivery vehicles or encapsulated nanocarriers. (FIG. 18B), Cartoon representations and cryogenic TEM micrographs of various stages of FM-depot fabrication and sustained MC delivery. (FIG. 18C) Modular assembly of FMs from 4 separate block copolymers for in situ crosslinking into FM-depots and multimodal analysis following s.c. injection in mice. (FIG. 18D) Cumulative release curves and power law model fits of released MC (Dylight 755) was quantified by NIRF imaging. (FIG. 18E) Flow cytometric analysis of MC (Dylight 633) uptake by APC. *p<0.05, p<0.01, **p<0.0001.

(FIG. 19A) DN1 T cells were co-cultured with unpulsed or MA-pulsed WT or hCD1Tg DC. IFN-γ-producing cells were determined by ELISPOT assay. (FIG. 19B) BMDC were infected with Mtb (MOI=5) and DN1 T cells were added 1 day after infection. After 48 h, activation markers on DN1 T cells were determined by FACS.

(FIG. 21A). CryoTEM image and overlaid DLS size distribution of PLGA-NP formed by double emulsion (W/O/W) method (Scale bar=200 nm). (FIG. 21B) Encapsulation efficiency (percentage of cargo successfully loaded relative to total initial cargo) of FITC-BSA and DiD in PLGA-NP and BCN when simultaneously loaded, error bars represent SD, N=3, statistical significance tested using Holm-Sidak multiple t-test (****p<0.0001). (FIG. 21C) Confocal images of RAW 264.7 macrophages stained with lysosomal dye Lysotracker (green) and NucBlue stain (blue) following incubation with Texas Red labeled PLGA-NP and BCN (red) for 8 h. White arrows in the merged image point to examples of colocalization of lysotracker and Texas Red signals, demonstrating endolysosomal uptake of BCNs and yellow arrows in the top row indicate the cytosolic release of Texas red from PLGA-NP (Scale bar=10 μm). (FIG. 21D) DC from hCD1Tg were pulsed with free MA, unloaded BCN (BCN-Blank), MA-loaded BCN (BCN-MA), unloaded PLGA-NP (PLGA-Blank) or MA-loaded PLGA-NP (PLGA-MA) then co-cultured with DN1 T cells for 24 h. Activation markers CD25 and CD69 on DN1 T cells was detected by flow cytometry. N=3.

Lymphocytes from MLN of Mtb-infected mice were stimulated with Tg+ DC in the presence of indicated Mtb lipid. Fold changes were calculated as # of IFN-g secreting cells to Ag-pulsed DC/# of IFN-g secreting cells to unpulsed DC. Data are representative of 3 experiments where n=3. (Tlip: Total lipid extract, MA: Mycolic acid, SGL: Sulfoglycolipid, PIM2, PIM6: Phosphatidyl mannosides 2, 6, LAM: Lipoarabinomannan, TDM: Trehalose Dimycolate, GMM: Glucose monomycolate).

Figure 24:
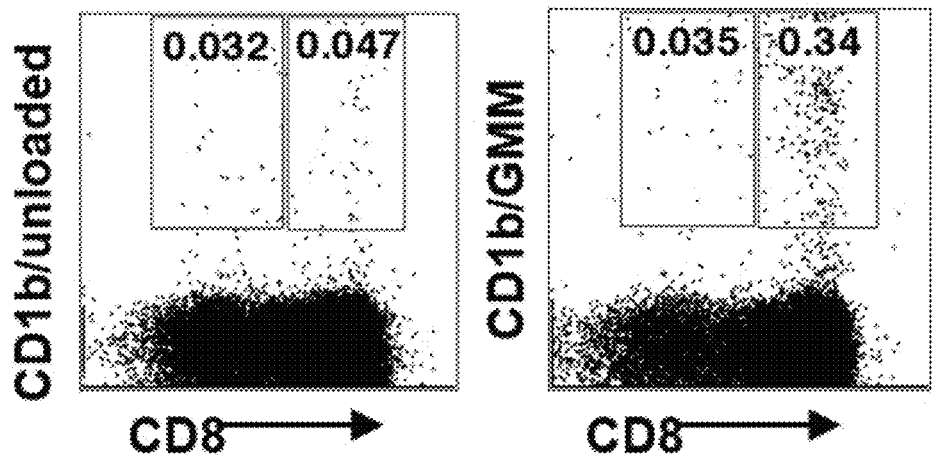

FIG. 24 shows staining of GMM-specific T cells with CD1b/GMM tetramers. MLN from Mtb-infected hCD1Tg mice were stained with CD1b/GMM tetramer or CD1b/unloaded tetramer along with anti-CD8 (N=3).

Figures 25A, 25B:
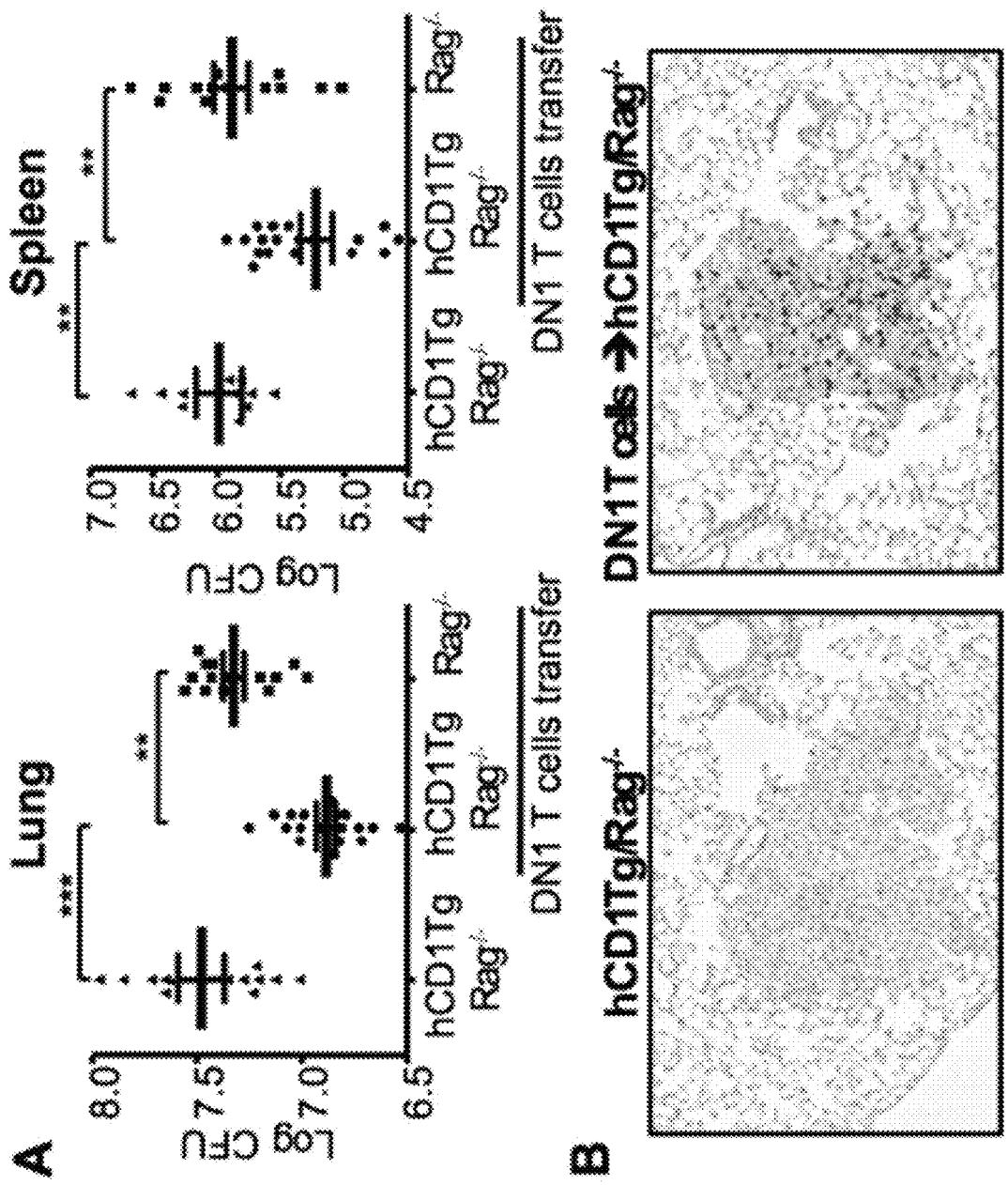

FIGS. 25A-25B show adoptive transfer of DN1 T cells confers protection against Mtb. DN1 T cells were transferred into hCD1Tg/Rag$^{-/-}$ and Rag$^{-/-}$ mice 1 day before infection. (FIG. 25A) Bacterial CFU in the lung and spleen were determined at 4 wks. post-infection. (FIG. 25B) Immunohistochemistry showed that DN1 T cells (detected by anti-CD3, brown cells) accumulated in lung granulomas.

FIGS. 26A-26D show DN1 T cells are activated earlier than Ag85 specific CD4+ T cells after Mtb infection. (FIGS. 26A, 26B) CFSE-labeled DN1 T cells and CellTrace Violet-labeled P25 T cells were co-transferred into Mtb infected CD45.1 congenic hCD1Tg mice. CD69 expression, CFSE and CellTrace Violet were detected on DN1 T cells and P25 T cells from MLN at indicated time points. (FIGS. 26C, 26D) Bar graphs depict the mean and SEM of the percentages of CD69$^{hi}$ and CFSE/Violet low populations among DN1 and P25 T cells. Results are representative of 2 experiments (N=4).

Figure 27:
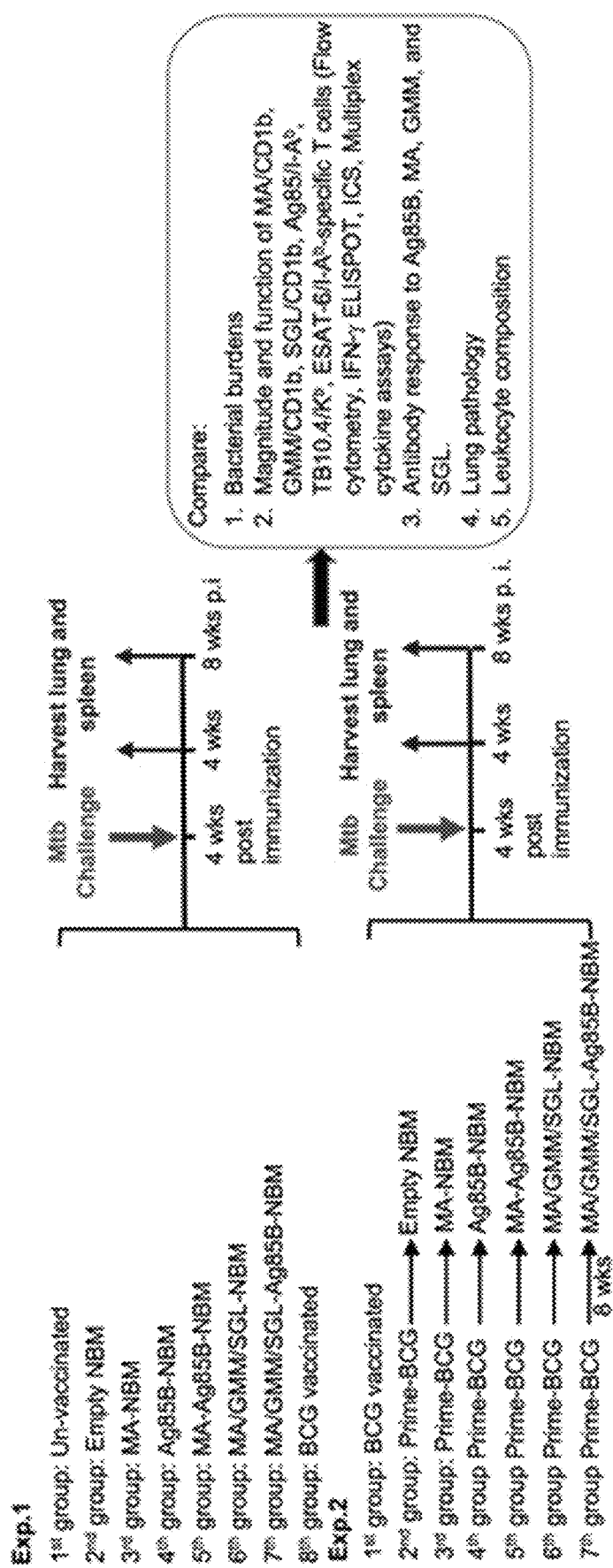

FIG. 27 shows a schematic for in vivo evaluation of subunit vaccination against virulent Mtb infection when eliciting a combined CD1- and MHC-restricted T cell response.

Figures 28A, 28B, 28C:
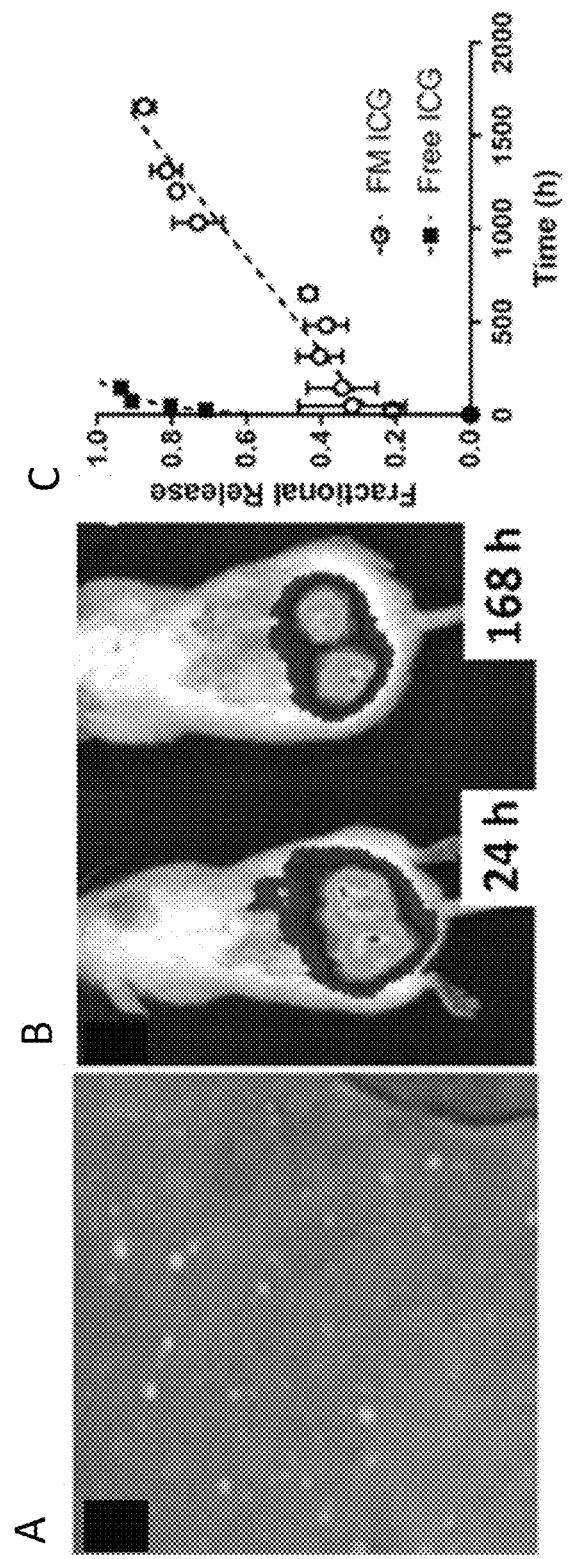

FIGS. 28A-28C show FM-depots can controllably deliver NBM for over 10 weeks. (FIG. 28A) FM-depots can stably entrap NBM containing payloads. Green=calcein loaded within PS, blue=hydrophobic fluorophore ethyl eosin loaded within filomicelles (FMs). (FIG. 28B) FMs were loaded with the NIRF imaging agent ICG and injected s.c. into mice. (FIG. 28C) Release of ICG-loaded MCs from FM-depots was monitored for 10 weeks and compared to free form ICG.

Figures 29A, 29B:
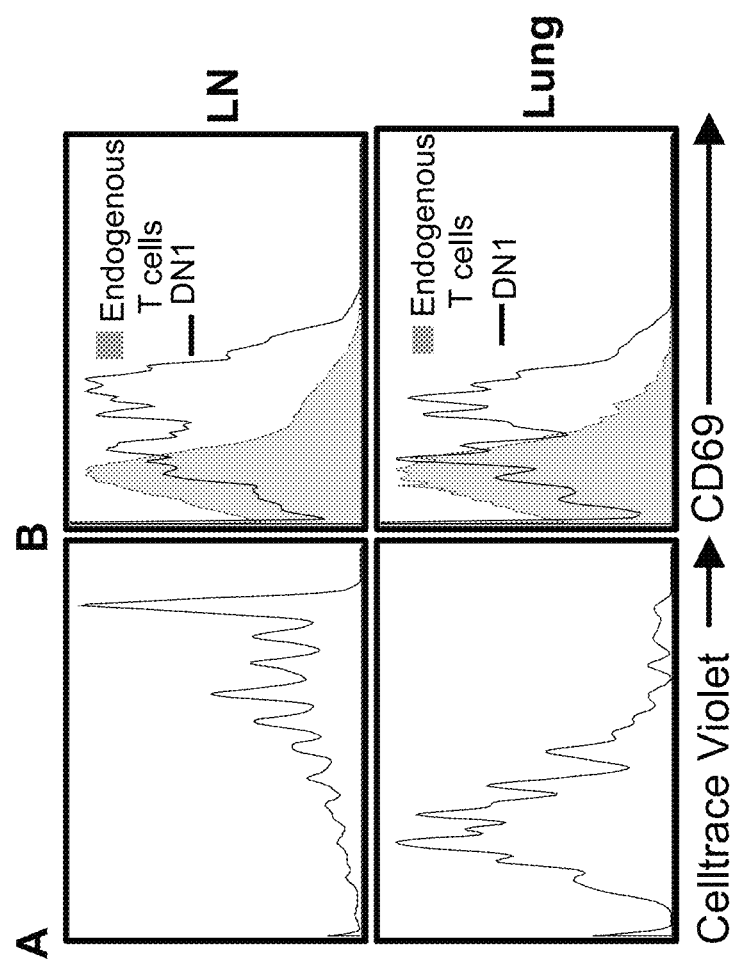

FIGS. 29A-29B show MA-loaded FM-depot activates DN1 T cells in vivo. hCD1Tg mice were immunized with MA-hydrogel one week prior to the adoptive transfer of Celltrace violet-labeled DN1 T cells. 6 days later, DN1 T cell proliferation (A) and CD69 expression (B) in the LN and lung were determined by FACS (N=3). The expression of CD69 on endogenous T cells was used as control (gray areas).

Figures 30A, 30B, 30C:
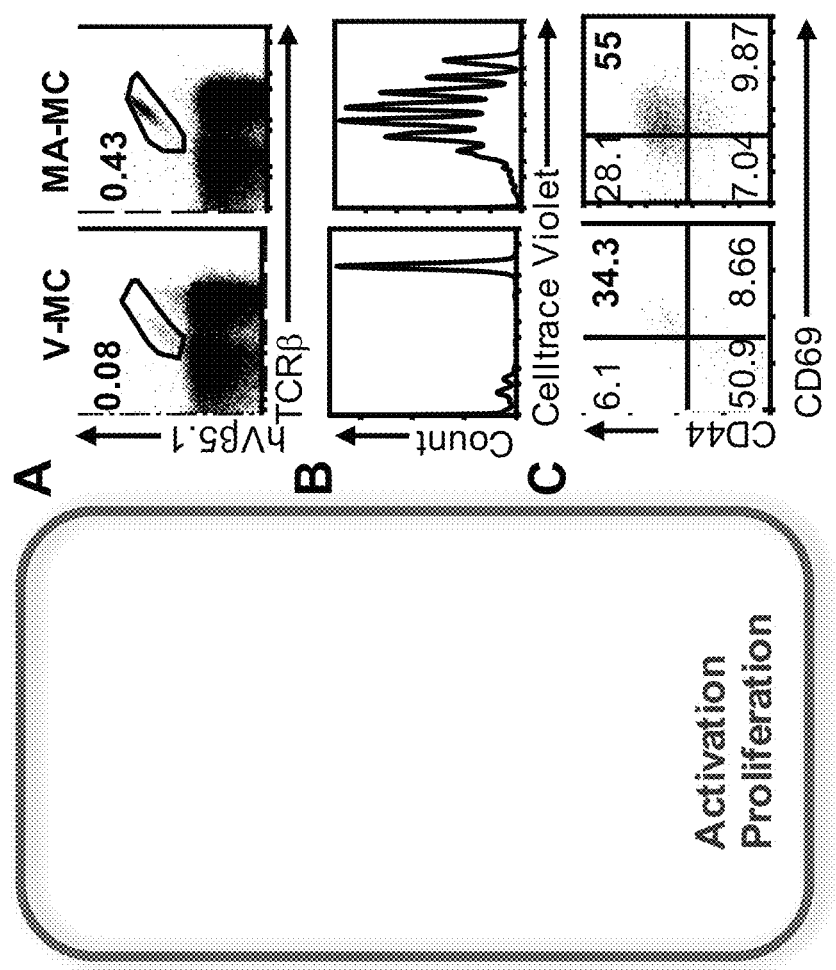

FIGS. 30A-30C show MA-MC induce proliferation and activation of adoptively-transferred MA-specific DN1 T cells. Celltrace violet-labeled DN1T cells were adoptively transferred into hCD1Tg mice 1 day before i.n. immunization with MA-MC (n=3) or micelle vehicle (V-MC) (n=2). Six days later, DN1 T cells from V-MC-vs MA-MC-immunized hCD1Tg mice were analyzed by FACS. (FIG. 30A) Representative dot plot of DN1 T cells in MLN of indicated mice. (FIG. 30B) Proliferation and (FIG. 30C) Expression of activation markers on DN1 T cells were compared by flow cytometry. Data are representative from three experiments.

Figure 31:
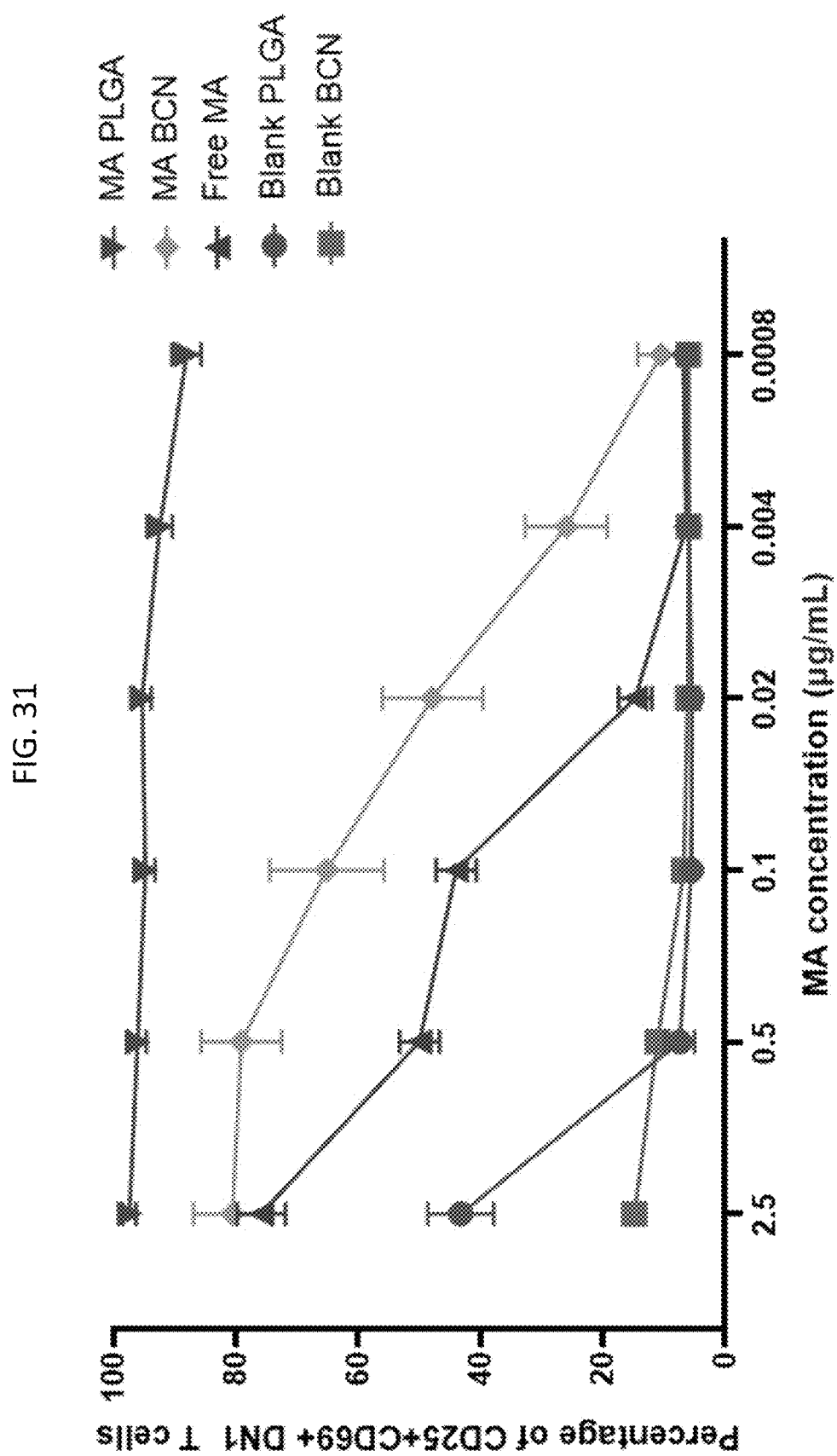

FIG. 31 shows bmDCs were pulsed for 18 h with selected nanoparticles, co-cultured for 48 h with DN1 T cells. CD69 and CD25 receptor surface expression was assessed by flow cytometry, and the percentage of CD69+CD25+ DN1 T cells is shown. N=3 per condition.

Figures 32A, 32B:
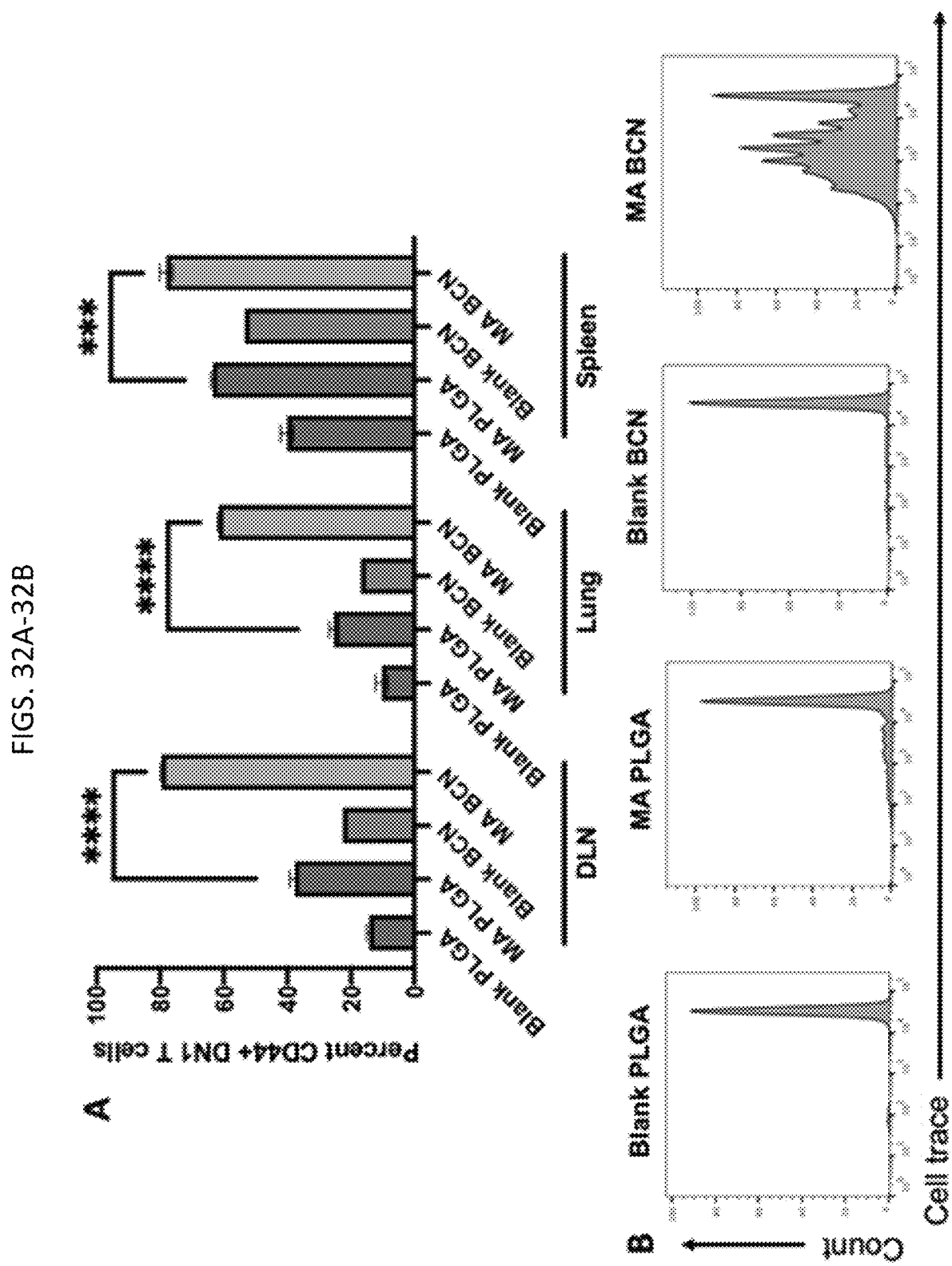

FIGS. 32A-32B show hCD1Tg mice were intranasally vaccinated with nanoparticles on day 1, and 3E6 DN1 T cells were stained with cell trace and adoptively transferred on day 2. At day 7, DN1 T cell activation was measured with CD44 marker. (A) Percentage of CD44+ DN1 T cells in selected organs. (B) Distribution of cell trace dye in DN1 T cells from draining lymph nodes (DLN). MA PLGA N=2, MA BCN N=2, blank BCN N=1, PLGA N=2, ****p<0.0001.

Figures 33A, 33B, 33C:
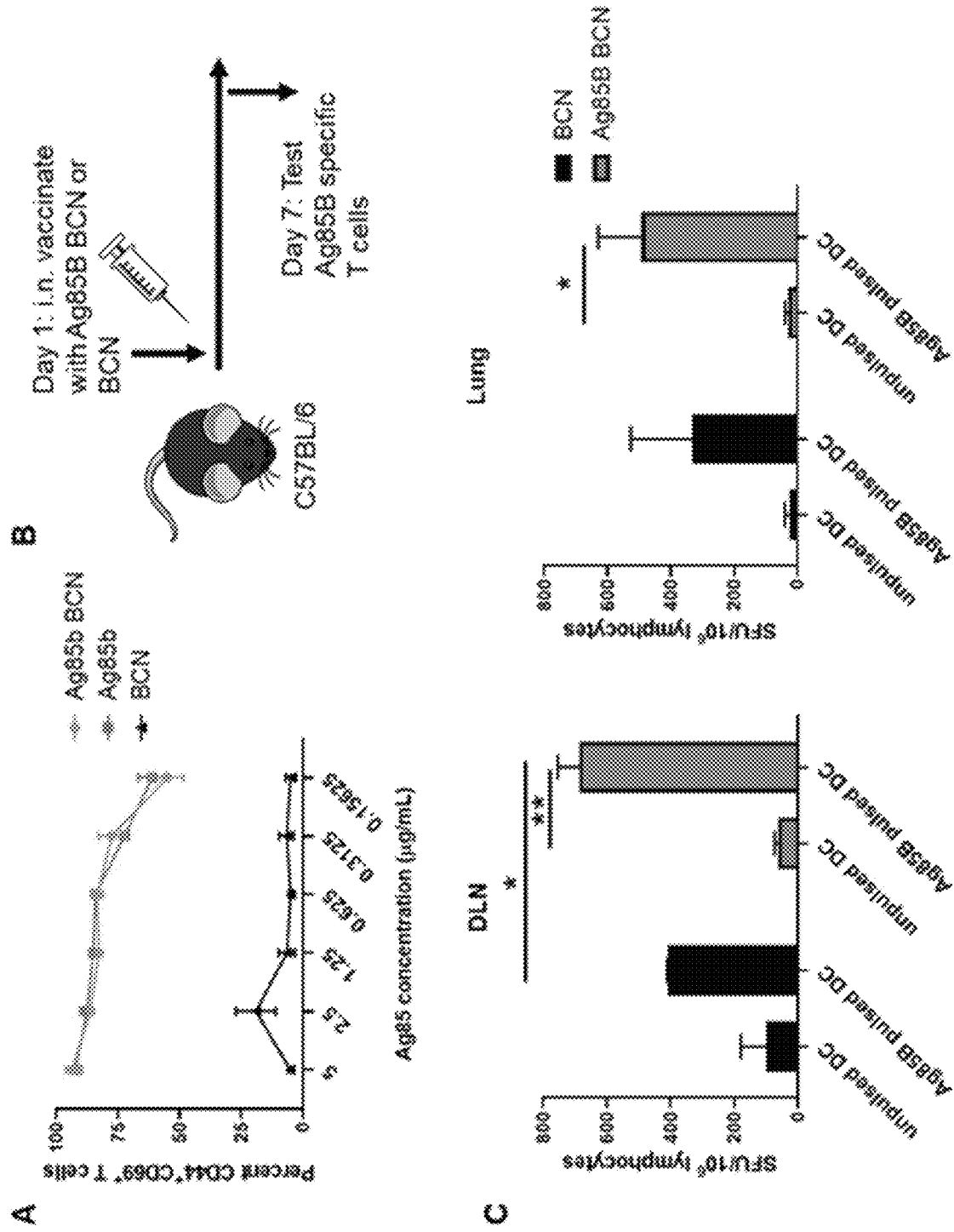

FIGS. 33A-33C show Ag85B results. (A) bmDCs pulsed overnight with Ag85B were co-cultured with p25-restricted T cells for 48 h and analyzed by FACS for CD44 and CD69 expression. N=3 per condition. (B & C) Draining lymph node and lung lymphocytes from 1-week Ag85B BCN vaccinated C57BL/6 mice were co-cultured with Ag85B-pulsed DCs for 18 h and analyzed for IFNγ-spot forming units (SFU) using ELISPOT. N=2 per condition. *p<0.05, **p<0.01.

INCORPORATION BY REFERENCE

All publications, patents, and patent applications mentioned in this specification are herein incorporated by reference to the same extent as if each individual publication, patent, and patent application was specifically and individually indicated to be incorporated by reference.

DETAILED DESCRIPTION OF THE INVENTION

The present disclosure demonstrates multi-subunit vaccines that can elicit both MHC and CD1 restricted T cell responses. As demonstrated herein, the present invention provides multi-subunit vaccines that can elicit an immune response against both lipid and protein antigens providing a more robust immune response. The multi-subunit vaccine comprises a nanomaterial, for example, a nanocarrier system or nanobiomaterial-based vaccine delivery system that can deliver a lipid antigen alone or in combination with peptides to elicit an immune response, and specifically in some embodiments a CD1 T cell response.

Compositions

The present disclosure provides compositions of multi-subunit vaccines comprising a nanobiomaterial based vaccine delivery system, which can elicit both a lipid- and peptide-specific immune response.

Prior live attenuated bacterial vaccines elicit broad immune responses against both lipid and protein components, yet current subunit vaccine strategies do not sufficiently incorporate the lipid-specific mechanisms of immunity.

Subunit vaccines combine immunodominant protein or peptide antigens from pathogens with select adjuvants, aiming to provide a more scalable, reproducible, low cost and rapid alternative to attenuated vaccines that contain live pathogens. Unfortunately, current subunit vaccines lack lipid antigens and rarely achieve the broad T cell responses required for lasting immunological memory and protection. In contrast, attenuated vaccines lack customization and scalability, but incorporate the entire pathogen to provide both protein and lipid antigens during immunization. This combination of lipid and protein antigens activates a broad spectrum of effector T cells, including conventional MHC-restricted T cells that respond to peptides and display considerable polymorphism, as well as nonpolymorphic CD1-restricted T cells that are directed against specific lipids. A more biomimetic strategy that simultaneously activates both lipid- and peptide-specific T cells may therefore show enhanced efficacy and control compared to subunit vaccines limited to protein antigens.

The neglect of lipid antigens from current subunit vaccines and immunotherapies is primarily due to 1) difficulties in targeted delivery of lipids, and 2) a lack of suitable mouse models. In humans, the CD1 family consists of group 1 CD1 molecules (CD1a, CD1b, and CD1c) and the group 2 CD1 molecule CD1d. Mice, however, only express CD1d.

The present disclosure addresses these problems with subunit vaccines by providing a broader immune response by targeting both lipids and peptide antigens using nanomaterials as carriers.

The present disclosure also provides engineered nanobiomaterials, novel sustained release hydrogels, and rationally selected antigen and adjuvant combinations that can elicit an immune response.

Vaccines described herein include nanobiomaterial (NBM) delivery systems (e.g., nanocarrier system or nanobiomaterial-based vaccine delivery system) for enhanced delivery of lipid antigens, protein antigens, and combinations thereof to induce CD1- and MHC-restricted T cell response in a subject. The nanobiomaterial delivery systems are characterized by complex or vesicular nanoarchitectures capable of encapsulating or comprising as part of the nanocarrier lipid antigens, protein antigens, or combinations thereof. Nanoarchitectures of the nanobiomaterial are bicontinuous and may be characterized as, for example, nanospheres, filomicelles, cubisomes, vesicles, tubules, nested vesicles, filiments, and vesicular, multilamellar and tubular polymersomes. Polymersomes are comprised of three separate topological regions: an inner aqueous cavity, a hydrophobic membrane, and an external surface, that together allow for simultaneous or individual transport of both water soluble/hydrophobic and lipophilic/hydrophobic target molecules. Polymersomes may be vesicular, multilamellar or tubular.

Suitable methods are known in the art for making nanobiomaterials for use in the present vaccine compositions. See, for example, US 2018/0022878, which is incorporated herein by reference in its entirety.

In some embodiments, the nanobiomaterials are made using flash-nanoprecipitation. As used herein, "flash nanoprecipitation" (FNP) refers to a process in which a block copolymer is assembled into a nanocarrier architecture. FNP may also be used to load the nanocarrier with a lipid antigen, a protein antigen, or combinations thereof described herein. FNP methods employ multi-stream mixers in which an organic solution and a block copolymer dissolved in a suitable solvent are impinged upon an aqueous solution under turbulent conditions and subsequently introduced into an aqueous reservoir. The supersaturated conditions generated by the turbulent mixing induces precipitation of the block copolymer for stabilization of monodisperse nanoparticles, which may be loaded with a lipid antigen, a protein antigen, or combinations thereof as described herein. Mixing occurs over millisecond timescales and is followed by transfer to a reservoir comprising a second aqueous solution to strip away solvent still associating with the aggregated block copolymer. Flash nanoprecipitation advantageously allows for loading hydrophilic target molecules, such as, but not limited to, protein antigens described herein, as well as hydrophobic target molecules, such as, but not limited to, the lipid antigens described herein.

The nanobiomaterials may be formed from suitable amphiphilic copolymers. Amphiphilic copolymers are comprised of sub-units or monomers that have different hydrophilic and hydrophobic characteristics. Typically, these subunits are present in groups of at least two, comprising a block of a given character, such as a hydrophobic or hydrophilic block. Depending on the method of synthesis, these blocks could be of all the same monomer or contain different monomer units dispersed throughout the block, but still yielding blocks of the copolymer with substantially hydrophilic and hydrophobic portions. These blocks can be arranged into a series of two blocks (diblock) or three blocks (triblock), or more, forming the backbone of a block copolymer. In addition, the polymer chain may have chemical moieties covalently attached or grafted to the backbone. Such polymers are graft polymers. Block units making up the copolymer can occur in regular intervals or they can occur randomly making a random copolymer. In addition, grafted side chains can occur at regular intervals along the polymer backbone or randomly making a randomly grafted copolymer. The ratio of the hydrophobic to hydrophilic blocks of the copolymer will be selected such that the soluble and insoluble components are balanced and suitable aggregation for the desired architectures.

Suitable amphiphilic copolymers of the present invention are those polymers with a low glass transition temperature (Tg) hydrophobic block, typically below 0° C. or between about −70° C. and about 0° C. (i.e., less than about 10° C., 0° C., −5° C., −10° C., −20° C., −25° C., −30° C., −40° C., −45° C., −50° C., −60° C. or −70° C. and greater than about −70° C., −60° C., −50° C., −45° C., −40° C., −30° C., −25° C., −20° C., −10° C., or −5° C.). Polymers within this range will exhibit high mobility between polymer chains. Polymers which fit these characteristics include, without limitation, poly(ethylene glycol) (PEG), poly(propylene sulfide) (PPS), poly(ethylene sulfide), polycaprolactone, poly(dimethylsiloxane) and polyethylene. Polymers may also include chemical modifications or end caps. Chemical modification and end caps may include, but are not limited to, thiol, benzyl, pyridyl disulfide, phthalimide, vinyl sulfone, aldehyde, acrylate, maleimide, and n-hydroxysuccinimide groups. The chemical modification of the polymer may add a charged residue to the polymer or may be used to otherwise functionalize the polymer.

In some embodiments of the present invention, the polymer is poly(ethylene glycol)-bl-poly(propylene sulfide) (PEG-bl-PPS). In one embodiment, the polymer is $PEG_{17}$-bl-$PPS_{30}$-Thiol. Advantages of the PEG-b-PPS nanocarrier system include rapid gram-scale fabrication, stability for months to years when loaded with antigen and adjuvant, high loading efficiency for protein antigens (e.g., ~70% for albumin) and small molecule adjuvants (e.g., >90% for imiquimod derivatives), redox-sensitivity for intracellular delivery and enhanced antigen cross presentation, morphology-dependent targeting of antigen presenting cells (APC), amenability to multimodal imaging, and controllable immunostimulation when combining molecular payloads.

In some embodiments, the nanobiomaterial is a micelle. In some embodiments, the micelle is a solid-core spherical micelle comprising $PEG_{45}$-bl-$PPS_{29}$. In some embodiments, the solid-core spherical micelle comprises $PEG_{44}$-bl-$PPS_{14}$.

In some embodiments, the nanobiomaterial is a filomicelle. A filomicelle is a filamentous micelle, or more commonly referred to as a cylindrical micelle, structure with a continuous, extended internal hydrophobic region. In some embodiments, the filomicelle comprises vinyl sulfone functionalized $PPS_{44}$-bl-$PEG_{45}$ ($PPS_{44}$-bl-$PEG_{45}$-VS). In some embodiments, the filomicelles include $PEG_{44}$-b-$PPS_{45}$ and VS-$PEG_{44}$-b-$PPS_{45}$.

In some embodiments, the nanobiomaterial is a vesicular polymersome with an aqueous core. In some embodiments, the aqueous core vascular polymersome comprises $PEG_{17}$-bl-$PPS_{30}$.

In some embodiments, the nanobiomaterial is a bicontinuous nanosphere (BCN). As used herein, "bicontinuous nanosphere (BCN)" refers to nanocarriers with extensive bicontinuous hydrophobic domains interspersed with ordered aqueous channels. At the time of filing, flash nanoprecipitation is the only know method for scalable fabrication of monodisperse BCN. Based on small angle X-ray scattering (SAXS) analysis, BCN have primitive type cubic internal organization (Im3m) as confirmed by Bragg peaks with relative spacing ratios at $\sqrt{2}$, $\sqrt{4}$, and $\sqrt{6}$. BCN can incorporate both hydrophobic (e.g., lipid antigen) and hydrophilic (e.g., protein antigen) payload molecules. In some embodiments, the BCN include PEG-bl-PPS. In some embodiments, the BCN include $PEG_{17}$-bl-$PPS_{75}$.

In some embodiments, the nanobiomaterial carrier is cross-linked to form a hydrogel. These hydrogel delivery systems provide controlled and sustained release of lipid-antigen-loaded nanobiomaterials, which are able to activate CD1-restricted T cells. The nanobiomaterial hydrogels include filomicelles cross-linked via a cross-liking agent. Variations in the concentration of the amphiphilic copolymer, functionalized amphiphilic copolymer, and a cross-linking agent will change the structure and release properties of the hydrogel. Suitable methods for nanobiomaterial hydrogel formation are known in the art. See, for example, Karabin et al. ("Sustained micellar delivery via inducible transitions in nanostructure morphology," Nat Commun., 2018, 9(1):624).

As used herein, "cross-linking agent" refers to a compound or composition that facilitate chemical crosslinking of nanocarrier structures. Cross-linking chemistry is well established in the art and an ordinarily skilled artisan will understand suitable cross-linking agents and cross-linking chemistry suitable for use in the disclosed hydrogels. Suitable cross-linking agents include, but are not limited to, vinyl sulfone (VS), a PEG-thiol crosslinker, click chemistry reagents (e.g. aldehyde/oxyamine, alkene/azide, azide alkyne etc.), sugars (e.g. dextrans), peptides, and proteins in both native or denatured states. In some embodiments, the amphiphilic copolymer is functionalized with the cross-linking agent.

In some embodiments, the hydrogel includes vinyl sulfone functionalized PEG-bl-PPS (VS-PEG-bl-PPG. In some embodiments, the hydrogel includes methoyl-functionalized PEG-bl-PPS (MeO-PEG-bl-PPS). In some embodiments, the hydrogel includes both VS-PEG-bl-PPS and MeO-PEG-bl-PPS. In some embodiments, the hydrogel includes 5%, 10%, 15%, 20%, 25%, 30%, 35%, 40%, 45%, or 50% by mass of VS-PEG-b-PPS. Changing the ratio thereof alters the rheological properties of the hydrogel. For example, oscillatory mode rheological analysis of cross-linked scaffolds composed of 10%, 20%, and 30% by mass of the VS-PEG-b-PPS revealed increases in elastic modulus from 10 to 1000 Pa over the tested frequency range. Furthermore, this ratio can modulate the degradation rate and release properties of the hydrogel. See, for example, Karabin et al. ("Sustained micellar delivery via inducible transitions in nanostructure morphology," Nature Communications, 2018, 9:624) which describes the changes in hydrogel properties based on changes in the polymer ratio.

The hydrogels may be tuned for sustained release of the lipid-antigen, the protein antigen or combinations thereof. In some embodiments, the sustained release is over a period of at least 3 days, at least 5 days, at least 7 days, at least 10 days, at least 15 days, at least 20 days, at least 25 days, or at least 30 days, at least 5 weeks, at least 6 weeks, at least 7 weeks, at least 8 week, at least 9 week, or at least 10 weeks.

In some embodiments, the filomicelle hydrogels are formulated into injectable drug depots for injection into a subject. As used herein, "depot" refers to a localized mass, which may include a drug, a vaccine, a suitable carrier, and combinations thereof, typically administered by injection that gradually releases a drug, vaccine, or other pharmaceutical component to its surrounding or is gradually absorbed by the surrounding tissue. Depot injections allow for release of an active compound, drug, vaccine, etc., to be released consistently over longer periods of time.

Without wishing to be bound by any particular theory or embodiment, the nanobiomaterial carriers described herein are advantageous over other carriers know in the art as they are non-immunostimulatory and non-tolerogenic in the absence of loaded antigen. Other carriers are known to elicit an immunostimulatory or tolerogenic response even in the absence of loaded antigen.

As used herein, "non-immunostimulatory" refers to a compound, composition, or carrier that does not elicit an immune response when administered to a subject in the absence of an antigen or adjuvant. In some embodiments, the compound, composition, or carrier is less immunositmulatory that other compounds, compositions, or carriers known in the art.

As used herein, "non-tolerogenic" refers to a compound, composition, or carrier that does not produce or cause immunological tolerance when administered to a subject in the absence of an antigen or adjuvant. In some embodiments, the compound, composition, or carrier is less tolerogenic than other compounds, compositions, or carriers known in the art.

In some embodiments, the present disclosure provides subunit vaccines comprising a nanobiomaterial carrier loaded with a lipid antigen, a peptide antigen, or combinations thereof for eliciting an immune response in a subject. In some embodiments, the subunit vaccine is capable of eliciting a combined CD1- and MHC-restricted T cell response to a bacterial antigen, specifically in one embodiment, *Mycobacterium tuberculosis* (Mtb) lipids and antigens. Further, the present disclosure provides a lipid/protein multi-antigen vaccine. In some embodiments, the multi-subunit vaccine comprises at least one antigenic lipid (e.g., at least one bacterial lipid, for example at least one Mtb lipid) and at least one peptide antigen (e.g., at least one bacterial peptide antigen, for example, at least one Mtb antigen) into a single subunit vaccine formulation. This multi-subunit vaccine is able to targets both conventional and unconventional T cell subsets to enhance overall immunity to the pathogen, for example, Mtb infection. The methodology and antigen/adjuvant delivery systems can be used for multi-subunit vaccines for TB and other bacterial pathogens to provide scalable routes of rapid vaccine fabrication.

CD1-restricted T cell activation is associated with an increase in interleukin-2 (IL-2), tumor necrosis factor α (TNF-α), interferon γ (IFN-γ), interleukin 17A (IL-17A), and granulocyte-macrophage colony-stimulating factor (GM-CSF) cytokine production as well as an increase in CD69, CD25, CD44, CD62L, CCR7, and CD103 expression in cluster of differentiation 1 (CD1) T cells. CD1-restricted T cell activation can be measured by suitable means known in the art for measuring cytokine release and cell specific marker expression, including, but not limited to flow cytometry, enzyme-linked immunosorbent assay (ELISA), cytometric bead array (CBA), enzyme-linked immune absorbent spot (ELISPOT), and proliferation assays. Human genes encoding CD1 T cell receptors are nonpolymorphic and all humans will have a similar or shared response to lipid antigens because they share similar genes encoding these receptors. Accordingly, the population coverage of vaccines that employ CD1-restricted T cell lipid antigens will be very high. See In some embodiments, CD1-restricted T cell activation is measured using human group 1 CD1 transgenic (hCD1Tg) mouse model. The hCD1Tg mouse expresses human group 1 CD1 genes under an exogenous promoter. The hCD1Tg mouse model is described in detail in Felio et al. ("CD1-restricted adaptive immune responses to Mycobacteria in human group 1 CD1 transgenic mice," The Journal of Experimental Medicine, 2009, 206(11):2497-2509). In some embodiments, the transgenic mouse model expresses a T cell receptor specific for mycolic acid (DN1Tg).

MHC-restricted T cell activation is associated with an increase in interleukin-2 (IL-2), tumor necrosis factor α (TNF-α), interferon γ (IFN-γ), interleukin 17A (IL-17A), and granulocyte-macrophage colony-stimulating factor (GM-CSF) cytokine production as well as an increase in CD69, CD25, CD44, CD62L, CCR7, and CD103 expression in major histocompatibility complex (MHC) T cells. MHC-restricted T cell activation can be measured by suitable means known in the art for measuring cytokine release and cell specific marker expression, including, but not limited to flow cytometry, enzyme-linked immunosorbent assay (ELISA), cytometric bead array (CBA), enzyme-linked immune absorbent spot (ELISPOT), and proliferation assays.

Without wishing to be bound by any particular theory or embodiment, activation of CD1-restricted T cells is particularly advantageous in vaccination strategies. Human genes encoding CD1 T cell receptors are nonpolymorphic and all humans will have a similar or shared response to lipid antigens because they share similar genes encoding these receptors. Accordingly, the population coverage of vaccines that employ CD1-restricted T cell lipid antigens will be very high. This is in stark contrast to MHC-restricted T cells that respond to protein and peptide antigens, since MHC genes are the most polymorphic genes known. As a result, vaccines designed to elicit CD1-restricted T cell responses will have an effect in a very high percentage of the human population, while current vaccines that employ MHC-restricted T cell antigens only show effects for certain segments of the population and have high efficacy in an even lower percentage. See, for example, Bui et al. ("Predicting population coverage of T-cell epitope-based diagnostics and vaccines," BMC Bioinformatics, 2006, 153).

The term "vaccine," as used herein, refers to a biological preparation that contains antigen or immunogen that can elicit an immune response. The antigen or immunogen can be, for example, an infectious agent (e.g., microorganism) or components of the infectious agent (e.g. lipids or pepides), a molecule that resembles a disease-causing microorganism or cell, or a protein associated with an abnormal or diseased cell (e.g., tumor associated antigen). For example, antigens or immunogens may be made from a proteins of said microorganism or cell or its toxins. A vaccine is administered to an individual in order to stimulate that individual's immune response to said antigen or immunogen.

The term "subunit vaccine" as used herein refers to a vaccine preparation that contains at least two different antigen or immunogens that can elicit an immune response to a molecule or infectious agent, preferably in one embodiment, contains at least one lipid immunogen and at least on protein antigen for a given target molecule or infectious agent.

The term "antigen," or "immunogen" as used herein, refers to any molecule that is recognized by the immune system and that can stimulate an immune response. In some embodiments, the antigen is a peptide or protein or a lipid component. In another embodiment, the antigen is a component of an infectious agent. In a preferred embodiment, the antigen is a bacterial antigen.

Suitable infectious agents include, but are not limited to, for example, a virus, a bacteria, a fungus, a parasite, and the like.

Suitable bacteria include, but are not limited to, for example, Mycobacterium tuberculosis (Mtb), Escherichia coli, Salmonella, Helicobacter pylori, Neisseria gonorrhoeae, Neisseria meningitides, Streptococcus, bacillus, tuberculosis, leprosy, Legionella, Listeria and Brucella and the like. Suitable parasites include, but are not limited to, for example, parasites malaria, Leishmania, Cryptosporidium, Cyclospora, Toxoplasma gondii, Plasmodium spp and the like. In a preferred embodiment, the infectious agent is a bacteria, specifically Mycobacterium tuberculosis (Mtb).

As used herein, "lipid antigen" reference to a lipid moiety present on the exterior surface of or within an infectious agent and that elicits an immune response in a subject. Suitable lipid antigens may be lipid components of the cell walls or cell membranes of infectious agents. The range of known self and foreign lipid antigens that are presented by CD1 molecules includes extremely diverse types of lipids including lipopeptides, diacylglycerolipids, sphingolipids, mycolates, phosphomycoketides, but also small molecules. Among these are self-lipids, such as sulfatide or isoglobotrihexosylceramide (iGb3), but also many microbial antigens from pathogenic bacteria, such as didehydroxymycobactin or glucose monomycolate. Suitable lipid antigens are known and described in the art and may include, but are not limited to, mycolic acid, dieoxymycobactin, mannosyl phosphomycoketide, Mtb total lipid extract (Tlip), sulfoglycolipid (SGL), phosphatidyl mannoside 2 (PIM2), phosphotidyl mannoside 6 (PIM6), lipoarabinomannan (LAM), trehalose dimycolate (TDM), glucose monomycolate (GMM), Didehydroxymycobactin (DDM-838), Glucose Monomycolate (GMM), Mannosyl-1β-phosphomycoketide (β-MPM), and Phosphatidylinositol mannoside-4 (PIM-4), α-galacturonosyl ceramide (GalA-Gsl), diacylglycerol glycolipids from the pathogenic bacterium Borrelia burgdorferi (BbGl-2c), phenyl 2,2,4,6,7-pentamethyldihydrobenzofuran-5-sulfonate (PPBF), α-galactosylceramide (aGalCer), palmitic acid, isoglobotrihexosylceramine, sulfatide, phosphatidylcholine, spingosine and variants thereof, fatty acid variants, and combinations thereof. See, for example, Schiefner et al. ("Presentation of lipid antigens by CD1 glycoproteins," Curr Pharm Des., 2009, 15(28):3311-3317) and Zajonc ("The CD1 family: serving lipid antigens to T cells since the Mesozoic era," Immunogenetics, 2016, 68(8):561-576), each of which is incorporated herein by reference. In some embodiments, the lipid antigen is a total lipid extract from a bacterium, fungi, or other infectious agent. In some embodiments, the lipid antigen is a lipid specific to a bacterium, fungi, or other infections agent.

As used herein, "peptide antigen" and "protein antigen" are used interchangeably and refer to peptide moieties specific to an infectious agent that elicit an immune response in a subject. Suitable protein antigens may be a peptide component from an infectious agent. Suitable *Mycobacterium tuberculosis* protein antigens are known and described in the art and may include, but are not limited to, *Mycobacterium Tuberculosis* major secretory protein antigen 85A (Ag85A), Antigen 85B (Ag85B), Mtb early secretory antigenic target 6 (ESAT-6), Low Molecular Weight Protein Antigen 7 EsxH (Protein TB10.4), and combinations thereof. Protein antigens from other infectious agents are also suitable for use herein. Suitable protein antigens may include bacterial antigens, fungal antigens, viral antigens, parasitic antigens, or antigens from other infectious agents.

The terms "polypeptide," "peptide," and "protein," as used herein, refer to a polymer comprising amino acid residues predominantly bound together by covalent amide bonds. By the term "protein," we mean to encompass all the above definitions. The terms apply to amino acid polymers in which one or more amino acid residue may be an artificial chemical mimetic of a naturally occurring amino acid, as well as to naturally occurring amino acid polymers and non-naturally occurring amino acid polymers. As used herein, the terms may encompass amino acid chains of any length, including full length proteins, wherein the amino acids are linked by covalent peptide bonds. The protein or peptide may be isolated from a native organism, produced by recombinant techniques, or produced by synthetic production techniques known to one skilled in the art.

The vaccine formulations can further comprise one or more adjuvants. As used herein, "adjuvant" refers to a compound or composition that enhances the effectiveness of a vaccine composition. Suitable adjuvants are known in the art and may include, but are not limited to, Toll-like receptor 4 (TLR4) agonist monophosphoryl lipid A (MPLA), Toll-like receptor 9 (TLR9) agonist CpG oligonucleotide, stimulator of interferon genes (STING) ligand cyclic-di-GMP (c-diGMP), Pam3Cys, polyinosinic:polycytidylic acid (poly I:C), 1H-imidazo[4,5-c]quinoline (Gardiquimod™), 5,6-dimethylxanthenone-4-acetic acid (DMXAA), flagellin, complete Freund's adjuvant (CFA), incomplete Freund's adjuvant (IFA), imiquimod and variants thereof, resiquimod, CL075, DS802, CL097, and combinations thereof.

In some embodiments, the subunit vaccine composition further includes a pharmaceutically acceptable carrier. As used herein, "pharmaceutically acceptable carrier" refers to liquid and solid carriers, vehicles, fillers, diluents, encapsulating material, or excipients used in the art for production and delivery of vaccines. Pharmaceutically acceptable carriers are typically non-toxic and inert. A pharmaceutically acceptable carrier can contain pharmaceutically acceptable additives such as acidifying agents, alkalizing agents, antimicrobial preservatives, antioxidants, buffering agents, chelating agents, complexing agents, solubilizing agents, humectants, solvents, suspending and/or viscosity-increasing agents, tonicity agents, pharmaceutically acceptable salts, wetting agents, or other biocompatible materials. A tabulation of ingredients listed by the above categories, may be found in the *U.S. Pharmacopeia National Formulary*, 1857-1859, (1990).

Some examples of the materials which can serve as pharmaceutically acceptable carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen free water; isotonic saline; Ringer's solution, ethyl alcohol and phosphate buffer solutions, as well as other nontoxic compatible substances used in pharmaceutical formulations. Wetting agents, emulsifiers and lubricants such as sodium lauryl sulfate and magnesium stearate, as well as coloring agents, release agents, coating agents, sweetening, flavoring and perfuming agents, preservatives and antioxidants can also be present in the compositions, according to the desires of the formulator.

Examples of pharmaceutically acceptable antioxidants include water soluble antioxidants such as ascorbic acid, cysteine hydrochloride, sodium bisulfite, sodium metabisulfite, sodium sulfite and the like; oil-soluble antioxidants such as ascorbyl palmitate, butylated hydroxyanisole (BHA), butylated hydroxytoluene (BHT), lecithin, propyl gallate, alpha-tocopherol and the like; and metal-chelating agents such as citric acid, ethylenediamine tetraacetic acid (EDTA), sorbitol, tartaric acid, phosphoric acid and the like.

A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

The vaccine formulation may additionally include a biologically acceptable buffer to maintain a pH close to neutral (7.0-7.3). Such buffers preferably used are typically phosphates, carboxylates, and bicarbonates. More preferred buffering agents are sodium phosphate, potassium phosphate, sodium citrate, calcium lactate, sodium succinate, sodium glutamate, sodium bicarbonate, and potassium bicarbonate. The buffer may comprise about 0.0001-5% (w/v) of the vaccine formulation, more preferably about 0.001-1% (w/v). Other excipients, if desired, may be included as part of the final vaccine formulation.

The remainder of the vaccine formulation may be an acceptable diluent, to 100%, including water. The vaccine formulation may also be formulated as part of a water-in-oil, or oil-in-water emulsion.

The vaccine formulation may be separated into vials or other suitable containers. The vaccine formulation herein described may then be packaged in individual or multi-dose ampoules, or be subsequently lyophilized (freeze-dried) before packaging in individual or multi-dose ampoules. The vaccine formulation herein contemplated also includes the lyophilized version. The lyophilized vaccine formulation may be stored for extended periods of time without loss of viability at ambient temperatures. The lyophilized vaccine may be reconstituted by the end user, and administered to a patient.

The term "lyophilization" or "lyophilized," as used herein, refers to freezing of a material at low temperature followed by dehydration by sublimation, usually under a high vacuum. Lyophilization is also known as freeze drying. Many techniques of freezing are known in the art of lyophilization such as tray-freezing, shelf-freezing, spray-freezing, shell-freezing and liquid nitrogen immersion. Each technique will result in a different rate of freezing. Shell-freezing may be automated or manual. For example, flasks can be automatically rotated by motor driven rollers in a refrigerated bath containing alcohol, acetone, liquid nitrogen, or any other appropriate fluid. A thin coating of product is evenly frozen around the inside "shell" of a flask, permitting a greater volume of material to be safely processed during each freeze drying run. Tray-freezing may be performed by, for example, placing the samples in lyophilizer, equilibrating 1 hr at a shelf temperature of 0° C., then cooling the shelves at 0.5° C./min to −40° C. Spray-freezing, for example, may be performed by spray-freezing into liquid, dropping by ~20 µl droplets into liquid $N_2$, spray-freezing into vapor over liquid, or by other techniques known in the art.

Vaccine Administration

To vaccinate a subject, a therapeutically effective amount of the subunit vaccine formulation as described herein is administered to the subject.

The term "administration," as used herein, refers to the introduction of a substance, such as a vaccine, into a subject's body. The administration, e.g., parenteral administration, may include subcutaneous administration, intramuscular administration, transcutaneous administration, intradermal administration, intraperitoneal administration, intraocular administration, intranasal administration and intravenous administration.

The vaccine or the composition according to the invention may be administered to an individual according to methods known in the art. Such methods comprise application, e.g. parenterally, such as through all routes of injection into or through the skin: e.g. intramuscular, intravenous, intraperitoneal, intradermal, mucosal, submucosal, or subcutaneous. Also, the vaccine may be applied by topical application as a drop, spray, gel or ointment to the mucosal epithelium of the eye, nose, mouth, anus, or vagina, or onto the epidermis of the outer skin at any part of the body.

Other possible routes of application are by spray, aerosol, or powder application through inhalation via the respiratory tract. In this last case, the particle size that is used will determine how deep the particles will penetrate into the respiratory tract.

Alternatively, application may be via the alimentary route, by combining with the food, feed or drinking water e.g. as a powder, a liquid, or tablet, or by administration directly into the mouth as a: liquid, a gel, a tablet, or a capsule, or to the anus as a suppository.

The term "therapeutically effective amount," as used herein, refers to an amount of an antigen or vaccine that would induce an immune response in a subject receiving the antigen or vaccine which is adequate to prevent signs or symptoms of disease, including adverse health effects or complications thereof, caused by infection with a pathogen, such as a virus or a bacterium. Humoral immunity or cell mediated immunity or both humoral and cell mediated immunity may be induced. The immunogenic response of an animal to a vaccine may be evaluated, e.g., indirectly through measurement of antibody titers, lymphocyte proliferation assays, or directly through monitoring signs and symptoms after challenge with wild-type strain. The protective immunity conferred by a vaccine may be evaluated by measuring, e.g., reduction in clinical signs such as mortality, morbidity, temperature, overall physical condition, and overall health and performance of the subject. The amount of a vaccine that is therapeutically effective may vary depending on the particular virus used, or the condition of the subject, and may be determined by a physician.

The term "protected," as used herein, refers to immunization of a patient against a disease. The immunization may be caused by administering a vaccine comprising an antigen. Specifically, in the present invention, the immunized patient is protected from a fungal, bacterial, or viral infection.

The terms "subject" and "patient" are used interchangeably and refer to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

Other aspects and advantages of the invention will appear in the examples outlined below. In the examples, reference is made to the accompanying drawings which form a part hereof, and in which there are shown, by way of illustration, preferred embodiments of the invention. Such embodiments do not necessarily represent the full scope of the invention, however, and reference is made therefore to the claims and herein for interpreting the scope of the invention.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. The term "consisting essentially of" and "consisting of" should be interpreted in line with the MPEP and relevant Federal Circuit's interpretation. The transitional phrase "consisting essentially of" limits the scope of a claim to the specified materials or steps "and those that do not materially affect the basic and novel characteristic(s)" of the claimed invention. "Consisting of" is a closed term that excludes any element, step or ingredient not specified in the claim.

The use of the term "or" in the claims is used to mean "and/or" unless explicitly indicated to refer to alternatives only or the alternatives are mutually exclusive. It is specifically contemplated that any listing of items using the term "or" means that any of those listed items may also be specifically excluded from the related embodiment.

Throughout this application, the term "about" means within 5% of a stated concentration range, density, temperature, or time frame.

As used herein the specification, "a" or "an" may mean one or more, unless clearly indicated otherwise. As used herein in the claims, when used in conjunction with the word "comprising," the words "a" or "an" may mean one or more than one.

The present invention is not intended to be limited to any examples provided.

EXAMPLES

Example 1

MA has very limited solubility and micellar stability in aqueous solutions, making efficient in vivo delivery a considerable challenge. Furthermore, presentation of MA requires complexation with CD1b molecules within lysosomes, which necessitates intracellular delivery (15). One strategy to address these issues is by packaging the lipid within a nanobiomaterial-based carrier with enhanced capability for in vivo endolysosomal delivery to antigen presenting cells (APCs), particularly dendritic cells (DCs). Such nanocarriers have become increasingly engineered and utilized for vaccination and immunotherapy to decrease non-specific cellular interactions, transport combinations of molecules with diverse physicochemical properties and enhance endocytosis by APC (16, 17).

Nanocarriers self-assembled from poly(ethylene glycol)-bl-poly(propylene sulfide) (PEG-PPS) copolymers have demonstrated considerable utility for intracellular delivery of immunostimulants and antigens (18-23). PEG-PPS assembles into lyotropic mesophases, enhancing overall aggregate stability under a range of conditions (18, 24, 25). Even at relatively low MW, PEG-PPS nanobiomaterials are highly stable in dilute aqueous solutions (26). An advantageous characteristic of PEG-PPS is that the PPS block is oxidation-sensitive and converts to the progressively more water soluble poly(propylene sulfoxide) and subsequently poly(propylene sulfone) derivatives in the presence of physiologic levels of reactive oxygen species (ROS) (22, 25, 27). This allows efficient disassembly of nanocarriers within APC lysosomes as well as early and late endosomes for enhanced antigen presentation and adjuvant stimulation (19-22). PEG-PPS nanocarriers have therefore been extensively employed for endosomal and lysosomal delivery to APCs (18-22, 28), and possess physicochemical properties beneficial for the controlled delivery of MA.

To study the dynamics and in vivo function of group 1 CD1-restricted T cells during Mtb infection, we have generated human group 1 CD1 transgenic mice (hCD1Tg) that mimic the human expression of group 1 CD1 as well as a MA-specific TCR transgenic mouse strain (DN1Tg/hCD1Tg) (13, 14). In this study, we have synthesized, assembled and employed MA-loaded PEG-PPS micellar nanocarriers to induce and characterize MA-specific T cell responses following pulmonary delivery in hCD1Tg mice. We synthesized two separate PEG-PPS fluorescent conjugates, each possessing the same copolymer but with distinct fluorophores to characterize MA delivery to and presentation by DCs both in vitro and in vivo. MA-loaded acid-sensitive fluorophore-conjugated micelles (MA-ASMc) (29) were employed to verify lysosomal delivery within bone marrow derived DCs (BMDCs) in vitro by confocal microscopy. Following intranasal administration, MA-ASMc additionally supported flow cytometric analysis of cellular biodistributions while MA-loaded micelles conjugated to a near-infrared fluorescence (NIRF) sensitive fluorophore (MA-NIMc) allowed assessment of the organ level biodistributions. By employing PEG-PPS nanobiomaterials with hCD1Tg mice, we present a versatile strategy that could be used to design and test future vaccine formulations that incorporate lipid antigens.

Materials and Methods

Ethics statement—This study was carried out in accordance with the recommendations in the Guide for the Care and Use of Laboratory Animals of the National Institutes of Health. The protocol was approved by the Institutional Animal Care and Use Committee of the Northwestern University (Protocol number: IS00004890).

Mice—Human CD1 transgenic mice (hCD1Tg) in B6 or MHC II-deficient background (14) and CD1b-restricted MA-specific TCR transgenic mice in $Rag^{-/-}$ background ($DN1Tg/hCD1Tg/Rag^{-/-}$) (13) were generated and maintained in house.

Mtb lipid antigens and antibodies—MA (MW 1,100-1, 300 Da) was purchased from Sigma-Aldrich (St. Louis, MO) and reconstituted in an organic solution that comprised of chloroform and methanol at a ratio of 3 to 1 and stored as aliquots at −20° C. Monoclonal antibodies against mouse CD11b (M1/70), CD11c (N418), NK1.1 (PK136), CD19 (6D5), Ly6G (1A8), CD25 (PC61), CD44 (1M7), CD69 (H1.2F3), CD103 (2E7), F4/80 (BM8), TCRβ (H57-597), Siglec F (E50-2440) and human TCR Vβ5.1 (LC4) with different fluorochrome conjugates were purchased either from BioLegend or eBioscience (San Diego, CA).

Figure 8:
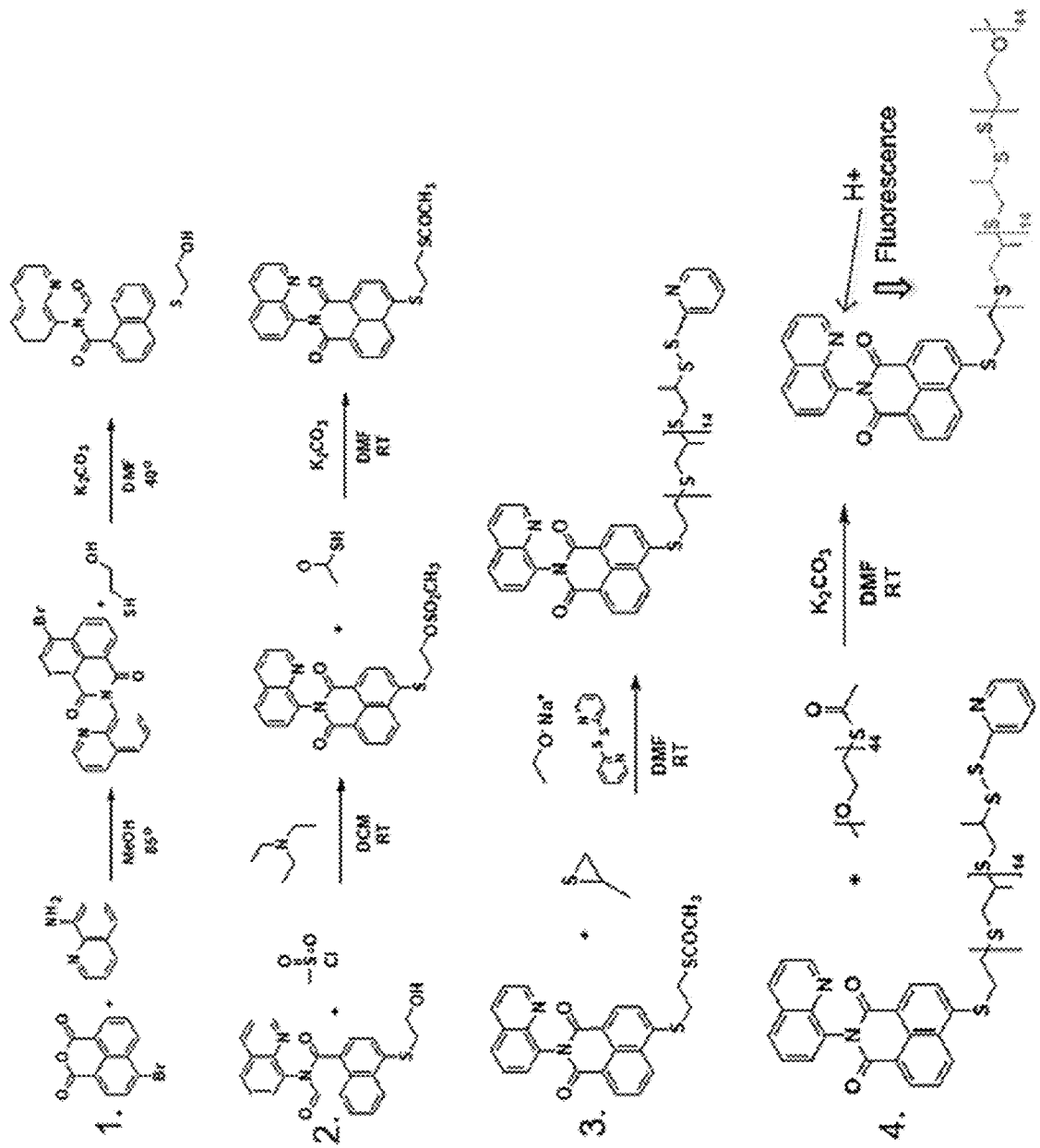
FIG. 8 shows the synthesis scheme of a poly(ethylene glycol)-bl-poly(propylene sulfide) amphiphilic copolymer tagged with a naphthalimide-derived acid sensitive fluorophore (PEG-PPS-ASF).

Synthesis of fluorescent $PEG_{44}$-$PPS_{15}$ copolymers—An acid-sensitive fluorophore (ASF, $\lambda_{ex}$=395 nm, $\lambda_{em}$=505 nm) derived from a 1,8-naphthalamide was synthesized as previously described (29, 30). The fluorophore was then modified to introduce a —SH containing linker on the naphthalimide ring for conjugation to PEG-PPS (31) (FIG. 8). The N-Quinolin-8-yl-4 bromo-1,8-naphthalimide was formed by mixing equal molar equivalents of 8-aminoquinoline and 4-bromo-1,8-napthalic anhydride in methanol and heating while stirring for two days. The mixture was cooled and the precipitate was collected by filtration. The product (a) was then reacted with 1.5 equivalents of mercaptoethanol and potassium carbonate in dimethylformamide (DMF) overnight to yield N-(quinolin-8-yl-4-mercaptoethanol)-1,8-napthalamide (b) that was isolated by precipitation into water followed by filtration. The hydroxyl group at the end of the linker was then modified by reaction with mesylate chloride in dichloromethane (DCM) in the presence of triethylamine overnight to generate N-quinolin-8-yl-napthalamide mesylate (c). The DCM was removed and the mesylate derivative was washed with water, dried and further reacted with thioacetic acid and potassium carbonate in DMF overnight. The product was isolated by precipitation in non-saturated NaCl to obtain the N-quinolin-8-yl-napthalamide thioacetate. The thio-protected group was used to initiate the ring opening polymerization of 15 molar equivalents of propylene sulfide in DMF for one hour, before end-capping with aldrithiol-2 which provides a disulfide link at the end of the PPS chain, useful for further substitution via disulfide exchange. The resulting polypropylene sulfide chain (PPS) with acid sensitive fluorophore was purified by precipitation in cold methanol and mixed with sodium methoxide-activated $PEG_{44}$ thioacetate ($PEG_{44}$-TAA) that was generated as previously described (18), in DMF overnight. The disulfide exchange reaction yielded $PEG_{44}$-$PPS_{15}$-ASF. PEG-PPS block copolymer used for in vivo NIRF imaging experiments was synthesized as previously described to possess a terminal free thiol (23), which was subsequently reacted with maleimide functionalized DyLight 755 (ThermoFisher Scientific) after micellar assembly to form $PEG_{44}$-$PPS_{15}$-DyLight 755. All the products obtained were confirmed by $^1$HNMR (Bruker Avance III 500 MHz):

N Quinolin-8-yl-4 bromo-1, 8-naphthalimide (a)

$^1$H-NMR (400 MHz, $CDCl_3$): δ 8.80 (1H, dd), 8.72 (1H dd), 8.66 (1H, dd), 8.48 (1H, d), 8.25 (1H, d), 8.10 (1H, d), 7.99 (1H, dd), 7.90 (1H, dd), 7.75 (2H, m), 7.42 (1H, dd).

Mercaptoethanol Derivative (b)

$^1$H-NMR (400 MHz, $CDCl_3$): δ 8.80 (1H, dd), 8.70 (2H, m), 8.54 (1H, d), 8.24 (1H, dd,), 7.98 (1H, dd), 7.82 (1H, dd), 7.78 (1H, dd), 7.71 (2H, m), 7.42 (1H, dd), 3.96 (2H, dd), 3.40 (1H, t), 2.04 (1H, t).

Mesylate Derivative (c)

$^1$H-NMR (400 MHz, CDCl$_3$): δ 8.80 (1H, dd), 8.70 (2H, m), 8.60 (1H, d), 8.24 (1H, dd,), 7.98 (1H, dd), 7.82 (1H, dd), 7.75 (2H, dd), 7.67 (1H, m), 7.38 (1H, dd), 4.42 (2H, t), 3.50 (2H, t), 2.99 (3H, s).

Thioacetate Derivative (d)

$^1$H-NMR (400 MHz, CDCl$_3$): δ 8.80 (1H, dd), 8.70 (2H, m), 8.60 (1H, d), 8.24 (1H, dd,), 7.98 (1H, dd), 7.82 (2H, m), 7.77 (1H, dd), 7.71 (1H, m), 7.42 (1H, dd), 3.38 (2H, t), 3.40 (2H, t), 2.40 (3H, s).

PPS$_{15}$-ASF (e)

$^1$H-NMR (400 MHz, CDCl$_3$): δ 1.35-1.45 (d, CH$_3$ in PPS chain), 2.6-2.7 (m, CH in PPS chain), 2.85-3.0 (m, CH$_2$ in PPS chain), 7.8-7.83 (m, 1H, pyridine group).

PEG-ss-PPS$_{15}$-ASF (e)

$^1$H NMR (CDCl$_3$): δ 1.35-1.45 (d, CH$_3$ in PPS chain), 2.6-2.7 (m, CH in PPS chain), 2.85-3.0 (m, CH$_2$ in PPS chain), 3.38 (s, 3H, —OCH$_3$), 3.52-3.58 (t, 2H, —OCH$_2$CH$_2$S), 3.5-3.7 ppm (broad, PEG chain protons).

Micelle nanocarrier formation and loading efficiency—Empty/vehicle acid sensitive micelles (V-ASMc) or MA-loaded micelles (MA-ASMc) were formed by dissolving 10 mg of PEG$_{44}$-PPS$_{15}$-ASF copolymer in 500 uL of chloroform, with or without 100 µg of MA, followed by the addition of 1 mL of endotoxin-free phosphate buffered saline (PBS). The mixture was stirred until chloroform was no longer present. V-ASMc and MA-ASMc were then centrifuged at 10,000 RPM for 5 minutes to remove precipitates. NIRF-sensitive PEG$_{44}$-PPS$_{15}$-DyLight 755 micelles with (MA-NIMc) and without loaded MA (V-NIMc) were formed in a similar manner, with Dylight 755 (Thermo Fischer Scientific) added after nanocarrier formation and allowed to mix overnight. Excess dye was removed by gravity filtration on a Sephadex LH-20 column (GE Healthcare Life Sciences). Resultant nanocarriers were characterized by cryotransmission electron microscopy (cryoTEM) and dynamic light scattering (DLS). To test the loading efficiency, MA was labeled with 4-bromomethyl-6,7-dimethoxycoumarin (Sigma-Aldrich) at 90° C. for 20 minutes in chloroform, with a molar excess of MA, then loaded into the copolymer to generate MA-loaded micelles as described above. Nanocarriers were then purified on an LH20 gravity column and the fluorescence of the derivatized MA was measured using a spectrophotometer ($\lambda_{ex}$=365 nm, $\lambda_{em}$=410 nm) (32).

Cell preparation and flow cytometry—Single-cell suspensions were prepared from the lung, spleen and mediastinal lymph nodes by mechanical disruption in HBSS/2% FBS. Lung was digested with collagenase IV (1 mg/mL) (Sigma) and DNase I (30 µg/mL) (Sigma) for 30 min at 37° C. before disruption. For cell surface staining, cells were pre-incubated with 2.4G2 Fcγ RII/RIII blocking mAb for 15 min and then stained with the appropriate combinations of mAbs listed below in HBSS/2% FBS for 30 min at 4° C. to define alveolar macrophages (SiglecF$^+$CD11b$^-$CD11c$^+$), dendritic cells (CD11b$^+$CD11c$^+$), monocytes (CD11b$^+$CD11c$^-$), neutrophils (CD11b$^+$Ly-6G$^+$), T cells (TCRβ$^+$), B cells (B220$^+$), and NK cells (NK1.1$^+$TCRβ−) cells. DN1 T cells are human TCR Vβ5.1-positive. CD25, CD44, CD69, CD62L, CCR7, and CD103 were used to define T cell activation. For intracellular cytokine staining, the procedure was performed as previously described (14) and stained with anti-IL-2, IFN-γ and TNF-α or isotype matched control antibodies. All mAbs were purchased form BioLegend (San Diego, CA) or BD Bioscience (San Jose, CA). Flow cytometry was performed with a FACS Cantoll (BD Biosciences, San Jose, CA) and analyzed using FlowJo software (Tree Star, Ashland, OR).

Dendritic cell generation and lipid antigen pulsing—Human CD1 transgene-positive (Tg$^+$) and -negative (Tg$^-$) bone marrow-derived dendritic cells (BMDCs) were derived from mouse bone marrow progenitors using GM-CSF and IL-4 (PeproTech, Rocky Hill, NJ) as previously described (33). At day 6 of culture, MA was dried out from solvent, resuspended in complete medium and sonicated for 10 min, then BMDCs were harvested and pulsed with free MA or MA-MC at different concentration for 18 h or indicated length of time. MA-pulsed BMDCs were washed twice and used as stimulators to activate DN1 T cells isolated from DN1Tg/hCD1Tg/Rag$^{-/-}$ mice.

ELISA and Cytometric Bead Array (CBA)—MA-ASMc, V-ASMc, or MA pulsed BMDCs were co-cultured with DN1 T cells for either 24 or 48 h and ELISA or CBA were performed respectively. For ELISA, 96-well plates were coated overnight with anti-mouse IFN-γ (clone: R4.6A2, Biolegend) at 4 µg/mL, washed and blocked, then incubated with culture supernatant for 2 hours followed by detection with biotinylated anti-IFN-γ mAb (clone: XMG1.2) and streptavidin conjugated with alkaline phosphatase (Bio-Rad). The color was developed using substrate pNPP (Sigma). For CBA, GM-CSF, IFN-γ, TNF-α, and IL-17 were measured using CBA Kit (BD Biosciences) according to the manufacturer's instructions. Flow cytometry was performed as described.

Confocal microscopy—BMDCs were seeded onto poly-L-lysine coated µ-Slide 8 well plates (ibidi) on day 6 of culture. On day 7, cells were pulsed for 4 hours with 1 mg/mL of V-ASMc or MA-ASMc. Live cells were treated with 100 nM LysoTracker Red (ThermoFisher Scientific) for 30 minutes and then imaged on a Leica SP5 II laser scanning confocal microscope.

In vivo imaging—Micelles covalently linked to Dylight 755 were prepared at a polymer concentration of 25 mg/mL and administered either intravenously (i.v.) or intranasally (i.n.). At 3, 24, and 48 h after administration, mice were sacrificed, and various organs were harvested to visualize the biodistribution of micelles by a near-IR In Vivo Imaging System (IVIS) (Center for Advanced Molecular Imaging, Northwestern University) with $\lambda_{ex}$=745 nm, $\lambda_{em}$=810 nm.

Immunization with MA-loaded PEG-PPS micelles—Mice were immunized i.n. with MA-ASMc containing 1-2 µg of MA in a total volume of 50 µL. Non-immunized or V-ASMc-immunized mice were used as controls. Mice were sacrificed for the detection of MA-specific T cell response at day 6 post-immunization for DN1 T cell-transferred recipients or at day 7 post-immunization for wildtype mice.

Adoptive transfer and proliferation assay—MA-specific TCR transgenic DN1 T cells were isolated from the spleen and lymph nodes of DN1Tg/hCD1Tg/Rag$^{-/-}$ mice and labeled with CellTrace Violet (ThermoFisher Scientific) as per manufacturer's instructions. 1×10$^6$ DN1 T cells were adoptively transferred to CD45.1 congenic hCD1Tg mice i.v. one day before immunization. Mice were sacrificed six days after immunization, and lymphocytes isolated from lungs, spleens and lymph nodes were used to detect the activation and proliferation of DN1 T cells by flow cytometry.

IFN-γ ELISPOT assay—IFN-γ ELISPOT assay was performed as previously described (14), with some modifications. Briefly, multiscreen-IP plates (Millipore, Bedford, MA) were coated with anti-IFN-γ mAb (An-18, eBioscience) at 5 µg/mL in PBS. Lymphocytes from immunized mice were incubated with hCD1Tg$^+$ or hCD1Tg$^-$ BMDCs pre-pulsed with or without MA for 18 h at 37° C. Plates were washed using PBS/0.05% Tween 20 and developed using biotinylated anti-IFN-γ mAb (R4.6A2, eBioscience), followed by streptavidin-conjugated alkaline phosphatase (Jackson ImmunoResearch Laboratories, West Grove, PA) and a BCIP/NBT substrate kit (Bio-Rad, Hercules, CA) according to the manufacturer's instruction. IFN-γ-producing cells were quantified using an ImmunoSpot reader (Cellular Technology, Shaker Heights, OH).

Statistical analysis—Statistical analyses were performed using Prism software 5.0 (GraphPad, La Jolla, CA). When comparing experimental values from two groups of mice, two-tailed student's t-tests were used. When comparing experimental values from multiple groups, one-way ANOVA Bonferroni post-tests were used. Statistically significant differences are noted (*$P<0.001$; $P<0.01$; *$P<0.05$).

Results

Figures 1A, 1B, 1C, 1D:
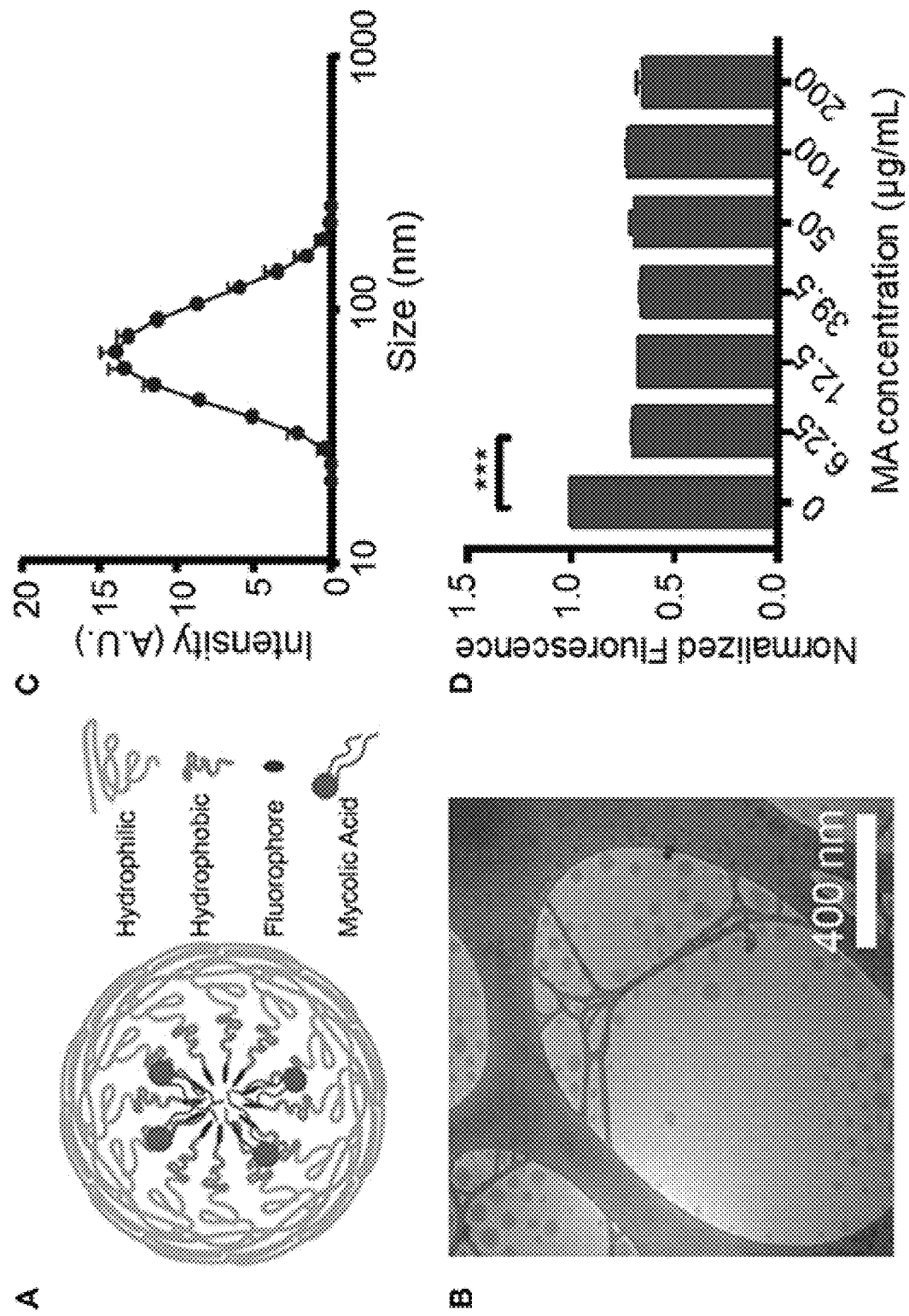
FIGS. 1A-1D show generation and characterization of mycolic acid-loaded micelles.
Figures 9A, 9B:
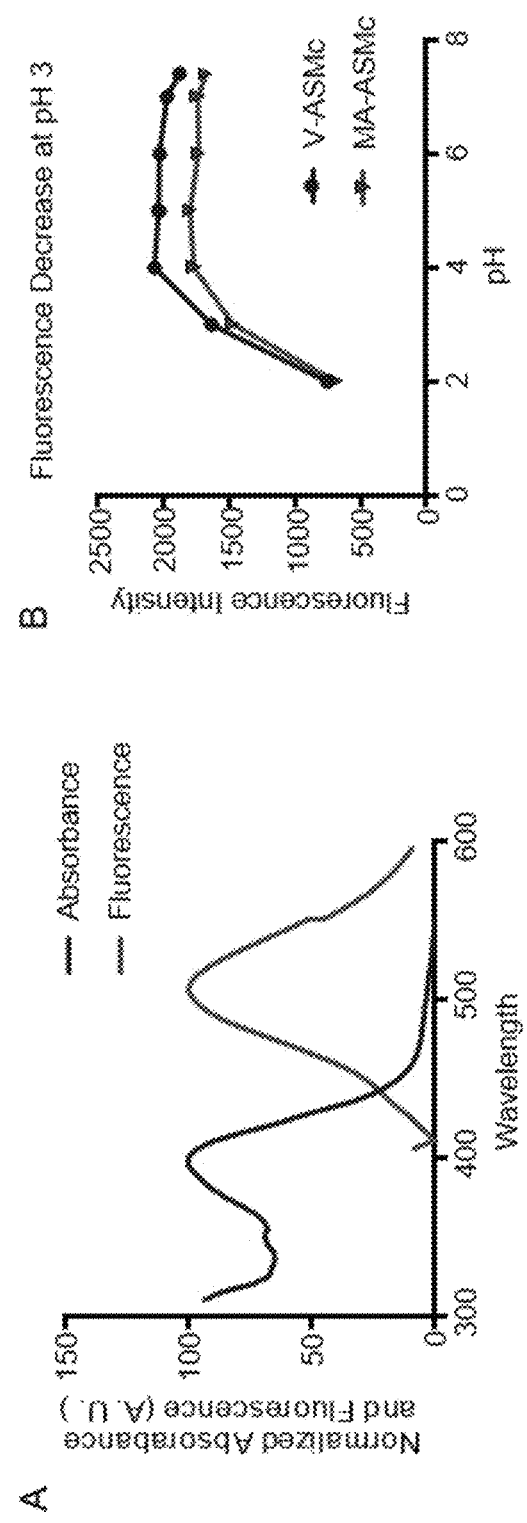
FIGS. 9A-9B show characterization of novel acid sensitive fluorophore.

Generation and characterization of mycolic acid-loaded micelles—Unlike most protein antigens, MA has limited solubility in water, making delivery to APCs particularly difficult. To overcome this challenge and increase the effective dose of MA, we encapsulated MA into a micellar nanocarrier (MA-Mc) using the controlled self-assembly of PEG-PPS, which can form diverse nanocarrier morphologies to efficiently deliver hydrophobic and hydrophilic moieties to APCs (21). To track the intracellular release of MA from micelles following uptake by cells, we modified the PEG-PPS copolymer by attaching an acid sensitive fluorophore (ASF, $\lambda_{ex}$=395 nm, $\lambda_{em}$=505 nm) (29) to the terminal end of the PPS block (PEG-PPS-ASF) (FIGS. 8 and 9A). The ASF contains an aminoquinoline ring, and the protonation of the tertiary amine within the ring leads to 98% quenching of fluorescence (FIG. S1) (30). We assembled MA-ASMc from this copolymer, where MA was loaded into the core of the nanocarriers (FIG. 1A). The spherical morphology of MA-ASMc was confirmed by cryo-transmission electron microscopy (cryoTEM) (FIG. 1B). The hydrodynamic diameter of MA-ASMc was measured by dynamic light scattering (DLS) to be 68 nm, a size comparable to the unloaded vehicle (V-ASMc), with a zeta potential of −16.5 (FIG. 1C, Table 1). The loading of MA led to a 30% decrease in the fluorescence intensity of MA-ASMc compared to V-ASMc (FIG. 1D), and this decrease was consistent in solutions with pH values of 4 and above (FIG. 9B).

TABLE 1

Properties of self-assembled PEG-PPS-ASF micelles with and without loading of mycolic acid.

| Size | PDI | Zeta Potential |
|---|---|---|
| Empty Micelle | 66.52 | 0.153 | −7.26 |
| MA-loaded Micelle | 68.13 | 0.140 | −16.5 |

Figure 10:
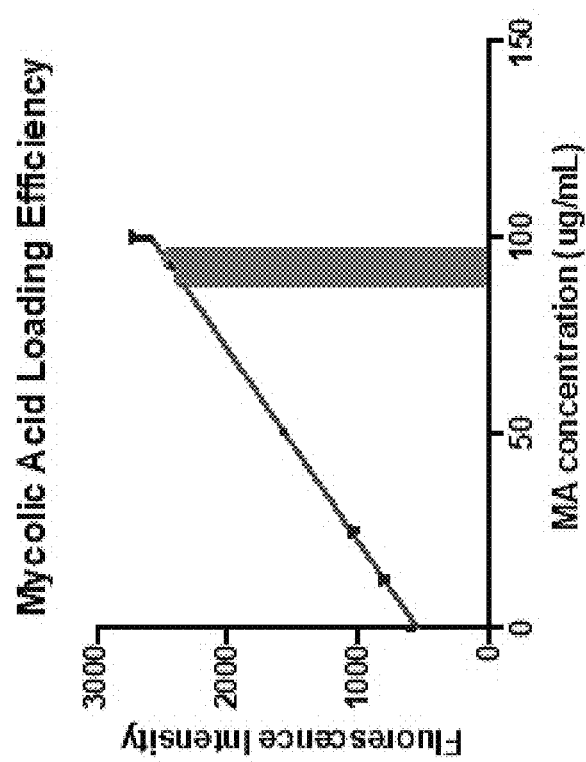
FIG. 10 shows loading efficiency of mycolic acid. Mycolic acid was conjugated to 4-bromomethyl-6,7-dimethoxycoumarin and then loaded into micelles. Fluorescence of the coumarin was measured after purification on an LH20 size exclusion column. The average loading efficiency of mycolic acid was 92±3%. Green bar represents range of loading efficiency for samples. Error bars represent SD, n=3.

As MA does not absorb light at any UV-Visible wavelength, to determine the loading efficiency of MA in PEG-PPS micelles, MA was first conjugated to 4-bromomethyl-6,7-dimethoxycoumarin and then loaded into PEG-PPS nanocarriers. After purification, the fluorescence of the coumarin derivative was measured. The loading efficiency of MA into micelles was 92±3% on average when 100 μg of coumarin-conjugated MA was used as a payload within 10 mg of PEG$_{44}$-PPS$_{15}$-ASF micelles (FIG. 10). This is significantly higher than the previously-reported 2% loading efficiency for poly(lactic-co-glycolic acid) (PLGA) nanocarriers (34). The predicted partition coefficient (log P) for alpha-MA (the most common mycolic acid) is 10.66, a value that is greater than the 9.056 log P of indocyanine green, which we previously found to have a 97% loading efficiency in PEG-PPS nanocarriers (18). Such a high loading efficiency is expected for a molecule with high solubility in non-polar solvents, and demonstrates the ability of these micelles to package a highly hydrophobic antigen for in vivo delivery. Unless otherwise stated, this ~1:35 molar ratio of MA to PEG-PPS-ASF was used for all subsequent experiments for consistency.

Figures 2A, 2B:
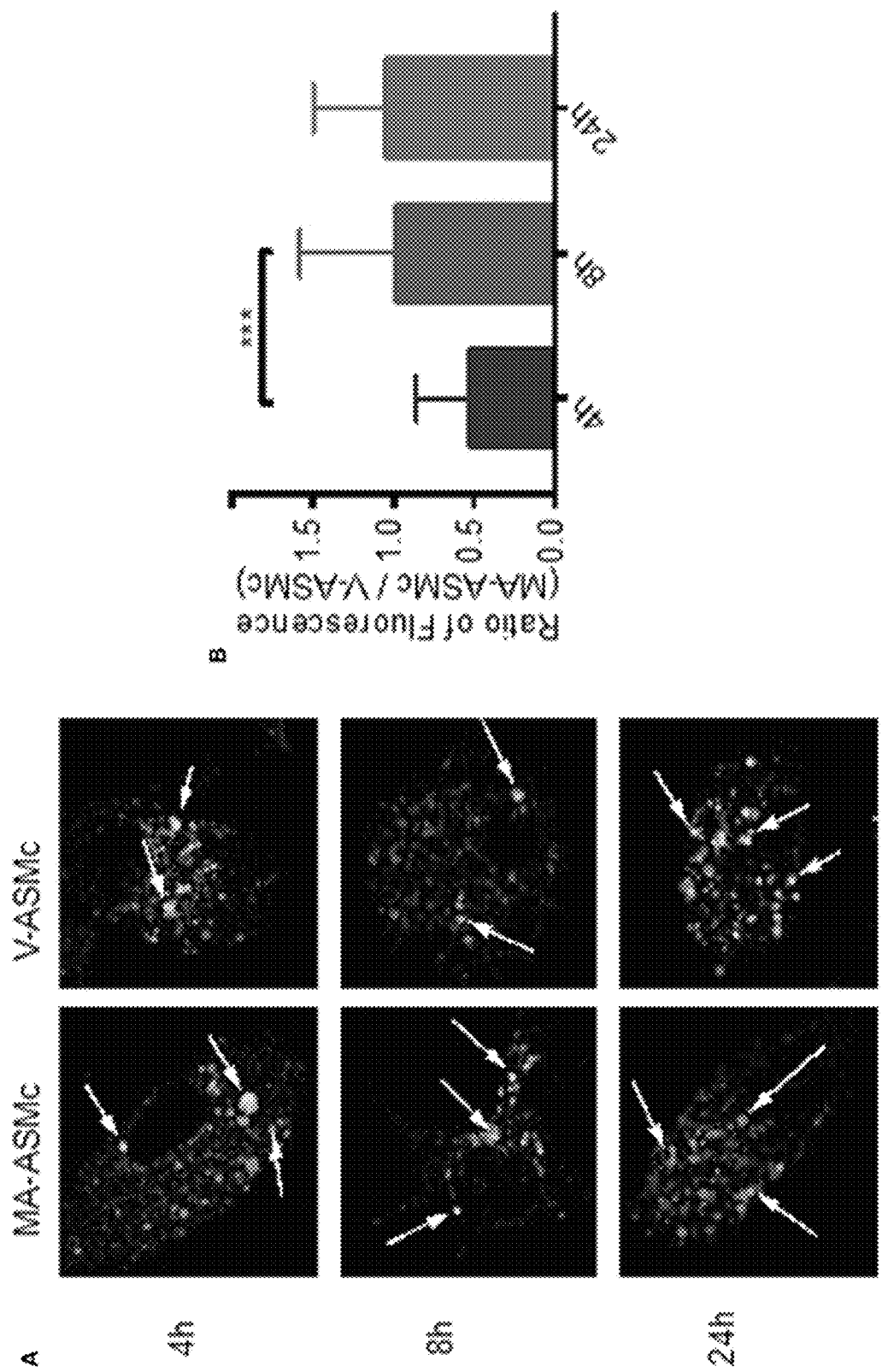
FIGS. 2A-2B show PEG-PPS-ASF functions as an on/off fluorescent switch to indicate intracellular release of MA following endocytosis by BMDCs.

MA-Mc are endocytosed by BMDCs and display superior efficacy over free MA in activating CD1b-restricted MA-specific TCR transgenic (DN1) T cells—For CD1-restricted T cell activation, MA-Mc must be internalized by CD1b-expressing BMDCs followed by release of MA from the nanocarriers into their lysosomal compartments. To track both the release of MA from nanocarriers and the uptake of the PEG-PPS copolymer, we live imaged BMDCs at different timepoints after pulsing with V-ASMCs and MA-ASMc. At all time-points assayed, co-localization was observed between the lysosome and the nanocarriers (FIG. 2A).

To measure differences in intracellular fluorescence between V-ASMc and MA-ASMc, we normalized the fluorescence intensity of the nanocarriers to the background cytosol fluorescence of each cell, excluding the endosomal punctate. After 4 h, there was a significantly higher fluorescence intensity observed for cells incubated with V-ASMc compared to those incubated with MA-ASMc at the same cell and micelle concentrations, resulting in a low MA-ASMc/V-ASMc cell fluorescence ratio (FIG. 2B). The MA-ASMc/V-ASMc cell fluorescence ratio significantly increased after 8 h but no significant change was observed for the 24 h timepoint, indicating that MA was likely released from the nanocarriers between 4 and 8 hours after uptake.

Figures 3A, 3B, 3C:
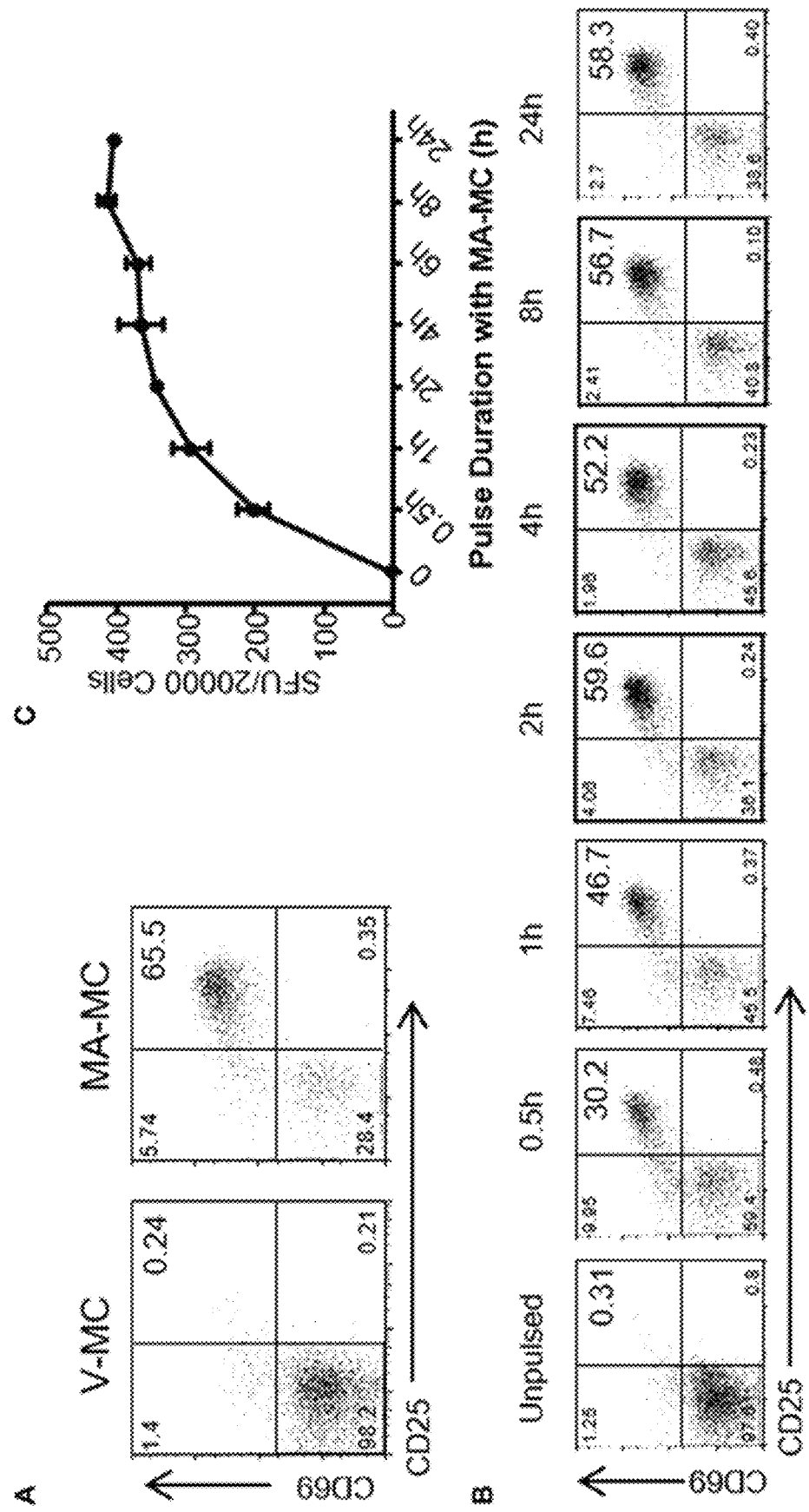
FIGS. 3A-3C show MA-ASMc are quickly endocytosed by BMDCs to activate MA-specific TCR transgenic T cells. Bone marrow derived dendritic cells (BMDCs) from hCD1Tg mice were pulsed with MA-ASMc at 0.2 µg/ml for different length of times and then co-cultured with MA-specific TCR transgenic T cells (DN1) for 24 h to determine the length of time needed to efficiently activate DN1 T cells by flow cytometry and IFN-γ ELISPOT.
Figures 11A, 11B, 11C:
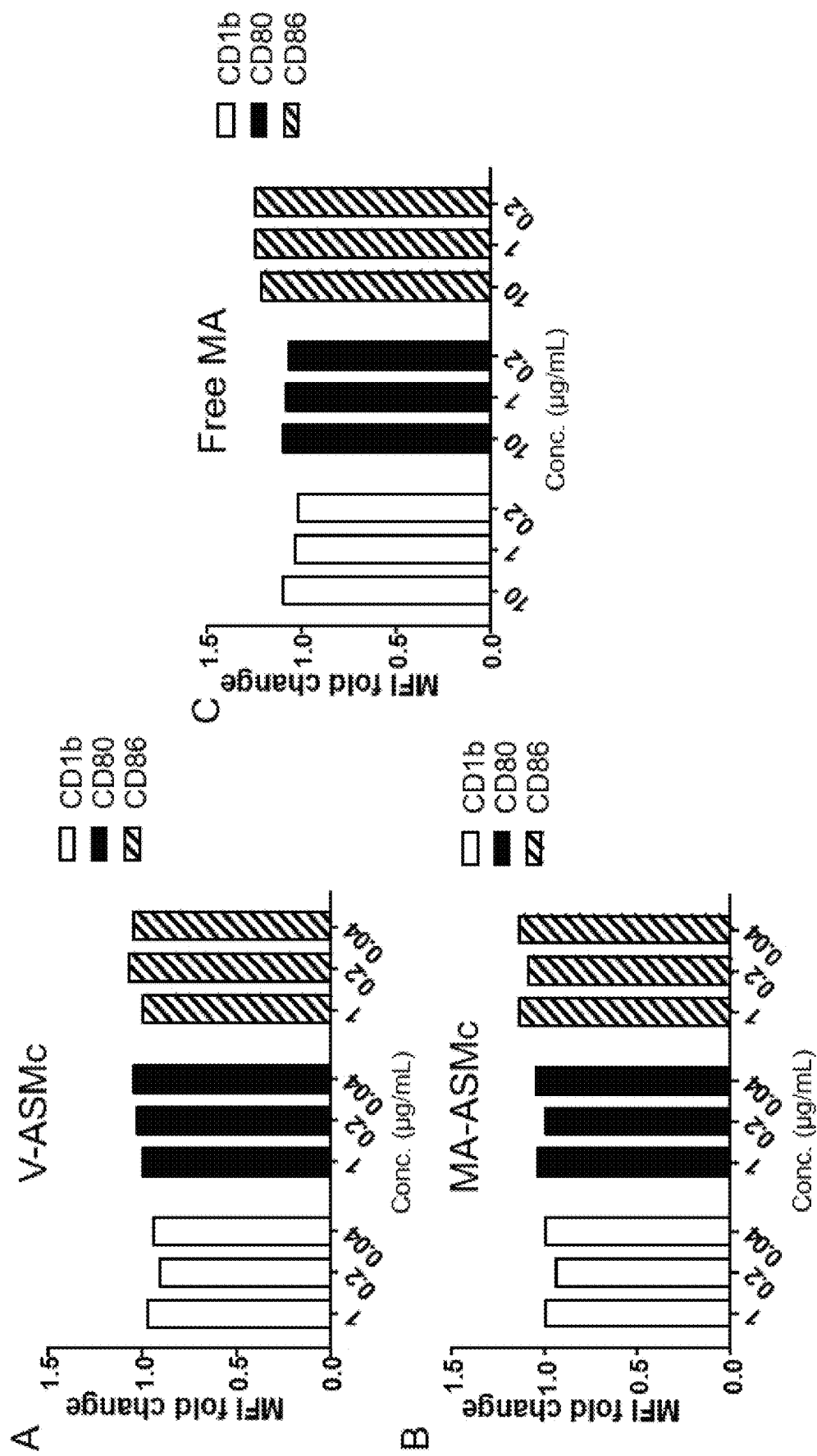
FIGS. 11A-11C show expression changes of CD1b, CD80 and CD86 on BMDCs pulsed vs unplused with empty micelles, MA-ASMc and Free MA. BMDCs from hCD1Tg$^+$ mice were differentiated in the presence of GM-CSF and IL-4 for 6 days and then pulsed or unplused with different concentration of empty micelles, MA-ASMc and Free MA for 24 h. The expression of CD1b, CD80 and CD86 on BMDCs were examined by flow cytometry. Data are expressed as fold changes of mean fluorescence intensity (MFI) of each marker on pulsed (n=3) vs unpulsed (n=2) BMDCs. Data are pooled from two experiments and expressed as mean.

To assess whether MA released from MA-ASMc was processed and presented by CD1b-expressing APCs, we examined whether hCD1Tg$^+$ BMDCs could activate MA-specific T cells after uptake of MA-ASMc (FIG. 3). hCD1Tg$^+$ BMDCs were pulsed with MA-ASMc for different lengths of time, their ability to activate CD1b-restricted MA-specific TCR transgenic DN1 T cells was measured by flow cytometry and ELISPOT assay to respectively quantify T cell expression of activation markers CD69 and CD25 as well as secretion of IFN-γ (FIGS. 3B and 3C). While V-ASMC pulsed hCD1Tg$^+$ BMDCs did not activate DN1 T cells (FIG. 3A), MA-ASMc-pulsed hCD1Tg$^+$ BMDCs activated DN1 T cells to their maximal level within 4 h of pulsing (FIGS. 3B and 3C), which correlates well with the timing of intracellular MA release indicated by the cell fluorescence measurements (FIG. 2B). In addition, pulsing with V-ASMC or MA-ASMc did not upregulate the expression of CD1b and DC maturation markers (CD80 and CD86) (FIG. 11), indicating non-immunomodulatory nature of PEG-PPS copolymer. Overall, these results verified that MA-ASMc effectively delivered MA to CD1b-expressing hCD1Tg$^+$ BMCDs for Ag presentation.

Figures 4A, 4B, 4C, 4D:
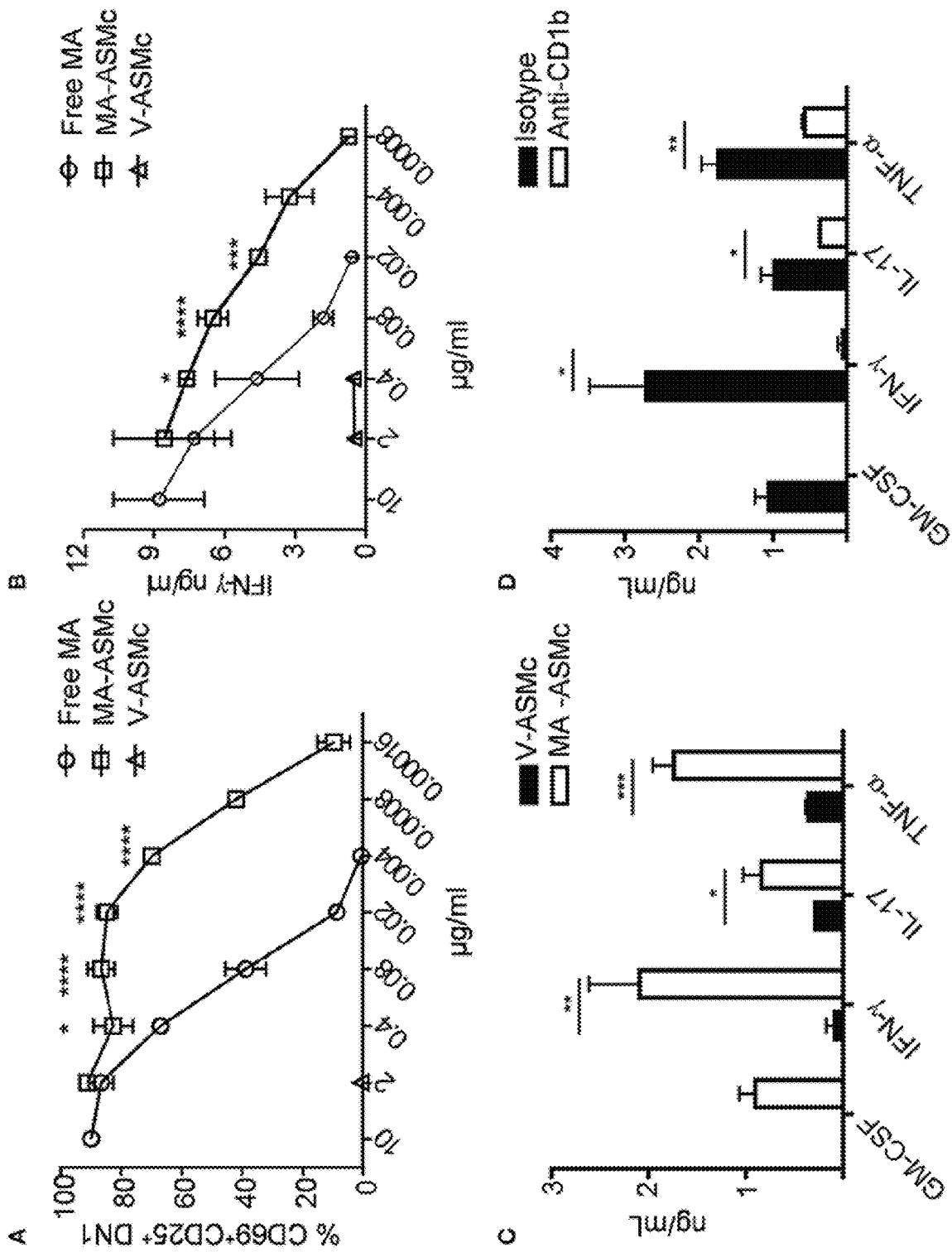
FIGS. 4A-4D show MA-ASMc are superior to free MA in activating MA-specific TCR transgenic T cells and elicit cytokine expression. BMDCs from hCD1Tg mice were pulsed with serial dilutions of MA-ASMc, free MA and V-ASMc overnight and then co-cultured with MA-specific TCR transgenic T cells (DN1) for 24 h. The efficiency of MA-ASMc and free MA in activating DN1 T cells was compared by flow cytometry and IFN-γ ELISA.

To compare the efficacy of MA-ASMc and free MA in activating MA-specific T cells, hCD1Tg$^+$ BMDCs were pulsed with various concentrations of free MA and MA-ASMc prior to co-culture with MA-specific DN1 T cells. Following 24 h of co-culture, the expression of activation markers (CD69 and CD25) and production of IFN-γ by DN1 T cells were determined by flow cytometry and ELISA, respectively. We found that while DCs pulsed with free MA were able to activate DN1 T cells as reflected by upregulation of activation markers (FIG. 4A) and IFN-γ production (FIG. 4B), an ~100 fold lower and ~20 fold lower respective concentration of MA was required to activate DN1 T cells to similar level when MA was delivered in the form of MA-ASMc (0.02 μg/mL MA in MC versus free MA). As a negative control, DCs pulsed with V-ASMc did not activate DN1 T cells (FIGS. 4A and 4B), further confirming the non-immunogenic nature of PEG-PPS copolymer. We characterized additional cytokines produced by DN1 T cells using CBA in the supernatant of a 48 h co-culture of DN1 T cells with either V-ASMc or MA-ASMc-pulsed hCD1Tg$^+$ BMDCs. We found DN1 T cells to secrete GM-CSF, IFN-γ, TNF-α, and IL-17 in response to stimulation with MA-ASMc-pulsed hCD1Tg$^+$ BMDCs (FIG. 4C). Cytokine production was CD1b dependent, as the response was blocked by an anti-CD1b antibody (FIG. 4D). These data indicated that encapsulation within PEG-PPS micelles greatly enhances the antigen presentation of MA by DCs. Furthermore, MA-ASMc elicits CD1b-dependent production of GM-CSF, IFN-γ, TNF-α, and IL-17 (FIG. 4D).

Figure 12:
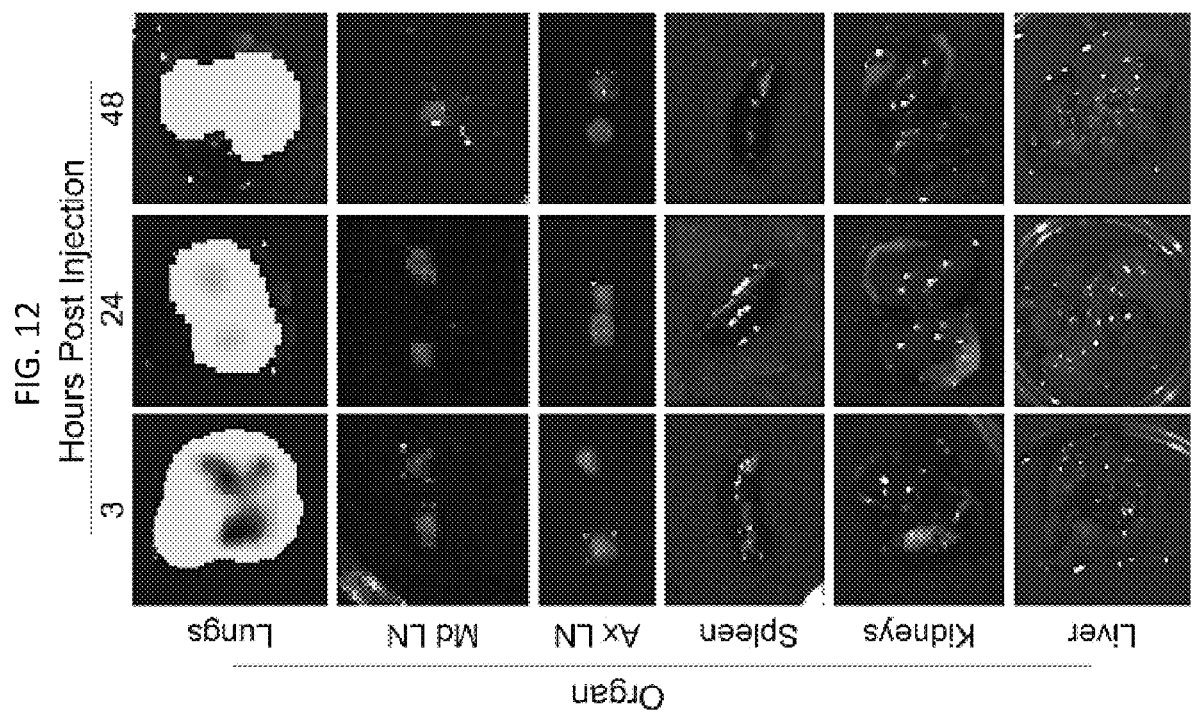
FIG. 12 shows MA-NIMc are mainly retained in the lung after i.n. delivery. The in vivo bio-distribution of micelles in different organs were visualized by In Vivo imaging system (IVIS) after pulmonary delivery of MA-MC conjugated with Dylight 755 (MA-NIMc).

MA-Mc are retained in the lung and taken up by alveolar macrophages and myeloid DCs after intranasal immunization—In past studies utilizing BCG, optimal protection has been achieved when the BCG vaccine is administered directly to the pulmonary mucosa, and it is generally established that the route of vaccine administration should follow the route of infection (35, 36). Therefore, we studied the induction of MA-specific T cell responses in the lung following pulmonary delivery of MA-MCs via the intranasal (i.n.) route. Our previous studies showed that PEG-PPS micelles could be taken up nonspecifically by cells of the mononuclear phagocytes system (MPS) and quickly removed from circulation after intravenous injection (23). The biodistribution of MA-loaded micelles following i.n. delivery had not yet been determined, and it was not known whether they would also be rapidly removed from circulation following i.n. administration. To address these questions, PEG$_{44}$-PPS$_{15}$ micelles were covalently linked to Dylight 755 via a thiol-maleimide conjugation for whole organ IVIS imaging. After i.n. administration, the biodistribution of micelles in different organs was assessed by NIRF imaging. We found that empty/vehicle Dylight 755-labeled micelles (V-NIMC) were mainly retained in the lung and reduced gradually from 3 h to 48 h post administration (FIGS. 5A and 5B). The signal in the mediastinal lymph nodes (MLN), axillary lymph nodes (AxLN), spleen, liver and kidneys was barely detectable (FIGS. 12A-12B). Therefore, although we have previously demonstrated that i.v. injection of PEG-PPS micelles targets multiple organs (23), the i.n. route was found to only target the lung at time points of 3 h, 24 h and 48 h after administration.

Figure 13:
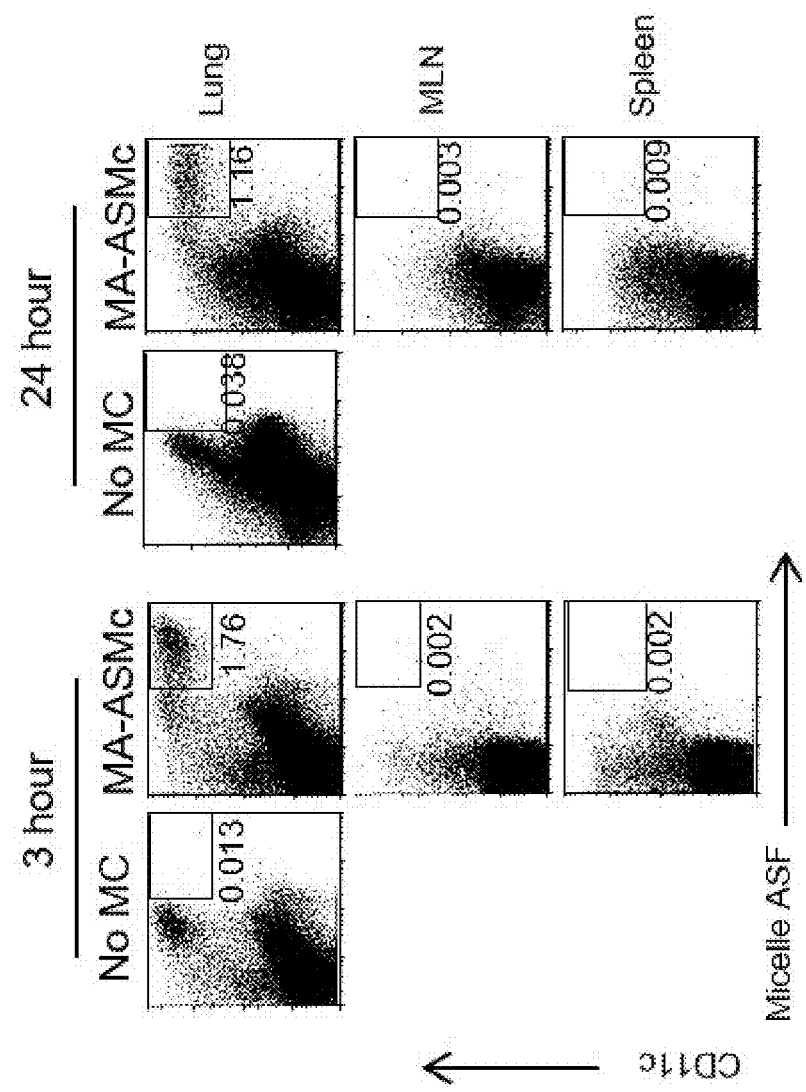
FIG. 13 shows MA-ASMc are not detectable in mediastinal lymph node and spleen after pulmonary delivery. The in vivo bio-distribution of ASF-labeled micelles (ASMc) in different organs was tracked by flow cytometry after pulmonary administration. MA-ASMc-carrying cells were not detectable in mediastinal lymph nodes and spleens of immunized mice from 3 h to 24 h after administration. Data are representative of three experiments.

To further investigate which subset of cells are responsible for the uptake of these micelles, we also intranasally administered the MA-ASMc. As described above, the fluorescence of the ASF conjugated to micelles can be readily detected within cells by flow cytometry after intracellular delivery. Single cell suspensions were prepared from the lung, MLN and spleen at 3 h and 12 h after i.n. delivery of MA-ASMc and cells positive for micelle fluorescence were examined by flow cytometry. We found that MA-ASMc were taken up selectively by a population of CD11c$^+$ cells in the lung (FIG. 5C), which included mostly alveolar macrophages (SiglecF$^+$CD11c$^+$CD11b$^-$) and a small percentage of myeloid DCs/interstitial macrophages (CD11b$^+$CD11c$^+$) (FIG. 5C) whereas T cells, B cells, NK cells, neutrophils and monocytes did not contain MA-ASMc (FIG. 5D). Consistent with the results from IVIS, no MA-ASMc containing cells could be detected in mLN and spleen (FIG. 13). These results suggested that MA-MCs were selectively phagocytosed by APCs like alveolar macrophages and myeloid DCs in the lung after intranasal delivery.

Figures 6A, 6B, 6C, 6D, 6E, 6F, 6G, 6H:
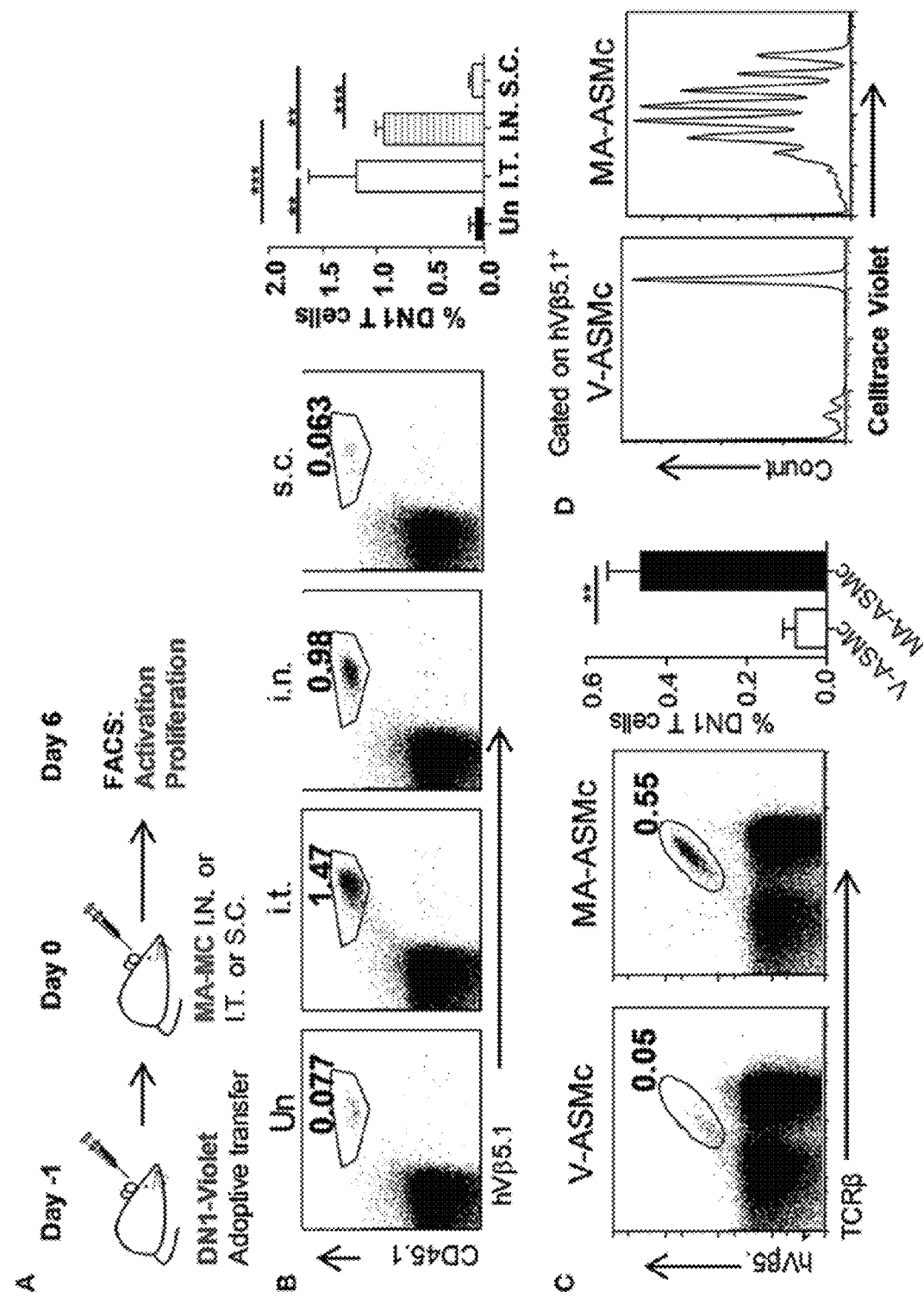
FIGS. 6A-6H show i.n. delivery of MA-ASMc induces proliferation and activation of adoptively-transferred MA-specific T cells. MA-specific T cells (DN1) were labeled with Celltrace violet and adoptively transferred into hCD1Tg mice 1 day before immunization with MA-ASMc or micelle vehicle (V-ASMc) via different routes. Six days later, DN1 T cells were harvested from V-ASMc- or MA-ASMc-immunized or unimmunized hCD1Tg mice for detection of proliferation and activation.
Figures 6A, 6B, 6C, 6D, 6E, 6F, 6G, 6H:
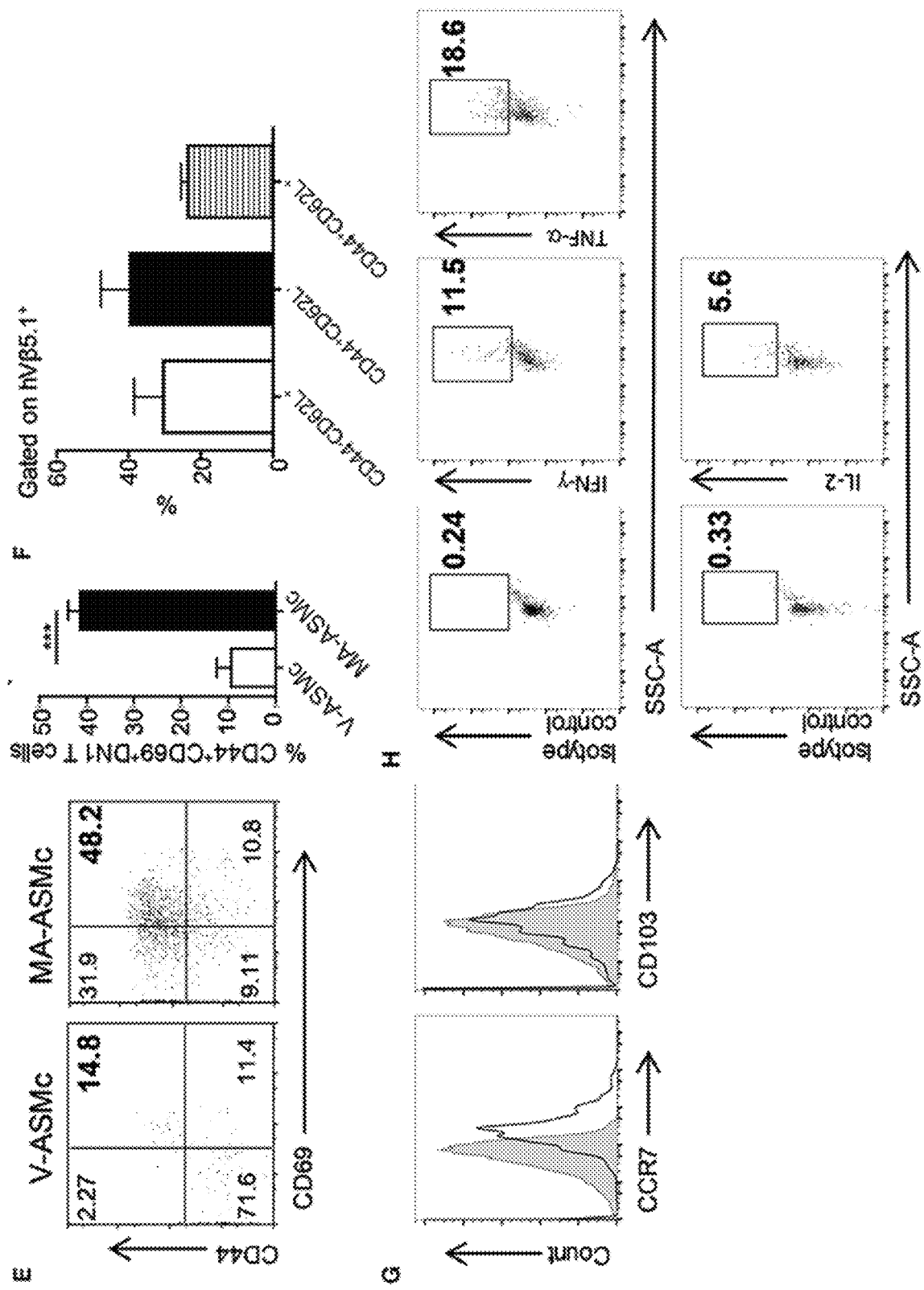
Figure 14:
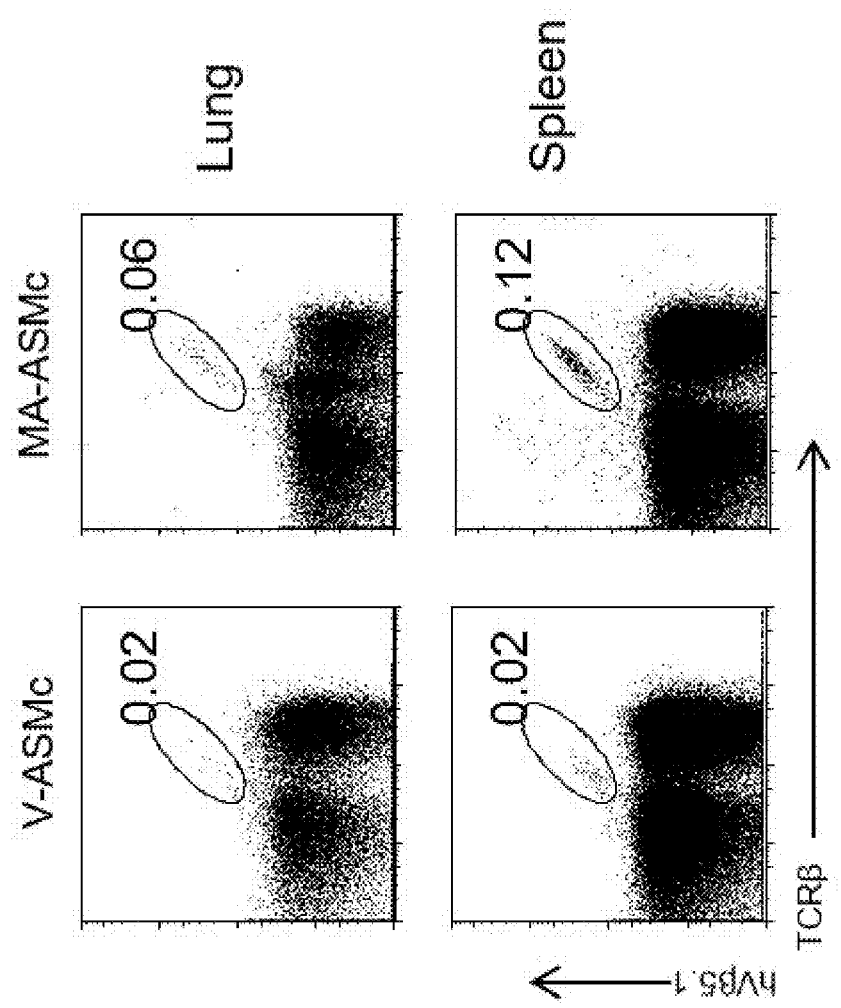
FIG. 14 shows i.n. delivery of MA-ASMc induces proliferation of adoptively-transferred DN1 T cells in the lung and spleen. Mycolic acid-specific TCR transgenic T cells (DN1) were labeled with Celltrace violet and adoptively transferred into hCD1Tg mice 1 day before immunization intranasally with MA-ASMc (n=4) or V-ASMc (n=3). Six days later, DN1 T cells were recovered from the lung and spleen of recipients. Representative dot plots of DN1 T cells in the lung and spleen were shown.

Intranasal delivery of MA-Mc induces proliferation and activation of adoptively-transferred MA-specific T cells—After determining that MA-loaded PEG-PPS micelles can be efficiently delivered to APCs in the lung following intranasal immunization, we next performed in vivo antigen presentation assays to determine whether MA-ASMc phagocytosed by APCs can activate MA-specific DN1 T cells in vivo (FIG. 6A). We also tested whether other routes of administration could be a better option than the intranasal route. CellTrace violet-labeled DN1 T cells were adoptively transferred into hCD1Tg mice. One day later, recipient mice were immunized by intranasl (i.n.), intratracheal (i.t.) and subcutaneous (s.c.) route with MA-ASMc. At day 6 post-immunization, we determined the proliferative capacity and activation status of DN1 T cells in the lung, MLN and spleen by flow cytometry. Compared to s.c. or no immunization, i.n. and i.t. induced significantly higher percentages of DN1 T cells recovered from MLN, while there is no significant difference in DN1 T cell level between i.n and i.t. immunized groups (FIG. 6B). Considering the invasiveness and higher technical requirement of i.t., our data supports i.n. delivery to be the most practical option for delivery of MA-ASMc. After i.n. immunization, MA-ASMc-immunized mice had a higher percentage of DN1 T cells than V-ASMc-immunized mice in MLN (FIG. 6C), lung and spleen (FIG. 14), although MA-ASMc-carrying DCs were not readily detectable in lymph node and spleen by flow cytometry (FIG. 13). In addition, DN1 T cells in MA-ASMc-immunized mice underwent extensive proliferation (FIG. 6D) and were significantly more activated, with a higher percentage of cells expressing CD44$^{hi}$CD69$^+$, compared to those in V-ASMc-immunized mice (FIG. 6E). In addition, DN1 T cells in MA-ASMc-immunized mice displayed an effector phenotype, as the majority are CD44$^{hi}$CD62$^-$ with some CCR7 expression, but no CD103 expression in the lung (FIGS. 6F and 6G). PMA/ionomycin-stimulated DN1 T cells were also able to produce IFN-γ, TNF-α, and IL-2 (FIG. 6H). These results demonstrate that pulmonary delivery of MA-ASMc leads to the presentation of MA by APCs and subsequent activation of MA-specific T cells in vivo.

Figures 7A, 7B, 7C, 7D:
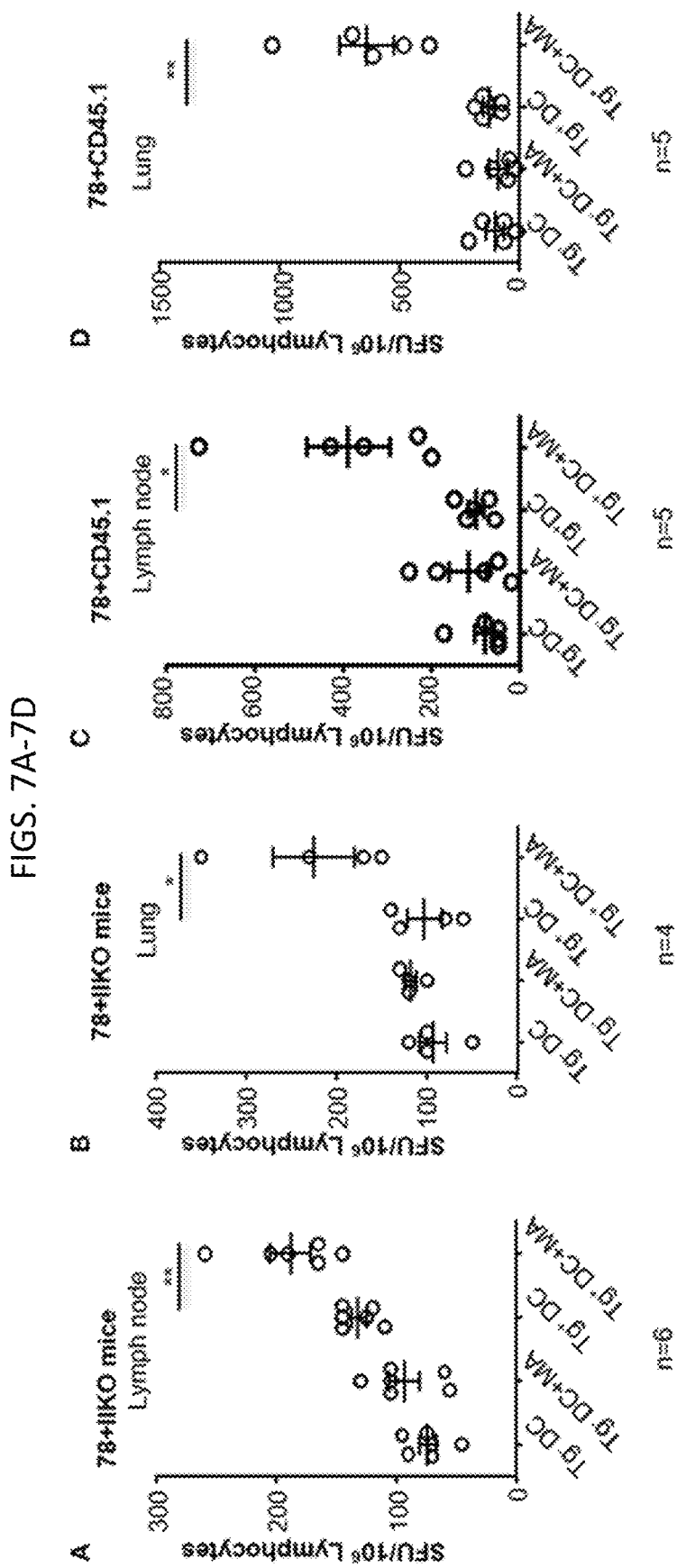
FIGS. 7A-7D show intranasal immunization with MA-ASMc induces MA-specific T cell response in hCD1Tg mice. hCD1Tg mice in MHC class II-deficient (FIGS. 7A and 7B) (n=4-6) or wildtype background (FIGS. 7C and 7D) (n=5) were immunized intranasally with MA-ASMc at a dosage of 1 µg mycolic acid. Mice were sacrificed 1 week later and lung (FIGS. 7B and 7D) and lymph node (FIGS. 7A and 7C) were harvested to make single cell suspension. Human CD1 transgenic and mycolic acid-specific T cell responses were detected in lung and lymph node in response to re-stimulation with mycolic acid pulsed or un-pulsed hCD1Tg negative (Tg$^-$) or positive (Tg$^+$) BMDCs in an IFN-γ ELISPOT assay. *, P<0.05; **, P<0.01.

Intranasal immunization of MA-Mc elicits polyclonal MA-specific T cell responses in hCD1Tg$^+$ mice—Although adoptively transferred MA-restricted DN1 T cells could be activated in vivo after immunization with MA-ASMc, there are more physiologically relevant ways to probe MA-loaded micelle immunogenicity. MA-specific T cells in hCD1Tg mice are polyclonal, have a more diverse TCR repertoire and are less frequent than adoptively transferred DN1 T cells. Therefore, to determine if MA-ASMc immunization could induce polyclonal MA-specific T cell responses in hCD1Tg mice, we immunized hCD1Tg mice i.n. with MA-ASMc and detected MA-specific responses by an IFN-γ ELISPOT assay. hCD1Tg$^+$ mice in both wildtype (B6) and MHC II-deficient (II$^{-/-}$) background were used for immunization, as our previous study showed that hCD1Tg/II$^{-/-}$ mice exhibited a more consistent group 1 CD1-restricted T response upon immunization with MA-pulsed DCs (14). At day 7 post-immunization, lymphocytes were isolated from the lung and MLN of MA-MC-immunized mice and stimulated in vitro with unpulsed or MA-pulsed BMDCs from hCD1Tg/II$^{-/-}$ (Tg$^+$) or II$^{-/-}$ (Tg$^-$) mice. Compared to stimulation with MA-pulsed Tg$^-$ DCs or unpulsed DCs, ELISPOT assays revealed that lymphocytes from both strains of immunized hCD1Tg+ mice had a significantly higher number of IFN-γ-producing cells when stimulated with MA-pulsed Tg+ DCs (FIG. 7). This data indicates that pulmonary delivery of MA-loaded PEG-PPS micelles efficiently elicit group 1 CD1-restricted MA-specific T cell responses in the lung and MLN of both hCD1Tg+ and hCD1Tg/II−/− mice.

Discussion

As CD1 molecules present many lipid antigens derived from Mtb and are non-polymorphic, CD1-restricted Mtb lipid antigens are likely to be recognized by most individuals, making them attractive vaccine targets and an untapped mechanism of improving immunity (15). In this study, using MA, a major component of the Mtb cell wall, we developed a MA-loaded micellar nanocarrier amenable to pulmonary administration and capable of significantly enhancing CD1b-restricted T cell responses both in vitro and in vivo. Our use of polymeric micelles self-assembled from ASF-conjugated $PEG_{44}$-$PPS_{15}$ provided evidence that this enhanced activation may be due to more efficient delivery of MA to APC endosomes for antigenic processing. Using human group 1 CD1-expressing mice generated in our lab, we demonstrated that MA-loaded PEG-PPS micelles can be taken up by APCs in vitro and in vivo, and subsequently elicit MA-specific CD1b-restricted T cell response in hCD1Tg+ mice in both monoclonal and polyclonal settings after pulmonary delivery. Our results support the notion that Mtb lipid antigen can be harnessed to develop vaccines by targeting group 1 CD1-restricted T cells.

Although a ~35:1 molar ratio of $PEG_{44}$-$PPS_{15}$-ASF:MA was consistently obtained, the maximum decrease in fluorescence of the ASF in the presence of loaded MA occurred at a higher molar ratio (e.g. 558:1), likely due to MA being a weak acid and the fluorophore being hindered within the micelle core. This, along with an insensitivity to pH ranges within lysosomes (pH 4.5-5.5), made $PEG_{44}$-$PPS_{15}$-ASF advantageous for detection of MA release within cells following endosomal delivery. As previously employed in non-biological systems (30), the naphthalimide-based dye thus functioned as an on/off fluorescent signal, here indicating when ~93% or more of MA had been released from micelles. To assess organ-level biodistributions of MA-Mc following intranasal administration, the ASF was replaced with a lipophilic NIRF-sensitive fluorophore. Conjugation of lipophilic fluorophores to the hydrophobic PPS terminal end of PEG-PPS copolymers sequesters the fluorophore, as well as most non-conjugated lipophilic payloads, within the micelle core upon self-assembly (18, 23). Thus switching the hydrophobic tag does not impact the nanocarrier biodistribution, which is instead dictated by the chemistry of the outer PEG corona and nanostructure morphology (23).

The most abundant lipid component of Mtb is MA, however human group 1 CD1 molecules present a large array of Mtb-derived lipids to cognate T cells. Although the relative immunodominance of lipid antigen during Mtb infection is currently unknown, a few Mtb lipid-based liposome vaccines have been explored either in vitro or in vivo. A glucose monomycolate (GMM)-loaded liposome vaccine was delivered to human DCs, which induced robust activation of GMM-specific human T cell clones in vitro (37). Lipoarabinomannan (LAM)-loaded liposomes triggered LAM-specific human T lymphocytes response in vitro (38). However, these studies were not further tested in animal models that express group 1 CD1 molecules. A mycobacterial total lipid-based liposome has been tested in guinea pigs that express conserved group 1 CD1 isoforms. Although total lipid-based liposomes induced CD1 restricted T-cell responses and demonstrated an improved pulmonary pathology (39, 40), the specific lipid component among the total lipids that was responsible for the pathological protection was not clear. Recently, a diacylated sulfoglycolipids ($Ac_2SGL$) and phosphatidylinositol mannoside 2 ($PIM_2$)-loaded liposome vaccine induced protective immune responses in guinea pigs (41), but the adjuvant effect of $PIM_2$ and trehalose-6,6-dibehenate (TDB), a component of the liposomal nanocarrier (42, 43), may complicate the bacterial and pathological protection observed.

The need to stably package lipids for increased delivery efficiency arises from their inherent hydrophobicity. As described above, liposomes have been employed as a delivery vehicle for several Mtb lipid-based vaccines (37-39, 44), but polymer-based nanocarriers provide advantages of increased stability (45), ease of preparation (18, 46), and control over bioresponsive payload delivery and targeting (19-23, 47). In our previous studies, self-assembled solid core nanocarriers and polymersomes assembled from PEG-PPS copolymers were shown to be an effective intracellular delivery system for protein antigens and adjuvants to enhance the induction of T cell immunity (20, 21). Here, our results demonstrated that PEG-PPS micelles are also an efficient delivery system for lipid antigens, achieving high loading efficiency, intracellular delivery of lipid antigen into the lysosome for CD1 receptor complexation, and amenability to i.n. administration for elicitation of localized CD1-restricted T cell responses. We selected MA as the lipid antigen because it stimulates potent cytokine production from CD1b-restricted human T cells (2), which contributes to the acute response of Mtb infection in humans and induces memory responses upon ex vivo re-stimulation in drug-treated TB patients (10). Importantly, MA-specific DN1 T cells were demonstrated to confer protection against Mtb infection in hCD1Tg mice (13). We hypothesized that combining 1) the efficient intracellular delivery of MA via our stable PEG-PPS nanocarrier platform and 2) in vivo evaluation of elicited CD1-restricted T cell responses in our unique hCD1Tg mice would provide a means for the rational design and optimization of subunit vaccines incorporating lipid antigens.

Although Mtb lipid-based liposomes have been tested in guinea pigs (39, 40, 44), in vivo biodistribution information was lacking. We therefore synthesized and assembled MA-NIMc to evaluate organ level biodistributions following i.n administration. MA-NIMc were not visible in organs outside the lung from 3 to 48 h after pulmonary delivery as assessed by IVIS imaging (FIG. 4). Flow cytometric analysis following i.n. administration of MA-ASMc revealed uptake mostly by alveolar macrophages but not by non-phagocytic cells. As CD1b is only expressed on DCs in the periphery (14, 15), the activation of MA-specific T cells detected in vivo in this study is unlikely due to direct presentation of MA/CD1b by macrophages, and may instead occur through cross presentation of MA by CD1b-expressing DCs that phagocytosed apoptotic macrophages (48). An earlier study showed that apoptotic vesicles containing Mtb antigens from mycobacteria infected-macrophages can be taken up by DCs, which present these antigens to T cells through MHC-I and CD1 molecules (49). Consistent with this report, we previously found that DN1 T cells are activated by Mtb-infected DCs but not by Mtb-infected macrophages (13). In the present study, DN1 T cells proliferated best in the MLN though MA-ASMc were not detected in organs outside the lung, suggesting that antigen transfer from MA-ASMc-carrying alveolar macrophage to migratory DCs occurred in vivo.

Of note, an MA-CD1b tetramer was developed recently for detecting MA-specific T cell responses in humans (50), however, it has not been validated for use in Mtb-infected animals. Therefore, we primarily detected MA-specific T cell responses by IFN-γ ELISPOT assay in immunized mice. It has been challenging to detect Mtb lipid-specific T cell responses in hCD1Tg mice after immunization with lipid-pulsed group 1 CD1-expressing BMDCs (14), possibly due to the low precursor frequency and/or inefficient expansion of group 1 CD1-restricted T cells in hCD1Tg mice. Therefore, the successful induction and detection of MA-specific T cells responses in hCD1Tg mice after immunization with MA-MCs is a significant advance towards developing an effective lipid-based vaccine against TB.

We observed that eliciting a T cell response did not require adjuvant. However, our nanocarrier platform lends itself to delivery of many different immunostimulants. Adjuvants for enhancement of responses against lipid-antigen have yet to be identified, and our MA-MC/hCD1Tg system presented here provides an excellent means for extensive screening of adjuvant candidates, as PEG-PPS nanocarriers can be engineered to simultaneously deliver combinations of both hydrophobic and hydrophilic payloads (18, 23, 28). We did not observe any adjuvant effect from the unloaded PEG-PPS V-ASMc or V-NIMc on DC maturation in vitro or in vivo, which supports our previous findings that PEG-PPS nanocarriers are non-immunogenic and are not sufficient to stimulate the immune system without adjuvanting payloads (18, 19, 21, 23). Future work can include adding synergistic combinations of adjuvants, and testing the delivery of MA with different morphologies of PEG-PPS nanocarriers to distinct APC populations.

Figure 15:
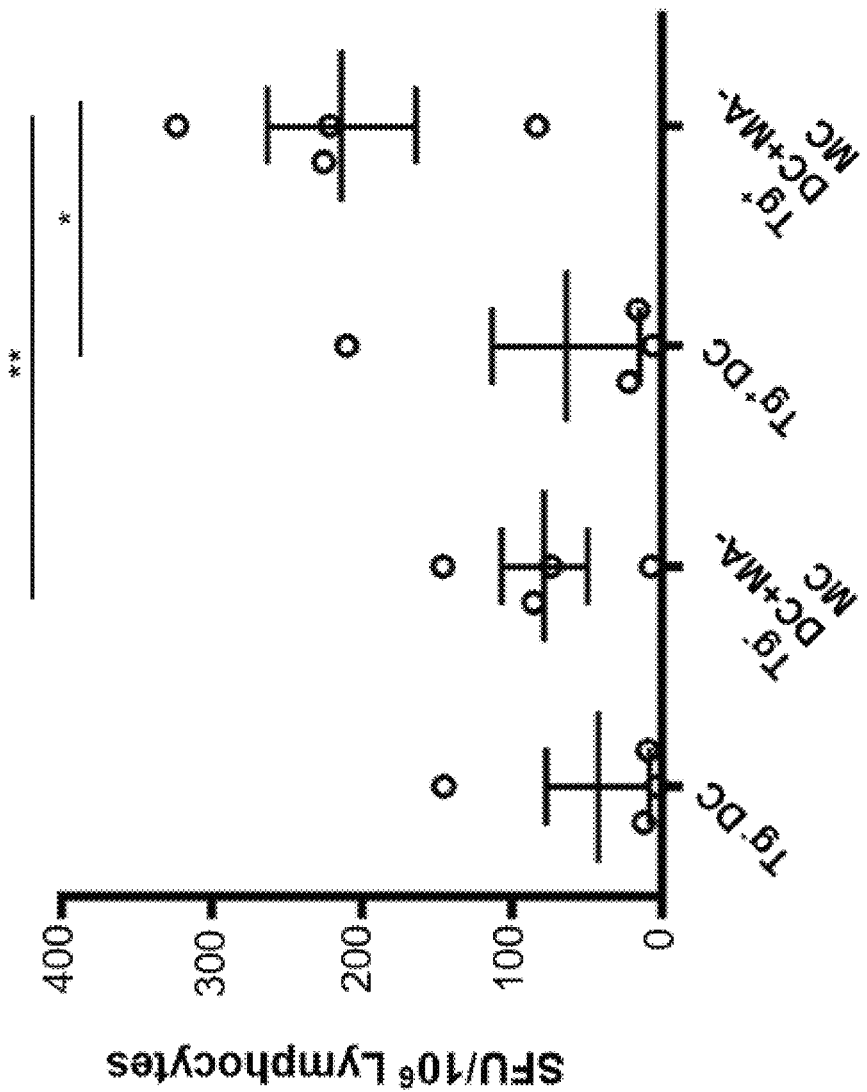
FIG. 15 shows intranasal immunization with MA-ASMc induces MA-specific T cell response in hCD1Tg CD4-deficient mice. hCD1Tg/CD4$^{-/-}$ mice (n=4) were immunized intranasally with 4 μg of MA-ASMc and sacrificed 1 week later. MA-specific, hCD1-restricted T cell response were detected in the spleen in response to re-stimulation with MA pulsed or un-pulsed hCD1Tg negative (Tg$^-$) or positive (Tg$^+$) MHC class II-deficient BMDCs in IFN-γ ELISPOT assay. *, P<0.05; **, P<0.01.

In summary, we have demonstrated that MA-MCs can elicit MA-specific T cell responses when delivered i.n. to human group 1 CD1 transgenic mice by packaging MA into a non-immunogenic micellar nanocarrier for enhanced intracellular delivery. The humanized CD1Tg mice employed here will support future experiments to evaluate the protective efficacy of MA-Mc-based subunit vaccines in Mtb challenged mice. Incorporation of lipid-antigens may enhance the efficacy of a wide range of subunit vaccine formulations and provide solutions to challenges facing current immunization strategies. For example, HIV-infected patients mostly suffer from co-infection with Mtb due to depletion of $CD4^+$ T cells (1), whereas group 1 CD1-restricted T cells are not affected by HIV infection (10, 51). In fact, in a pilot experiment, we were able to detect MA-specific hCD1-restricted T cell responses in $hCD1Tg^{+/-}$/$CD4^{-/-}$ mice immunized with MA-ASMc (FIG. 15). Thus, targeting group 1 CD1-restricted T cells by vaccination with MA-MC-supplemented vaccines could be particularly beneficial for HIV-infected individuals. Additionally, the inclusion of an immunostimulant in our MA-Mc subunit vaccines remains unexplored and may find utility in boosters to enhance immune responses elicited by established vaccines, such as Bacillus Calmette-Guerin (BCG).

REFERENCES

1. WHO. Global Tuberculosis Report 2016. Geneva: WHO Press.; 2016.
2. Beckman E M, Porcelli S A, Morita C T, Behar S M, Furlong S T, Brenner M B. Recognition of a lipid antigen by CD1-restricted alpha beta+ T cells. Nature. 1994; 372(6507):691-4.
3. Beckman E M, Melian A, Behar S M, Sieling P A, Chatterjee D, Furlong S T, et al. CD1c restricts responses of mycobacteria-specific T cells. Evidence for antigen presentation by a second member of the human CD1 family. J Immunol. 1996; 157(7):2795-803.
4. Moody D B, Ulrichs T, Muhlecker W, Young D C, Gurcha S S, Grant E, et al. CD1c-mediated T-cell recognition of isoprenoid glycolipids in *Mycobacterium tuberculosis* infection. Nature. 2000; 404(6780):884-8.
5. Kasmar A G, van Rhijn I, Cheng T Y, Turner M, Seshadri C, Schiefner A, et al. CD1b tetramers bind alphabeta T cell receptors to identify a mycobacterial glycolipid-reactive T cell repertoire in humans. The Journal of experimental medicine. 2011; 208(9):1741-7.
6. Van Rhijn I, Ly D, Moody D B. CD1a, CD1b, and CD1c in immunity against mycobacteria. Advances in experimental medicine and biology. 2013; 783:181-97.
7. Sieling P A, Chatterjee D, Porcelli S A, Prigozy T I, Mazzaccaro R J, Soriano T, et al. CD1-restricted T cell recognition of microbial lipoglycan antigens. Science (New York, N Y 1995; 269(5221): 227-30.
8. Siddiqui S, Visvabharathy L, Wang C R. Role of Group 1 CD1-Restricted T Cells in Infectious Disease. Front Immunol. 2015; 6:337.
9. Barry C E, 3rd, Lee R E, Mdluli K, Sampson A E, Schroeder B G, Slayden R A, et al. Mycolic acids: structure, biosynthesis and physiological functions. Prog Lipid Res. 1998; 37(2-3): 143-79.
10. Montamat-Sicotte D J, Millington K A, Willcox C R, Hingley-Wilson S, Hackforth S, Innes J, et al. A mycolic acid-specific CD1-restricted T cell population contributes to acute and memory immune responses in human tuberculosis infection. The Journal of clinical investigation. 2011; 121(6): 2493-503.
11. Van Rhijn I, van Berlo T, Hilmenyuk T, Cheng T Y, Wolf B J, Tatituri R V, et al. Human autoreactive T cells recognize CD1b and phospholipids. Proceedings of the National Academy of Sciences of the United States of America. 2016; 113(2):380-5.
12. Chancellor A, Tocheva A S, Cave-Ayland C, Tezera L, White A, Al Dulayymi J R, et al. CD1b-restricted GEM T cell responses are modulated by *Mycobacterium tuberculosis* mycolic acid meromycolate chains. Proceedings of the National Academy of Sciences of the United States of America. 2017; 114(51):E10956-E64.
13. Zhao J, Siddiqui S, Shang S, Bian Y, Bagchi S, He Y, et al. Mycolic acid-specific T cells protect against *Mycobacterium tuberculosis* infection in a humanized transgenic mouse model. eLife. 2015; 4.
14. Felio K, Nguyen H, Dascher C C, Choi H J, Li S, Zimmer M I, et al. CD1-restricted adaptive immune responses to Mycobacteria in human group 1 CD1 transgenic mice. The Journal of experimental medicine. 2009; 206(11):2497-509.
15. Banal D C, Brenner M B. CD1 antigen presentation: how it works. Nature reviews. 2007; 7(12):929-41.
16. Allen S, Liu Y G, Scott E. Engineering nanomaterials to address cell-mediated inflammation in atherosclerosis. Regen Eng Transl Med. 2016; 2(1):37-50.
17. Scott E A, Karabin N B, Augsornworawat P. Overcoming Immune Dysregulation with Immunoengineered Nanobiomaterials. Annu Rev Biomed Eng. 2017; 19:57-84.
18. Allen S, Osorio O, Liu Y G, Scott E. Facile assembly and loading of theranostic polymersomes via multi-impingement flash nanoprecipitation. J Control Release. 2017; 262:91-103.
19. Dowling D J, Scott E A, Scheid A, Bergelson I, Joshi S, Pietrasanta C, et al. Toll-like receptor 8 agonist nanoparticles mimic immunomodulating effects of the live BCG vaccine and enhance neonatal innate and adaptive immune responses. J Allergy Clin Immunol. 2017.
20. Scott E A, Stano A, Gillard M, Maio-Liu A C, Swartz M A, Hubbell J A. Dendritic cell activation and T cell priming with adjuvant- and antigen-loaded oxidation-sensitive polymersomes. Biomaterials. 2012; 33(26): 6211-9.
21. Stano A, Scott E A, Dane K Y, Swartz M A, Hubbell J A. Tunable T cell immunity towards a protein antigen using polymersomes vs. solid-core nanoparticles. Biomaterials. 2013; 34(17):4339-46.
22. Vasdekis A E, Scott E A, O'Neil C P, Psaltis D, Hubbell J A. Precision intracellular delivery based on optofluidic polymersome rupture. ACS nano. 2012; 6(9):7850-7.
23. Yi S, Allen S D, Liu Y G, Ouyang B Z, Li X, Augsornworawat P, et al. Tailoring Nanostructure Morphology for Enhanced Targeting of Dendritic Cells in Atherosclerosis. ACS nano. 2016; 10(12):11290-303.
24. Cenitelli S, O'Neil C P, Velluto D, Fontana A, Adrian M, Dubochet J, et al. Aggregation behavior of poly(ethylene glycol-bl-propylene sulfide) di- and triblock copolymers in aqueous solution. Langmuir. 2009; 25(19):11328-35.
25. Karabin N B, Allen S, Kwon H K, Bobbala S, Firlar E, Shokuhfar T, et al. Sustained micellar delivery via inducible transitions in nanostructure morphology. Nat Commun. 2018; 9(1):624.
26. Cenitelli S, Fontana A, Velluto D, Adrian M, Dubochet J, De Maria P, et al. Thermodynamic and kinetic effects in the aggregation behavior of a poly(ethylene glycol-b-propylene sulfide-b-ethylene glycol) ABA triblock copolymer. Macromolecules. 2005 ; 38(18): 7845-51.
27. Napoli A, Valentini M, Tirelli N, Muller M, Hubbell J A. Oxidation-responsive polymeric vesicles. Nature materials. 2004; 3(3):183-9.
28. Bobbala S, Allen S D, Scott E A. Flash nanoprecipitation permits versatile assembly and loading of polymeric bicontinuous cubic nanospheres. Nanoscale. 2018.
29. Saito G, Velluto D, Resmini M. Synthesis of 1,8-naphthalimide-based probes with fluorescent switch triggered by flufenamic acid. R Soc Open Sci. 2018; 5(6): 172137.
30. Pais V F, Remon P, Collado D, Andreasson J, Perez-Inestrosa E, Pischel U. OFF-ON-OFF fluorescence switch with T-latch function. Org Lett. 2011; 13(20):5572-5.
31. Ott I, Xu Y, Liu J, Kokoschka M, Harlos M, Sheldrick W S, et al. Sulfur-substituted naphthalimides as photoactivatable anticancer agents: DNA interaction, fluorescence imaging, and phototoxic effects in cultured tumor cells. Bioorg Med Chem. 2008; 16(15):7107-16.
32. Viader-Salvadó J. M. G-OM, Garza-Gonzalez E., Tijerina-Menchaca R. Drug Susceptibility of *Mycobacterium tuberculosis* Through the Mycolic Acid Index. Gillespie SH (eds) Antibiotic Resistance Methods in Molecular Medicine™: Humana Press; 2001.
33. Li S, Choi H J, Felio K, Wang C R. Autoreactive CD1b-restricted T cells: a new innate-like T-cell population that contributes to immunity against infection. Blood. 2011; 118(14):3870-8.
34. Lemmer Y, Kalombo L, Pietersen R D, Jones A T, Semete-Makokotlela B, Van Wyngaardt S, et al. Mycolic acids, a promising mycobacterial ligand for targeting of nanoencapsulated drugs in tuberculosis. J Control Release. 2015; 211:94-104.
35. Manjaly Thomas Z R, McShane H. Aerosol immunisation for TB: matching route of vaccination to route of infection. Transactions of the Royal Society of Tropical Medicine and Hygiene. 2015; 109(3):175-81.
36. Aguilo N, Alvarez-Arguedas S, Uranga S, Marinova D, Monzon M, Badiola J, et al. Pulmonary but Not Subcutaneous Delivery of BCG Vaccine Confers Protection to Tuberculosis-Susceptible Mice by an Interleukin 17-Dependent Mechanism. J Infect Dis. 2016; 213(5): 831-9.
37. Kawasaki N, Rillahan C D, Cheng T Y, Van Rhijn I, Macauley M S, Moody D B, et al. Targeted delivery of mycobacterial antigens to human dendritic cells via Siglec-7 induces robust T cell activation. J Immunol. 2014; 193(4):1560-6.
38. Kallert S, Zenk S F, Walther P, Grieshober M, Weil T, Stenger S. Liposomal delivery of lipoarabinomannan triggers *Mycobacterium tuberculosis* specific T-cells. Tuberculosis. 2015; 95(4):452-62.
39. Hiromatsu K, Dascher C C, LeClair K P, Sugita M, Furlong S T, Brenner M B, et al. Induction of CD1-restricted immune responses in guinea pigs by immunization with mycobacterial lipid antigens. J Immunol. 2002; 169(1):330-9.
40. Dascher C C, Hiromatsu K, Xiong X, Morehouse C, Watts G, Liu G, et al. Immunization with a mycobacterial lipid vaccine improves pulmonary pathology in the guinea pig model of tuberculosis. International immunology. 2003; 15(8):915-25.
41. Garcia Mde L, Borrero R, Lanio M E, Tirado Y, Alvarez N, Puig A, et al. Protective effect of a lipid-based preparation from *Mycobacterium smegmatis* in a murine model of progressive pulmonary tuberculosis. BioMed research international. 2014; 2014:273129.
42. Gilleron M, Quesniaux V F, Puzo G. Acylation state of the phosphatidylinositol hexamannosides from *Mycobacterium bovis* bacillus Calmette Guerin and *Mycobacterium tuberculosis* H37Rv and its implication in Toll-like receptor response. The Journal of biological chemistry. 2003; 278(32):29880-9.
43. Davidsen J, Rosenkrands I, Christensen D, Vangala A, Kirby D, Perrie Y, et al. Characterization of cationic liposomes based on dimethyldioctadecylammonium and synthetic cord factor from *M. tuberculosis* (trehalose 6,6'-dibehenate)-a novel adjuvant inducing both strong CMI and antibody responses. Biochimica et biophysica acta. 2005; 1718(1-2):22-31.
44. Larrouy-Maumus G, Layre E, Clark S, Prandi J, Rayner E, Lepore M, et al. Protective efficacy of a lipid antigen vaccine in a guinea pig model of tuberculosis. Vaccine. 2017; 35(10): 1395-402.
45. Discher B M, Won Y Y, Ege D S, Lee J C, Bates F S, Discher D E, et al. Polymersomes: tough vesicles made from diblock copolymers. Science. 1999; 284(5417): 1143-6.
46. Wendorf J, Singh M, Chesko J, Kazzaz J, Soewanan E, Ugozzoli M, et al. A practical approach to the use of nanoparticles for vaccine delivery. Journal of pharmaceutical sciences. 2006; 95(12):2738-50.
47. Cabral H, Kataoka K. Progress of drug-loaded polymeric micelles into clinical studies. J Control Release. 2014; 190:465-76.
48. Espinosa-Cueto P, Magallanes-Puebla A, Castellanos C, Mancilla R. Dendritic cells that phagocytose apoptotic macrophages loaded with mycobacterial antigens activate CD8 T cells via cross-presentation. PLoS One. 2017; 12(8):e0182126.
49. Schaible U E, Winau F, Sieling P A, Fischer K, Collins H L, Hagens K, et al. Apoptosis facilitates antigen presentation to T lymphocytes through MHC-I and CD1 in tuberculosis. Nature medicine. 2003; 9(8):1039-46.

50. Van Rhijn I, Iwany S K, Fodran P, Cheng T Y, Gapin L, Minnaard A J, et al. CD1b-mycolic acid tetramers demonstrate T-cell fine specificity for mycobacterial lipid tails. European journal of immunology. 2017; 47(9):1525-34.
51. Gong J, Stenger S, Zack J A, Jones B E, Bristol G C, Modlin R L, et al. Isolation of *Mycobacterium*-reactive CD1-restricted T cells from patients with human immunodeficiency virus infection. The Journal of clinical investigation. 1998; 101(2):383-9.

Example 2

The current global shortage of several attenuated vaccines, including Bacillus Calmette-Guerin (BCG) vaccine against TB, calls for a scalable subunit vaccine formulation that can achieve lasting immunological memory. Polymeric nanobiomaterials (NBM) are advantageous for the rational design and fabrication of subunit vaccines by increasing stability and shelf life, providing mechanisms for controlled release and delivery of diverse payloads, and allowing better control over reproducibility, speed and cost of production[6]. Furthermore, while BCG reduces the risk of disseminated TB in children[7], it is limited by inconsistent manufacturer-to-manufacturer production (e.g., BCG-Denmark vs BCG-India[8]) and ineffective protection in adults. Numerous subunit vaccines have attempted to improve upon BCG, primarily focusing on eliciting MHC-restricted conventional T cell responses to Mtb protein antigens, such as TB10.4, ESAT6, Ag85A, and Ag85B[9,10]. Several of these vaccines have undergone clinical testing but failed to generate effective protection, suggesting a need to identify alternative strategies[11-13].

Incorporation of lipid antigens into subunit vaccines—Bacteria contain distinct antigens in addition to proteins (e.g. lipids, glycolipids, vitamin B metabolites) that are recognized by unconventional T cells but have not been evaluated as candidates for subunit vaccines[3,14-16]. As a result, attenuated bacterial vaccines can elicit broad immune responses against both lipid and protein components, while current subunit vaccine strategies lack lipid-specific mechanisms of immunity. CD1 antigen presenting molecules present lipid antigens to T cells. In humans, the CD1 family consists of group 1 CD1 molecules CD1a, CD1b, and CD1c, and the group 2 CD1 molecule CD1d. Mice lack group 1 CD1, but express group 2 CD1. Among four CD1 isoforms, CD1b presents the largest pool of Mtb-derived lipids to cognate T cells, including mycolic acid (MA), glucose monomycolates (GMM) and diacylated sulfoglycolipids (SGL)[17]. Unlike MHC, CD1 molecules are nonpolymorphic, so immunotherapies incorporating CD1-restricted T cells may have more uniform responses across the human population[18]. Studies in humans have shown that many TB patients had IFN-γ-producing, MA-specific CD1b-restricted T cells at disease sites and in their blood[19], suggesting MA is an immunodominant lipid antigen ideal for incorporation into multicomponent subunit vaccines. However, due to difficulties in the controlled delivery of lipid antigens as well as a lack of suitable mouse models, targeted activation of group 1 CD1-restricted T cells has been largely absent from immunotherapeutic strategies in vivo. The more biomimetic simultaneous activation of 1) unconventional lipid-specific CD1-restricted T cells and 2) conventional protein-specific MHC-restricted T cells may significantly improve subunit vaccine efficacy.

Figure 16:
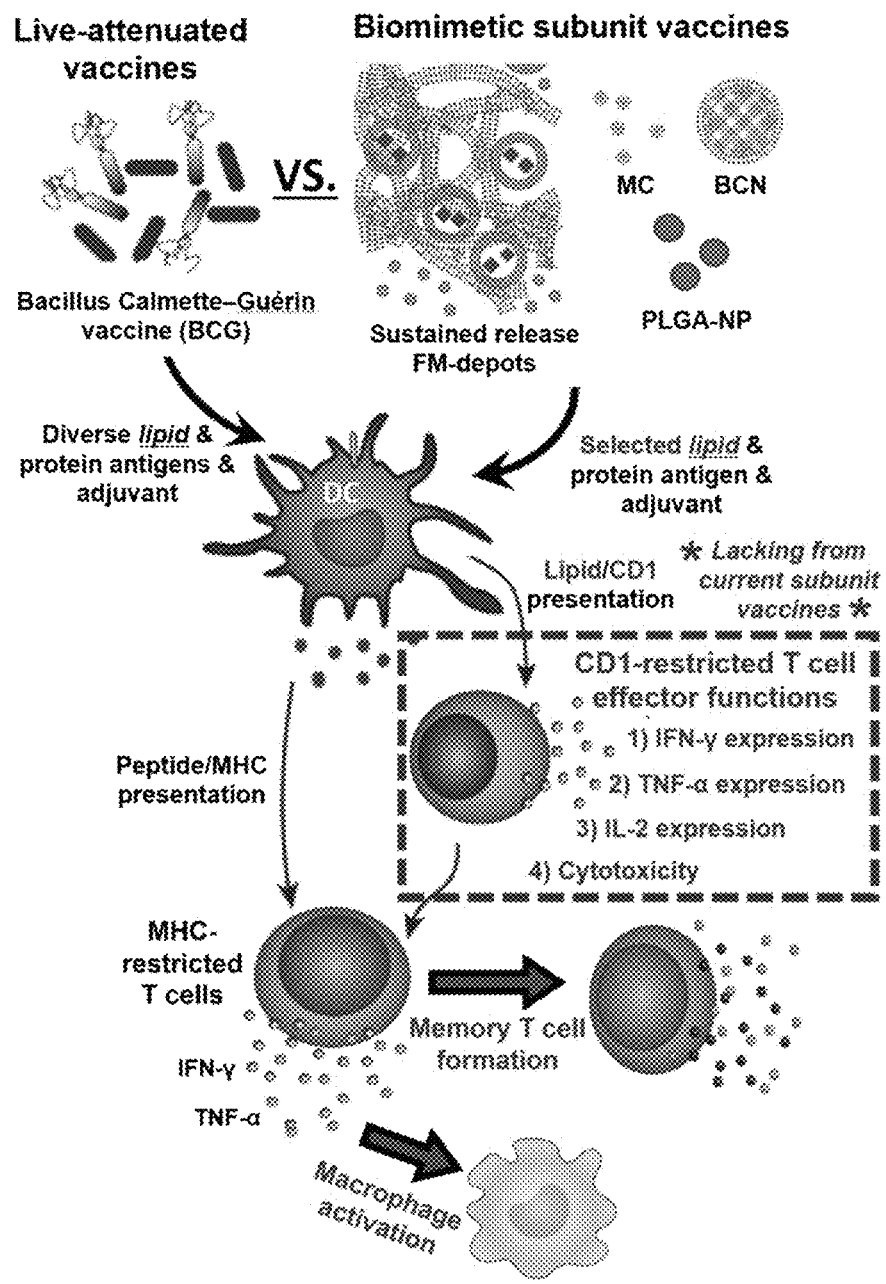
FIG. 16 shows a biomimetic NBM strategy for subunit vaccination. By mimicking the molecular composition and release duration of live-attenuated vaccines, NBM delivery systems will activate both CD1- and MHC-restricted T cells. Current subunit vaccines lack critical responses elicited by lipid antigens.

Adjuvant selection for CD1-restricted T cell activation—Several beneficial responses elicited by attenuated vaccines are not observed during subunit vaccination, including heterologous "training" of innate immune cells and improved memory T cell generation (FIG. 16). The responses of activated CD1-restricted T cells include cell-mediated killing and systemic increases in cytokines such as IL-2, TNF-α, and IFN-γ[20]. Cytokines produced by CD1-restricted T cells elicit critical immunological responses that include the stimulation and enhancement of MHC-restricted T cell function[20]. Although conditions for inducing MHC-restricted T cell responses have been well studied[21,22], optimal immunization conditions and adjuvant combinations to elicit CD1-restricted T cell responses have not been determined. Importantly, immunostimulation by some adjuvants has been shown to promote the activation of CD1-restricted autoreactive T cells[23-26]. Thus, it is critical to determine which adjuvant combinations as well as which NBM can promote T cell responses specifically against bacterial lipid (foreign) antigens but not self-lipids.

Activation of CD1-restricted T cells requires efficient intracellular delivery of lipid antigens to endosomal compartments of antigen presenting cells (APC), mainly dendritic cells (DC), for complexation with CD1 molecules and trafficking to the cell surface. Using NBM engineered for targeted intracellular delivery to APC, we will improve subunit vaccines by better mimicking mechanisms of live attenuated pathogens. Presented herein are adjuvant formulations for simultaneous elicitation of CD1b- and MHC-restricted T cell responses from a subunit vaccine. The role of CD1b-restricted T cells in controlling Mtb infection and the failure of subunit vaccines against TB are well documented, presenting an advantageous model to demonstrate the utility of unconventional T cells and engineered NBM vaccines.

We have developed unique scalable methods for rapid fabrication and drug loading of poly(ethylene glycol)-b-poly(propylene sulfide) (PEG-b-PPS) NBM that can mimic live-attenuated vaccines[27,28]. PEG-b-PPS is non-adjuvanting, allowing our nanocarriers to function as "blank slates" with an immunostimulatory potential based solely upon the selected molecules loaded inside[28,29]. In addition, we have recently found that PEG-b-PPS NBM can transport poorly water-soluble lipids derived from Mtb, like MA, that previously presented considerable challenges for targeted delivery[2]. Since the incorporation of MA and other Mtb lipids into subunit vaccines remains poorly characterized, we employ novel NBM delivery systems to assess the optimal nanostructures, adjuvant formulation and release kinetics for stimulating MA-specific CD1b-restricted T cells in vivo. The amount and duration of antigen/adjuvant exposure has a critical impact on the elicited immune response[30], and thus synthetic systems designed for controlled delivery of therapeutics are ideal platforms for such studies. Below are our key innovations in controlled vaccine delivery that are critical to this study.

Figures 17A, 17B, 17C, 17D, 17E, 17F, 17G, 17H, 17I, 17J, 17K:
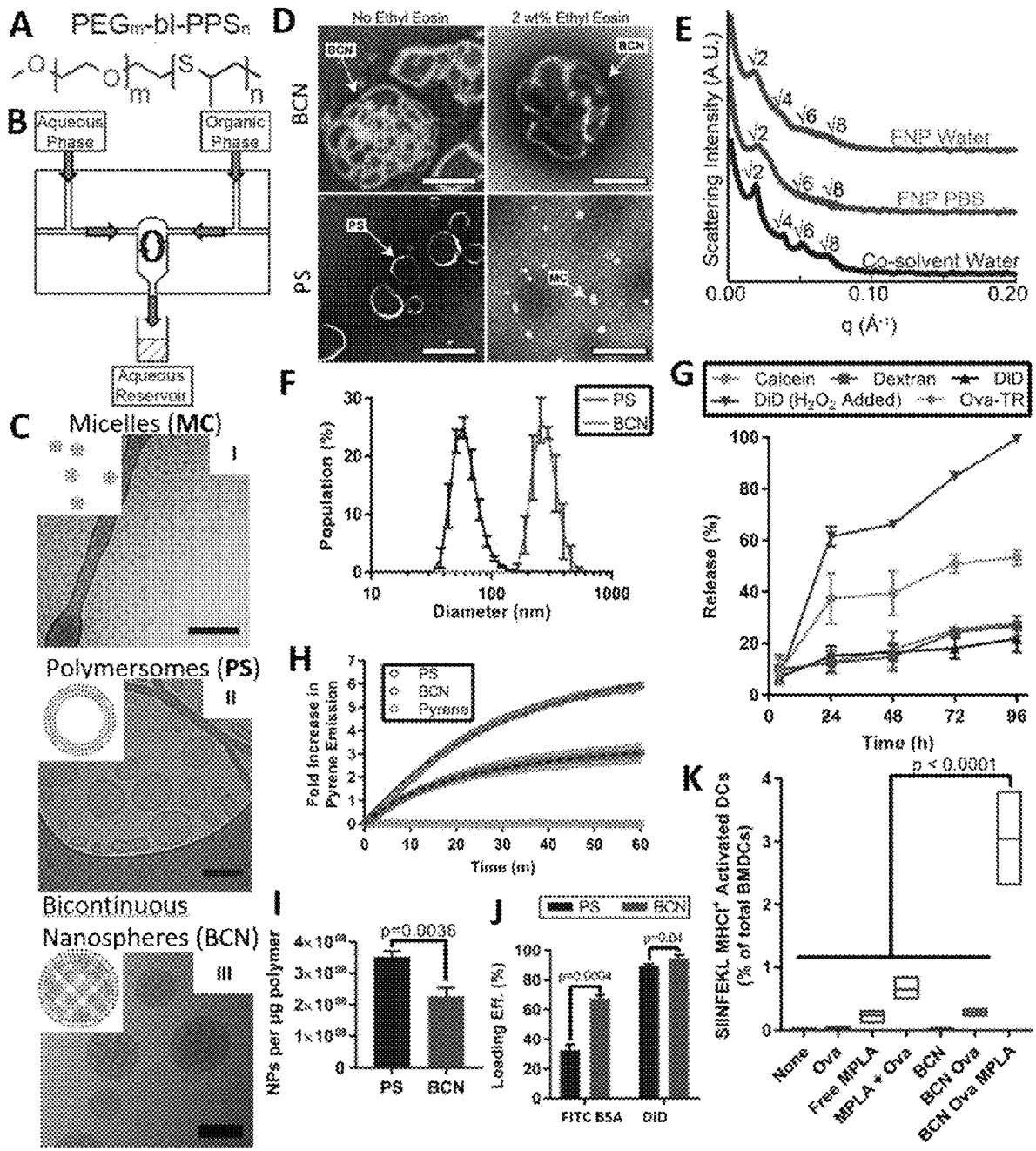
FIGS. 17A-17K show a scalable, low cost NBM vaccine delivery system & methods of characterization. Rapid, scalable self-assembly of (FIG. 17A) PEG-b-PPS via (FIG. 17B) flash nanoprecipitation into (FIG. 17C) diverse nanostructures. CryoEM images of nanostructures are shown. Scale bars=100 nm.

Rapid, scalable assembly and loading of bioactive proteins and immunostimulants into diverse synthetic subunit vaccines via flash nanoprecipitation. We are the first to use flash nanoprecipitation for scalable assembly of NBM for vaccine delivery (FIGS. 17A-17C) (27, 31). Our protocols employ confined impingement jets mixers (32), for customizable self-assembly of PEG-b-PPS copolymers into nanostructures that mimic common viral/bacterial morphologies: solid-core spherical micelles ($PEG_{45}$-b-$PPS_{29}$, MC), vesicular polymersomes ($PEG_{17}$-b-$PPS_{30}$, PS), and bicontinuous nanospheres ($PEG_{17}$-b-$PPS_{75}$, BCN) (FIG. 17C). Advantages of the PEG-b-PPS nanocarrier system include rapid gram-scale fabrication(27, 33), stability for months to years when loaded with antigen and adjuvant[28], high loading efficiency for protein antigens (~70% for albumin) and small molecule adjuvants (>90% for imiquimod derivatives) (27, 28), redox-sensitivity for intracellular delivery and enhanced antigen cross presentation (27-29, 33-37), morphology-dependent targeting of APC(38), amenability to multimodal imaging (28, 29, 34, 35, 39), and controllable immunostimulation whencombining molecular payloads (29, 35, 40).

Of note, both hydrophilic and hydrophobic payloads can be simultaneously encapsulated in PS and BCN using flash nanoprecipitation (1, 33). PS are vesicular structures with hydrophobic membranes and aqueous lumens for respective retention of lipophilic water-soluble payloads. PS are generally acknowledged as being more stable and versatile vesicular nanocarriers than liposomes (41-43). BCN possess extensive bicontinuous hydrophobic domains interspersed with ordered aqueous channels (FIGS. 17C and 17D) (44). As verified by cryogenic (cryoEM) and transmission electron microscopy (FIGS. 17C and 17D), small-angle X-ray scattering (SAXS) (FIG. 17E), and dynamic light scattering (DLS) (FIG. 17F), flash nanoprecipitation is currently the only means of scalable fabrication of monodisperse BCN (27, 33). SAXS scattering profile of BCN showed Bragg peaks with relative spacing ratios at √2, √4, and √6, indicating the presence of primitive type (Im3m) cubic internal organization (1, 33). Similar to PEG-b-PPS PS (29, 34, 39, 45), BCN can release their diverse hydrophilic and lipophilic payloads in response to physiological levels of reactive oxygen species (FIG. 17G). We recently benchmarked BCN against PS (1), concluding that BCN can load more hydrophobic payload without disrupting their self-assembled structure (FIG. 17D), have a higher total capacity to load hydrophobic payloads per mass of polymer (FIG. 17H) possibly due to a higher density of PPS per particle (FIG. 17I) and have a significantly higher encapsulation efficiency for both hydrophilic and hydrophobic cargo (FIG. 17J). During vaccination, BCN payloads release within the endosomes of APC (29, 33, 35, 39, 46), where antigen loading to MHC II and CD1 occurs (47). An in vitro functional assay showed BCN co-loaded with antigen ovalbumin and adjuvant monophosphoryl lipid A (MPLA) to promote peptide/MHC I presentation by DC, a critical step for vaccines during immunization (FIG. 17K).

PEG-b-PPS FMs can be crosslinked into hydrogel depots for sustained delivery of drug-loaded NBM. We synthesized crosslinkable vinyl sulfone end-functionalized copolymers (VS-PEG-b-PPS) to form injectable filamentous hydrogel drug depots (FM-depots) (48). FM-depots support the sustained retention and delivery of drug-loaded NBM via a novel method referred to as the cylinder-to-sphere transition, wherein the synthetic filaments that comprise the scaffold reassemble into drug-loaded MC vehicles (FIGS. 18A-18B) (48). Instead of intermittent bolus injections of therapeutics and/or NBM, FM-depots require only a single injection and locally generate drug-loaded MC in situ at the site of injection (analogous to viruses budding from the lipid membranes of cells). The time course of release for fluorescently tagged MC (Dylight 633 & 755) loaded with DiI as a model drug was verified to occur reproducibly for 28 days following injection to mice (FIGS. 18C-18D). Mice receiving FM-depots exhibited significantly greater cellular uptake within the draining lymph nodes and spleen than those receiving free Dylight or non-crosslinked FMs (FIG. 18E). These results demonstrate that FM-depots can sustainably deliver drug-loaded MC to APC in lymphoid organs (48).

Figures 19A, 19B:
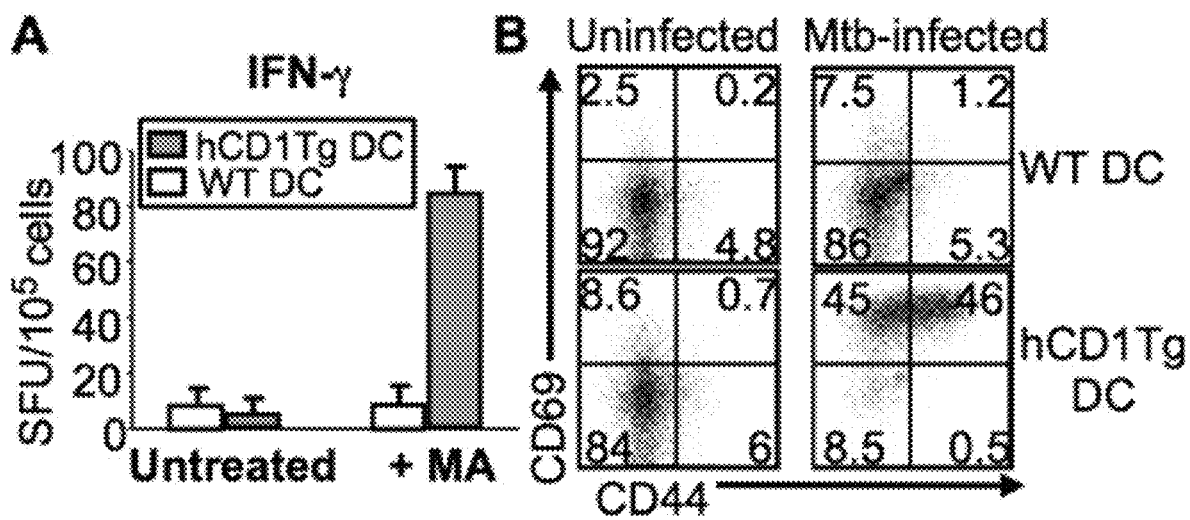
FIGS. 19A-19B show DN1 T cells acquire effector functions in response to MA-pulsed DC and Mtb-infected DC.

Novel animal models to assess group 1 CD1-restricted T cell function and activation. To overcome the lack of group 1 CD1 in mice, we have generated a novel transgenic mouse model that expresses the human group 1 CD1 genes under their endogenous promoter (49). Human group 1 CD1 transgenic (hCD1Tg) mice express CD1a, CD1b, and CD1c in a pattern similar to that seen in humans and support the development of group 1 CD1-restricted T cells (49, 50). To facilitate direct analysis of the group 1 CD1-restricted T cell responses, we generated a transgenic mouse strain (DN1Tg) that expresses a TCR specific for MA/CD1b (51). DN1Tg mice were bred onto the hCD1Tg/Rag$^{-/-}$ background to support the development of DN1 T cells and eliminate expression of endogenous TCR (52). DN1 T cells produced IFN-γ in response to MA-pulsed hCD1Tg DC but not WT DC or un-pulsed DC (FIG. 19A), suggesting activation of DN1 T cells requires both antigen and group 1 CD1 molecules. Co-culture of DN1 T cells with Mtb-infected hCD1Tg DC led to upregulation of CD69 and CD44 on T cells (FIG. 19B), indicating that DN1 T cells can be activated by naturally processed MA. Our use of the CD1b/MA-specific TCR transgenic mouse model parallels standard protein antigen validation and optimization via the ovalbumin/OTI and OTII mouse models, and thus we present a new standard methodology for assessing and optimizing vaccine strategies for lipid antigens.

Due to their hydrophobic nature, it is difficult to controllably deliver lipid antigens for vaccination purposes. Exposure of lipids to biological fluids will immediately result in their binding to albumin, HDL and other lipid carriers, which will transport them to either non-specific or unintended cells and organs. While lipids have been successfully loaded within PLGA-based nanoparticles, these nanocarriers may not be ideal for controlled stimulation of CD1-restricted T cells as a substantial number of CD1-restricted T cells display some degree of autoreactivity (53, 54). Naked PLGA-based nanoparticles are known to have immunostimulatory (55) as well as tolerogenic (56) responses in the absence of adjuvant that are not fully understood (57). We have generated data demonstrating that this intrinsic adjuvant effect results in non-specific self-lipid responses from CD1-restricted T cells stimulated by DC pulsed with standard 100 nm naked PLGA nanoparticles. Below, we outline our rationale for BCN as a solution for controllable transport and targeting of lipid antigens to desired APC populations during vaccination, with validation using custom tetramers in hCD1Tg mice.

BCN as NBM for biomimetic vaccines containing both lipid and protein antigen.—The ideal synthetic NBM for subunit vaccines would be amenable to: i) stable loading and transport of both hydrophilic and lipophilic, small and macromolecules, ii) scalable fabrication without modulating the chemistry or structure of payloads, and iii) intracellular delivery to endosomes and cytosol of APC. Of critical importance for antigen presentation by MHC and CD1 molecules is the ability to stably retain payloads within vehicles without chemical modification. Having verified PEG-b-PPS MC for effective lipid antigen delivery, we sought to scalably fabricate a more versatile PEG-b-PPS nanostructure to serve as the basis for a subunit vaccine formulation capable of dual delivery of lipid and protein antigen. Unlike MC, the aqueous core of PS and porous cubic phase structure of BCN are both well suited for dual delivery of hydrophilic and lipophilic payloads without chemical modification or conjugation. We have previously published peptide-based vaccine delivery via PS (28, 29, 34) and BCN (33) for conventional T cell activation. The larger hydrophobic volume of BCN should stably retain more lipophilic payload than the thin (8-10 nm) membranes of PS, while simultaneously loading hydrophilic protein antigen.

Employing human CD1 transgenic mouse models and CD1 tetramers to optimize and evaluate biomimetic subunit vaccines for TB—Research into group 1 CD1 molecules have been mainly limited to guinea pig and bovine models that have limited antibody options for detailed flow cytometric analysis (18, 58, 59). The hCD1Tg mouse model possess human CD1a, b, c, and e molecules, as well as normal mouse CD1d molecules and NKT cell responses.

To investigate loading and transport of lipid antigens via the PEG-b-PPS system, we designed and synthesized the block-copolymer $PEG_{44}$-b-$PPS_{14}$ incorporating a novel acid-sensitive fluorophore derived from 1,8-naphthalamide ($\lambda exc=395$ nm, $\lambda em=505$ nm) (60). This copolymer assembles into the simplest nanostructure, spherical MC, which we loaded with the model lipid antigen MA (MA-MC) (FIG. 1A). MA-MC were amenable to intranasal delivery and enhanced CD1b-restricted T cell recruitment to the lung, which is advantageous for using TB infection as a model for investigating and optimizing subunit vaccines incorporating lipid antigens.

MA-loaded MC have a superior efficacy over free MA in activating CD1b-restricted MA-specific TCR transgenic (DN1) T cells. CryoTEM and DLS measurements showed that MA-MC were about 68 nm in diameter with a Zeta potential of −16.5, comparable to the parameters of vehicle micelles (V-MC). To compare the efficacy of MA-MC with that of free MA in activating MA-specific T cells, hCD1Tg$^+$ BMDC were pulsed with various concentrations of free MA or MA-MC, then co-cultured with CD1b-restricted MA-specific TCR transgenic DN1 T cells for 24 h. The expression of activation markers (CD69 and CD25) and production of IFN-γ by DN1 T cells were then determined by flow cytometry and ELISA, respectively. We found that while DC pulsed with free MA could activate DN1 T cells, as reflected by CD69 and CD25 upregulation and IFN-γ production (FIGS. 4A-4B), 50- to 100-fold lower concentrations of MA were required to activate DN1 T cells when MA was delivered via MA-MC. In contrast, DC pulsed with empty V-MC did not activate DN1 T cells.

Intranasal delivery of MA-MC induces proliferation and activation of adoptively-transferred MA-specific T cells—It has been shown that optimal protection against Mtb infection is achieved when the BCG vaccine is administered directly to the pulmonary mucosa (61, 62). Therefore, we intended to induce Mtb lipid-specific T cell responses in the lung using pulmonary delivery of MA-MC via intranasal (i.n.) immunization. We first determined the biodistribution of MA-MC following i.n. delivery. We found that MA-MC were selectively taken up by a population of CD11c$^+$ cells in the lung, mostly alveolar macrophages (CD11c$^+$CD11b$^-$) and a small percentage of myeloid DC/interstitial macrophages (CD11b$^+$CD11c$^+$) (data not shown). We next performed antigen presentation assays to determine whether MA-MC can activate DN1 T cells in vivo. Celltrace violet-labeled DN1 T cells were adoptively transferred into hCD1Tg mice followed by i.n. immunization with MA-MC. At day 6 post-immunization, we determined the proliferative capacity and activation status of DN1 T cells in the lung and mediastinal lymph node (MLN) by FACS. Compared to mice immunized with unloaded micelles (V-MC), mice immunized with MA-MC had a higher percentage of DN1 T cells in both the MLN (FIG. 30A) and lung (data not shown). In addition, DN1 T cells in MA-MC-immunized mice underwent extensive proliferation (FIG. 30B) and were more activated, with a higher percentage having CD44$^{hi}$ and CD69 expression compared to those in V-MC-immunized mice (FIG. 30C). Intranasal delivery of MA-MC leads to APC presentation of MA and subsequent activation of MA-specific T cells in vivo.

Figure 20:
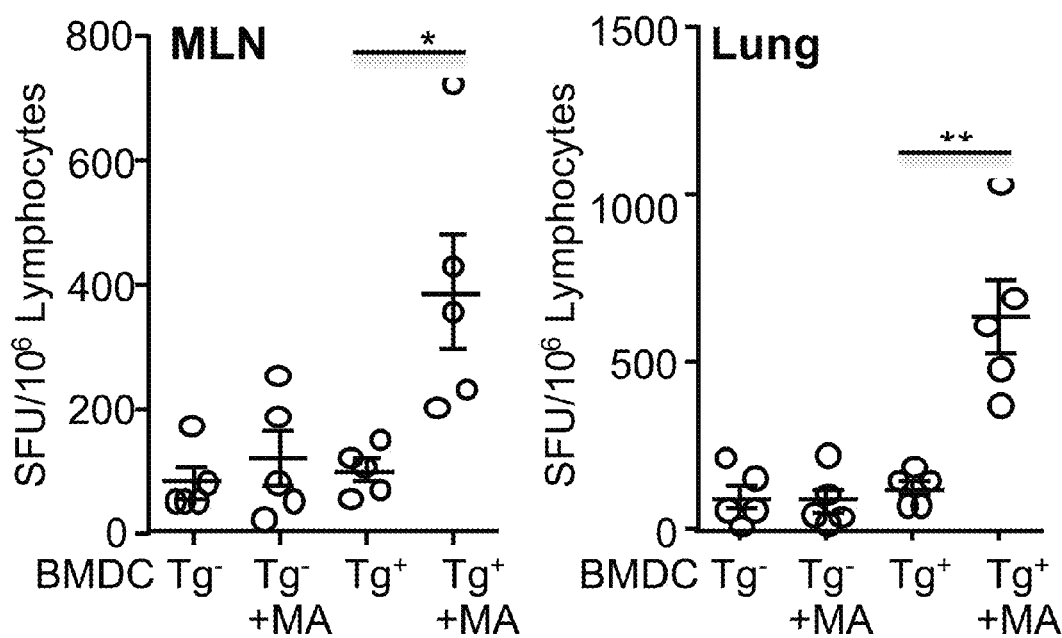
FIG. 20 shows MA-specific T cell responses are induced by intranasal immunization with MA-MC. Lymphocytes from the lung and MLN of MA-MC immunized hCD1Tg mice (N=5) were stimulated with WT (Tg) and hCD1Tg$^+$ DC, IFN-γ-secreting cells were quantitated in an ELISPOT assay. *, p<0.05; **, p<0.01.

To determine if MA-MC immunization could induce polyclonal MA-specific T responses in the lung, we immunized hCD1Tg mice i.n. with MA-MC. At day 7 post-immunization, lymphocytes were isolated from the lung and MLN of MA-MC-immunized mice and stimulated in vitro with MA-pulsed or unpulsed BMDCs from hCD1Tg (Tg$^+$) or Tg$^-$ mice. IFN-γ-producing MA-specific T cells were quantified by ELISPOT assays. We found that a significantly higher number of lymphocytes from immunized hCD1Tg mice produced IFN-γ when stimulated with MA-pulsed Tg$^+$ DC compared to stimulation with MA-pulsed Tg$^-$ DCs or unpulsed DCs (FIG. 20). Intranasal delivery of MA-MC efficiently elicits group 1 CD1-restricted MA-specific T cell responses in the lung of hCD1Tg mice.

We aim to explore the efficacy of synthetic subunit vaccines incorporating lipid antigens in addition to protein antigens, which mimics immunostimulation during vaccination with live attenuated pathogens. A notable advantage of lipid-antigens is the lack of polymorphism between CD1 molecules in the human population. This means that all humans will respond similarly to the same lipid antigens presented by CD1, in contrast, different peptide antigens are presented by highly polymorphic MHC molecules. This also suggests that any induced autoreactivity will be observed across all individuals, and thus activation of T cells against self-lipid antigens must be avoided. We have demonstrated that MA-loaded PEG-b-PPS micelles can elicit potent CD1-restricted antigen-specific T cell responses in hCD1Tg mice (2). Furthermore, we have shown that BCN have the greatest potential as a dual lipid/protein antigen delivery system compared to other PEG-b-PPS nanostructures[1]. Here, we aim to incorporate MA as well as Ag85B, an immunodominant Mtb protein used in several TB vaccine candidates, into BCN to characterize dual CD1- and MHC-restricted T cell activation. The extensive hydrophobic content within the bicontinuous mesophase of BCN is particularly suitable for incorporation of lipid immunostimulants like MA and MPLA but has never been tested for this application due to difficulties in reproducible fabrication, which we have addressed with a novel flash nanoprecipitation protocol (FIGS. 17A-17K) (33). BCN will be benchmarked against standard PLGA-NP. While both BCN and PLGA-NP can load MA and improve activation of CD1b-restricted T cells in vitro, PLGA-NP demonstrate a strong intrinsic adjuvancy that results in DN1 T cell activation in the absence of exogenous lipid antigen, MA (FIGS. 21A-21D). This apparent autoreactivity is likely due to increased costimulatory signals/proinflammatory cytokine production by DC in response to PLGA (55, 63). As such, self-lipid/CD1 complex is sufficient to trigger certain level of T cell activation. The superior loading efficiency and lack of intrinsic adjuvant effects will allow BCN to better balance the efficacy and safety of lipid-specific T cell activation. Diverse adjuvants along with MA and Ag85B will be loaded into both BCN and PLGA-NP for high throughput optimization. Each formulation will be assessed in vitro for Ag85B- and MA-specific T cell stimulation. These adjuvants will be selected based upon their ability to stimulate MA-specific T cell responses while avoiding autoreactivity. Optimized BCN and PLGA-NP formulations will be validated in vivo via intranasal administration to hCD1Tg mice to elicit MA-Ag85B-specific T cell responses in the lung.

Figures 21A, 21B, 21C, 21D:
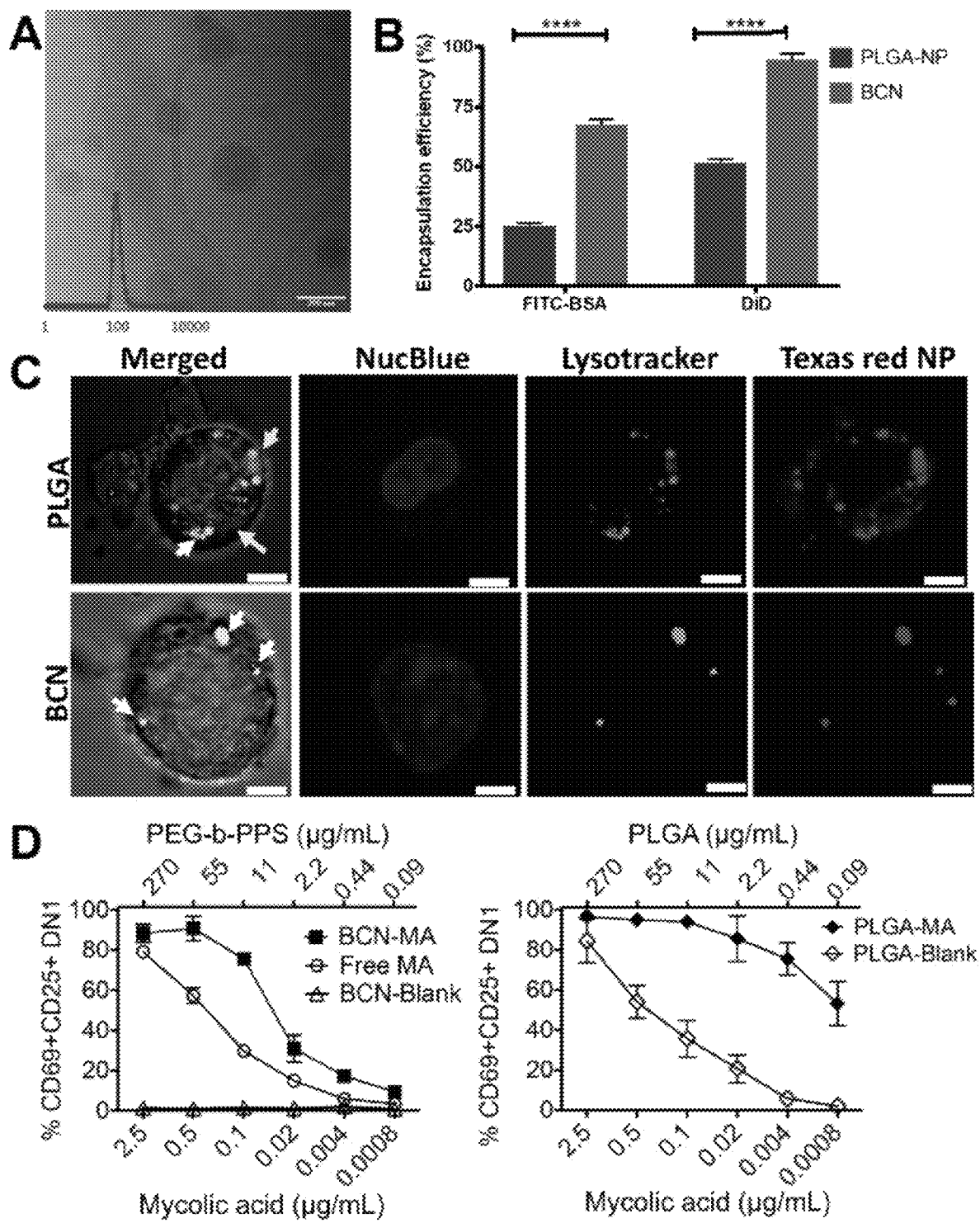
FIGS. 21A-21D show PEG-b-PPS BCN, but not PLGA-NP, demonstrate no sign of intrinsic adjuvant effect during activation of DN1 T cells.

PEG-b-PPS BCN, but not PLGA-NP, demonstrate no sign of intrinsic adjuvant effect during activation of DN1 T cells—To benchmark BCN, we synthesized 100 nm diameter COOH-terminated PLGA-NP commonly used for vaccine formulations using a standard double emulsion method as previously reported (64-66) (FIG. 21A). BCN formed by flash nanoprecipitation demonstrated significantly higher loading of both a model protein and hydrophobic payloads (FIG. 21B). Gram scale amounts of BCN were synthesized, loaded and purified within 1 h, while 6-8 h was required to form similar amounts of PLGA-NP. Incubation of the PLGA-NP with macrophages resulted in endosomal uptake followed by rapid endosomal escape as previously reported (67) (FIG. 21C). In contrast, BCN remained exclusively within endosomes (the key location of lipid antigen loading into CD1) for 8 h with no detectable endosomal rupture (FIG. 21C). MA was loaded into both BCN and PLGA-NP at the same concentration (9 μg MA/mg polymer) to assess DN1 T cell activation by NBM-pulsed DCs, with and without loaded MA. All samples were thoroughly verified to be endotoxin free (<0.05 EU/mL) using both the PYROGENT™ Gel Clot LAL Assay and TLR4 activation HEK-Blue LPS detection assays as previously demonstrated (28, 39, 68). BCN demonstrated effective delivery of MA for enhanced DN1 T cell activation compared to free form MA (FIG. 21D). Results were similar to but less potent than MA-MC (FIGS. 4A-4B), likely due to the larger size of BCN (250 nm vs. 20 nm), resulting in less particles per volume at the same polymer concentration. Importantly, blank BCN without MA demonstrated no sign of adjuvant effects at all concentrations tested. In comparison, PLGA-NP induced excellent DN1 T cell activation in vitro, but this potency was accompanied by considerable non-specific DN1 T cell activation (FIG. 21D). Blank PLGA-NP actually activated DN1 T cells at similar levels as free form MA. These data demonstrate significant differences between PEG-b-PPS BCN and PLGA-NP for fabrication scalability, nanostructure, and endosomal release.

Figure 22:
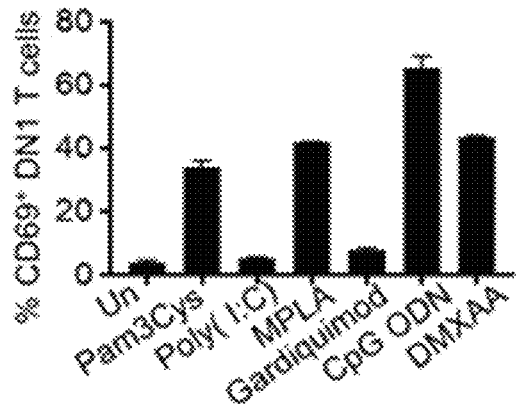
FIG. 22 shows the effect of TLR agonists and STING ligand on the stimulatory capacity of MA-MC in vitro. hCD1Tg$^+$ DC were treated with suboptimal dose of MA-MC and various TLR agonists or STING ligand (DMXAA) prior to co-culture with DN1 T cells. 24 h later, the percentage of DN1 T cells expressing CD69 was determined by FACS. Data are representative of two experiments.

NBM synthesis and loading with adjuvant and antigens—To determine the optimal adjuvant combinations to induce combined MA/CD1b- and Ag85B/MHC-specific T cell responses by NBM, we will load three adjuvants into BCN and PLGA-NP: TLR4 agonist MPLA, TLR9 agonist CpG and STING ligand cyclic-di-GMP (c-di-GMP) (69), known to enhance the systemic and mucosal Th1 response. We have performed a screen of 6 common adjuvants to identify these top three candidates for their enhancement of a suboptimal dose of MA-MC (FIG. 22). Synthesis of $PEG_{17}$-b-$PPS_{75}$ will be completed as previously described (27, 29, 39, 46). Briefly, copolymers will be synthesized via living ring-opening polymerization of propylene sulfide initiated by methoxy-PEG-thioacetate in the presence of sodium methoxide. All polymers will be characterized by NMR and gel permeation chromatography. Adjuvants will be loaded individually and in combinations into BCN with MA and Ag85B using flash nanoprecipitation (29, 34, 46, 70). Loading within PLGA-NP will be performed using previously published double emulsion methods for loading multiple hydrophilic and hydrophobic vaccine payloads (71, 72). Purified recombinant Ag85B will be obtained through BEI Resources (NIAID, NIH). MA from Mtb will be purchased from Sigma. MA/Ag85B/adjuvant-loaded NBM will be purified by tangential flow filtration and size exclusion chromatography. Loading of MA, Ag85B and adjuvants will be quantified by HPLC with UV/Vis and corona charged aerosol detectors as we have previously published (27-29, 33, 73). NBM size and structure will be respectively verified by DLS/NanoSight and cryoEM/SAXS. All samples will be a verified to be endotoxin free as previously described (28, 39, 68).

In vitro assays to assess T cell responses to various NBM formulations—To assess T cell responses to NBM formulations, BMDC incubated with BCN and PLGA-NP loaded with MA/Ag85B and different combinations of adjuvants (Table 2) will be used to stimulate T cells specific for MA/CD1b (DN1) and $Ag85B_{280-294}$/I-$A^b$ (P25) (74) for 24-48 h. Antigen-specific cytokine production will be determined by multiplex-cytokine bead arrays while NBM uptake by APC and activation status of APC (CD80, CD86 expression) and T cells (CD25, CD44, and CD69 expression) will be assessed by flow cytometry. NBM formulations will be tested at a low, medium and high concentration of adjuvants and benchmarked against MA-MC. Concentration ranges for each adjuvant will be selected based on their most common use in the literature. Multiplex analysis will be performed using a customized Milliplex® Magnetic Bead Panel to quantify levels of cytokines known to be critical for anti-Mtb immunity and T cell stimulation: IFN-γ, TNF-α, IL-2, IL-9, IL-10, IL-12 (p70), IL-1β, IL-23, IL-27, IL-33, and IL-6. The objective is to identify adjuvant combinations that enhance both CD1- and MHC-restricted T cell responses and define the quality of such responses. Optimal adjuvant combinations will be identified by the ability to significantly enhance either or both MHC- or CD1b-restricted T cell activation without increasing T cell activation in the absence of antigens. Samples PLGA9/BCN9 through PLGA12/BCN12 (Table 2) will assess self-lipid T cell responses, since they contain no MA/Ag85B antigens.

TABLE 2

Antigen/adjuvant-loaded NBM combinations

| NC formulations | MA/Ag85B | c-di-GMP | MPLA | CpG |
|---|---|---|---|---|
| PLGA1 & BCN1 | x | | | |
| PLGA2 & BCN2 | x | x | | |
| PLGA3 & BCN3 | x | | x | |
| PLGA4 & BCN4 | x | | | x |
| PLGA5 & BCN5 | x | x | | x |
| PLGA6 & BCN6 | x | | x | x |
| PLGA7 & BCN7 | x | x | x | |
| PLGA8 & BCN8 | x | x | x | x |
| PLGA9 & BCN9 | | x | | |
| PLGA10 & BCN10 | | | x | |
| PLGA11 & BCN11 | | | | x |
| PLGA12 & BCN12 | | x | x | x |

Identify optimal NBM for combined MA- and Ag85B-specific T cell responses in vivo—We have demonstrated that both morphology and composition can modulate NBM biodistributions in vivo (27, 39, 46), which cannot be determined by in vitro assays. Therefore, the most promising BCN and PLGA-NP formulations will be compared for their elicitation of MA- and Ag85B-specific T cell responses in lung, MLN, and spleen. Each NBM structure will be loaded with the identified adjuvant combinations at low, medium and high concentration. Furthermore, each NBM will be covalently tagged with DyLight 633 and DyLight 755 for multimodal analysis respectively by flow cytometry and near infrared fluorescence (NIRF) imaging, allowing assessment of changes in biodistribution of the NBMs at both the cellular and organ level as we have previously performed (27, 39, 75). We will perform in vivo antigen presentation assays via adoptive transfer of CFSE-labeled DN1Tg and CellTrace Violet-labeled P25Tg T cells to hCD1Tg mice, followed by intranasal immunization with optimal MA/Ag85B/adjuvant-loaded BCN and PLGA NP. Proliferative capacity and activation status of DN1Tg and P25Tg T cells will be determined by flow cytometry. This approach will determine the most effective NBM and adjuvant dose for in vivo activation of MA- and Ag85B-specific T cells.

Characterize T cell and antibody responses in MA-Ag85B NBM vaccinated hCD1Tg mice—To characterize polyclonal T cell responses induced by adjuvanted MA-Ag85B NBM, hCD1Tg mice will be immunized three times at two-weekly intervals with the optimal NBM and adjuvant concentration identified above. 1, 2, or 4 wks following the final immunization, the frequency of IFN-γ-producing MA- and Ag85B-specific T cells in the lung, MLN and spleen will be quantified by IFN-γ ELISPOT assay as described in preliminary studies. In addition, intracellular cytokine staining for IL-2, TNF-α, and IFN-γ will be performed to identify polyfunctional T cells using MA- and Ag85B-pulsed BMDCs as stimulators. Further, cytokine bead arrays will be used to measure other cytokines (e.g. IL-17A, IL-23, IL-22, IL6, GM-CSF) produced by MA- and Ag85B-specific T cells from immunized hCD1Tg mice. Emerging evidence suggests a role for vaccination-induced antibodies in protection against Mtb (76). Thus, we will also investigate the serum antibody response following MA-Ag85B NC immunization. At weeks 1, 2, or 4 post-boost, serum antibody titers and Ig isotype (IgM, IgG1, IgG2a/c, IgG2b, IgG3 and IgA) for MA and Ag85B will be determined by ELISA.

The pulmonary route of exposure, by which most TB patients acquire their primary infection, might be a promising route for TB vaccination (22). PEG-b-PPS NBM are amenable to multiple routes of administration and have been previously optimized for pulmonary delivery of Ag85B subunit vaccines adjuvanted with CpG (22). By benchmarking our novel MA/Ag85B NBM formulations against BCG, we will contribute a missing component to current subunit vaccines. We will use the hCD1Tg mouse model to assess the protective efficacy of MA-Ag85B NBM as a prophylactic vaccine against virulent Mtb infection in two different settings: the first will assess their efficacy as a primary vaccine and the second will assess their efficacy as a BCG booster vaccine. Both hCD1Tg mice and their corresponding non-transgenic littermates will be immunized and challenged in parallel. This will verify that protection induced by MA-loaded NBM is group 1 CD1-dependent.

Figure 23:
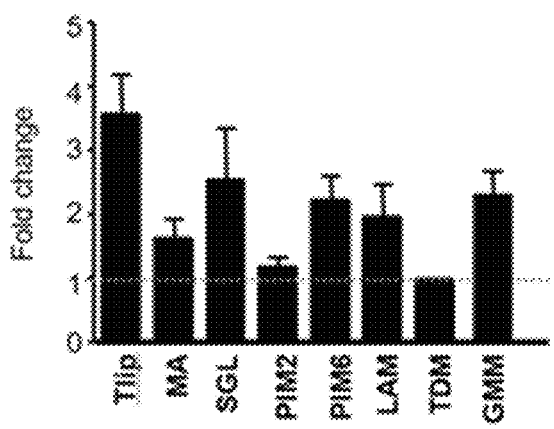
FIG. 23 shows immunodominance of known CD1b-restricted Mtb antigens in the Mtb-infected hCD1Tg mice.

Hundreds of distinct lipids can be extracted from Mtb, of which several dominant lipids in addition to MA may contribute to elicited CD1-restricted T cell responses during vaccination. For in vivo protective efficacy, we will therefore compare MA-loaded NBMs to NBMs loaded with MA along with two additional lipid antigens, GMM and SGL. These lipids are selected for the following reasons: i) T cell responses to GMM and SGL can be readily detected in Mtb-infected mice (FIG. 23) and Mtb-infected individuals (78-79), suggesting these Mtb lipids are immunogenic. ii) GMM, a MA-containing glycolipid, is produced by pathogenic mycobacteria with increased production during Mtb infection (80) and SGL is crucial for Mtb virulence (81). iii) Customized tetramers to identify CD1b-restricted T cells specific to these lipid antigens are available (FIG. 24) (82-84). iv). T cell lines for testing GMM and SGL NBMs are available.

MA/CD1b-specific DN1 T cells accumulate at sites of Mtb infection and contribute to protective immunity—To determine whether DN1 T cells were protective against Mtb infection, DN1 T cells were adoptively transferred to hCD1Tg/Rag$^{-/-}$ and Rag$^{-/-}$ mice, and recipient mice were subsequently challenged with virulent Mtb via the aerosol route. Four wks after infection, hCD1Tg/Rag$^{-/-}$ mice receiving DN1 T cells had significantly lower CFU in the lung and spleen compared with those that did not receive DN1 T cells (FIG. 25A). Moreover, adoptive transfer of DN1 T cells to Rag$^{-/-}$ (hCD1Tg$^-$) recipient mice did not significantly reduce bacterial burdens, suggesting that DN1 T cells confer protection against Mtb in an hCD1Tg-dependent manner (FIG. 25A). DN1 T cells isolated from infected hCD1Tg/Rag$^{-/-}$ recipients produced TNF-α, IFN-γ, and IL-2 and expressed CD107a, a surrogate marker of cytotoxic activity (data not shown). Substantial numbers of DN1 T cells were present in granuloma areas (FIG. 25B) of infected hCD1Tg/Rag$^{-/-}$ mice. These data demonstrate that DN1 T cells accumulate in lung granulomas and contributed to protective immunity against Mtb by producing inflammatory cytokines and exerting cytotoxicity.

Figures 26A, 26B, 26C, 26D:
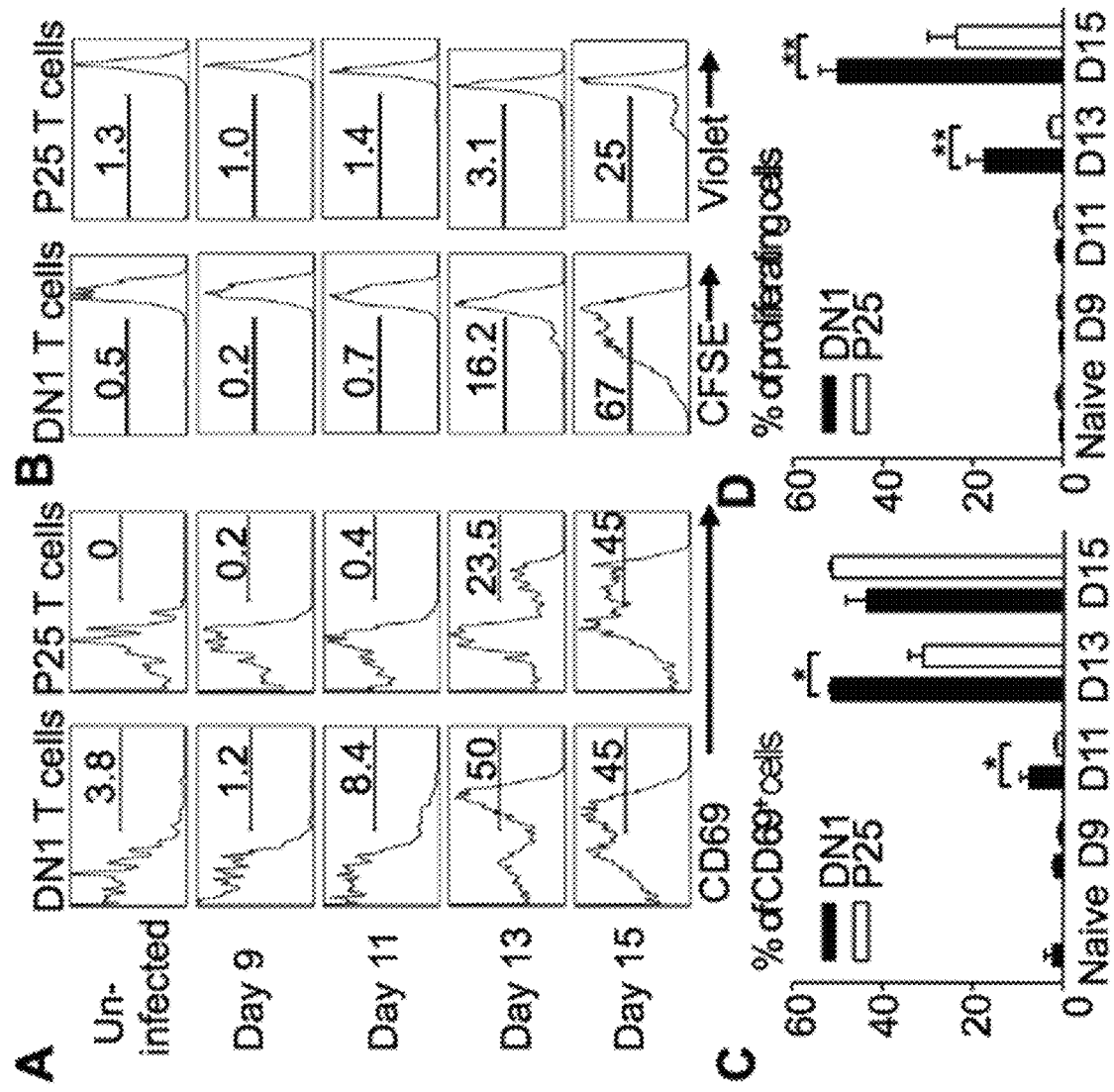

DN1 T cells are activated earlier after Mtb infection as compared to Ag85B-specific CD4$^+$ T cells—Myeloid DCs express both CD1b and MHC II. However, unlike MHC II, the trafficking of CD1b is unaffected by DC maturation. This leads to earlier antigen presentation by CD1b as compared to MHC II molecules in Mtb-infected DC (85). To see whether this translated to rapid priming of Mtb lipid-specific CD1b-restricted T cells in vivo, we compared the activation kinetics of DN1 T cells with P25 T cells during Mtb infection. CFSE-labeled DN1 T cells and CellTrace Violet—labeled P25 T cells were co-transferred to CD45.1 congenic hCD1Tg mice that had been infected 7 days prior. Up-regulation of CD69 on DN1 T cells began at day 11 post-infection while CD69 was up-regulated on a small percentage of P25 T cells 13 days post-infection (FIGS. 26A and 26C). Additionally, cell division was detected in DN1 T cells by day 13 compared to day 15 in P25 T cells (FIGS. 26B and 26D). This data suggests that activation of MA-specific CD1b-restricted T cells begins earlier than Ag85B-specific MHC II-restricted CD4$^+$ T cells during Mtb infection. The distinct kinetics of these two T cell populations may allow them to individually contribute to anti-mycobacterial activity at different time points during infection, providing enhanced protection.

To evaluate the protective efficacy of a combined protein and lipid antigen vaccination protocol against Mtb infection, we will immunize hCD1Tg mice and non-transgenic littermates with NBM formulations containing Ag85B combined with either MA alone or MA/GMM/SGL. The nanostructure/adjuvant formulation will utilize either BCN or PLGA. Un-immunized, BCG-immunized, and adjuvanted NBM (without antigens)-immunized mice will be used as controls, with additional groups immunized with NBM containing only MA or Ag 85B. We will assess the protective efficacy of adjuvanted MA-Ag85B NBM as a prophylactic vaccine against virulent Mtb infection as either a primary vaccine or a BCG booster vaccine. FIG. 27 depicts the treatment groups and analysis for each experiment in Mtb-infected mice. Briefly, 4 weeks after the last immunization, mice from different vaccination groups will be challenged with 100-150 CFU/mouse of aerosolized Mtb H37Rv, the fully virulent laboratory strain of Mtb, using an In-Tox nose-only aerosol exposure chamber in the BL3 facility. At 4 and 8 weeks post-infection, bacterial burdens in the spleen and lung will be determined. The protective efficacy of adjuvanted NBM immunization will be compared with that of subcutaneous BGC immunization (1×10$^6$ CFU, Pasteur strain). BCG-vaccinated animals typically show a 1 log reduction in colony counts in the lung (86). The frequency and function of MA-, GMM-, SGL- and Ag85B-specific T cells in the lung and spleen will be determined by ELISPOT and intracellular cytokine staining to see whether they correlate with the level of protection conferred by vaccination. The expression of CD127, KLRG1 (marker for T cell exhaustion), chemokine receptors for lung homing (e.g. CXCR3, CXCR5, CCR4 and CCR5), and co-inhibitory and co-stimulatory receptors (e.g. TIM-3, PD-1, CTLA-4, ICOS) on Ag85B$_{280-294}$/I-A$^b$ tetramer$^+$, MA/CD1b, GMM/CD1b, and SGL/CD1b tetramer$^+$ T cells will be determined. For comparison, the magnitude and quality of other Mtb-peptide specific T cell responses will also be determined using tetramers specific to TB10.4$_{4-11}$/K$^b$ and ESAT-6$_{4-17}$/I-A$^b$ (obtained from NIH tetramer facility). In addition, blood will be collected to assess MA-, GMM-, SGL- and Ag85B-specific IgG titers by ELISA. Hematoxylin and eosin staining of formalin-fixed lung tissues will determine differences in granuloma size and lung cellularity between groups.

We expect that adjuvanted MA-Ag85B NBM immunizations will induce robust MA- and Ag85B-specific T cell responses in hCD1Tg mice, which may provide superior protection against Mtb infection than immunization with NBM containing only MA or Ag85B. The combined MA/GMM/SGL formulation is expected to elicit significantly higher CD1b-restricted T cell response, as it contains a larger repertoire of lipid antigens. In addition, we expect that the use of adjuvanted MA-Ag85B or MA/GMM/SGL-Ag85B NBM as a booster vaccine for BCG could enhance the protective effect of BCG. Criteria for benchmarking against BCG include: reduced bacterial burdens, improved lung pathology, increased Mtb Ag-specific polyfunctional T cells (e.g. T cells with dual or triple cytokine producing capacity and cytotoxicity) and enriched lung resident memory T cells, which has been shown to offer rapid protection against Mtb infection (87). Additional immunogenic Mtb lipid antigens (e.g., dideoxymycobactin and mannosyl phosphomycoketide (88 and 89) for CD1a- and CD1c-restricted T cells, respectively) and protein antigens (e.g., ESAT-6 nad TB10.4) may also be incorporated into the nanoparticles.

While prolonged high-level antigen exposure often results in T cell exhaustion, slow sustained low-level stimulation by antigen/adjuvant depots can enhance memory T cell responses (90-93). BCG vaccination generates such depots for persistent antigen/adjuvant exposure, which sustains systemic cytokine production and promotes beneficial memory responses following early life immunization that unfortunately does not last beyond adolescence (37, 94, 95). The optimal kinetics for inducing CD1-restricted T cell response is currently unknown. We have developed a novel platform to control the release of MC from a s.c. injected filamentous hydrogel depot (FIGS. 28A-28C). Lipophilic payloads within the filomicelles comprising our FM-depots directly transfer to the released MC at the same loaded concentration (48). FM-depots may serve as a sustained delivery system for lipid antigens to assess the efficacy and toxicity of long-term, low-degree CD1-restricted T cell activation. We will engineer the MA-FM-depots to evaluate the quality and kinetics of CD1-restricted T cell response over the course of 6-10 weeks using the DN1Tg mouse model. Due to their unique development program and promiscuous nature of lipid antigen recognition, some human CD1-restricted T cells can be activated by both self-lipids and microbial lipids and have been linked to autoimmune responses (96) In fact, we have previously demonstrated that autoimmune dermatitis can be modeled in hCD1Tg/HJ1Tg mice (97) that have increased frequency of CD1b autoreactive T cells. We will use this model to assess any autoreactive responses following chronic exposure to lipid antigen delivery. Such responses by CD1-restricted T cells may contribute to a variety of unexplained atopic dermatitis (98). Due to the wide range of lipids present in Mtb, we will compare the safety of MC loaded with Mtb total lipid extracts versus the predominant lipid antigen MA alone.

FM-depots can sustainably release loaded MC for up to 10 weeks—We have shown that the rate of MC delivery from FM-depots can be controlled by the easily adjustable crosslinking density for up to 1 month (FIGS. 18A-18E) (48). To further investigate the attainable length of in vivo degradation for sustained MC delivery, FMs were loaded with near infrared fluorescence agent (NIRF) agent indocyanine green (ICG) and injected s.c. into mice (FIG. 28B). By adjusting the vinyl sulfone (VS) crosslinking density within FM-depots, these injections could achieve a remarkable 10 weeks of zero-order release of ICG-loaded MC with no detectable side-effects (FIG. 28C). These results verify that we can control the rate of MC release from ~4 days (1% mass/h) up to ~3 months (0.05% mass/h) in vivo in response to physiological levels of oxidation in s.c. tissue (no external stimulation required). This data validates that PEG-b-PPS FM-depots can achieve in vivo MA-MC delivery rates to mimic and expand upon BCG immunostimulation.

MA-loaded FM-depots can activate DN1 T cells in vivo—We sought to verify that FM-depots could be loaded with MA and stimulate DN1 T cells during low dosage sustained delivery following s.c. injection into mice. During self-assembly, MA was loaded into filomicelles composed of a 1:5 ratio of $PEG_{44}$-b-$PPS_{45}$/VS-$PEG_{44}$-b-$PPS_{45}$, which were crosslinked in situ at the site of injection using 8-arm PEG-thiol as previously described (48). This 20% crosslinking density was employed to obtain a 30 day release profile (48) of a 50 μg MA payload from 5 mg of polymer hydrogel. After 7 days of sustained release, DN1 T cells were adoptively transferred into immunized mice to assess the early stages of DN1 T cell activation. We found that this low level of sustained delivery of MA was sufficient to activate DN1 T cells in the draining lymph nodes, and, within the lung, the primary site of Mtb infection (FIGS. 29A-29B). These results demonstrate that MA-loaded FM depots can activate DN1 T cells and may serve as a simple, injectable, low dosage vaccine platform against TB besides being a means for assessing the effect of chronic CD1-restricted T cell activation.

Immunological characterization of MA-specific T cell activation by sustained release, MA-loaded FM-depots—MA-loaded FM-depots will be fabricated as previously described (48). FM-depot formulation will be crosslinked in situ following s.c. injection (50 μg MA in 5 mg PEG-b-PPS) into the scapular region of mice. The full range of release rates over the course of 10 wks will be tested by varying the incorporation of the crosslinkable block copolymer (VS-$PEG_{45}$-b-$PPS_{44}$) between 0%-20% w/w (FIGS. 18D and 28C) (48). As a control, 50 μg of MA will be divided into weekly bolus s.c. injections. DN1Tg T cells specifically respond to MA, similar to how OT1 T cells respond to SIINFEKL peptide antigen in standard vaccine models. However, unlike OT1 T cells, it is not feasible to track adoptively transferred DN1 T cells for 10 weeks, as they will be outcompeted by endogenous T cells (data not shown). We will therefore generate a mixed bone marrow (BM) chimera for these studies. To determine the activation and differentiation of DN1 T cells in response to sustained MA stimulation, we will generate mixed BM chimera using CD45.1 WT and DN1Tg/hCD1Tg/$Rag^{-/-}$ BM into hCD1Tg/$Rag^{-/-}$ recipients, which will then be immunized s.c. with MA-loaded FM-depots. Activation status (CD44, CD69, CD25 upregulation), proliferative capacity (Ki-76 expression), and memory T cell differentiation ($T_{EM-CD}44^{hi}CD62L^{lo}CCR7^-$, $T_{CM}$-$CD44^{hi}CD62L^{hi}CCR7^+$, $T_{RM}$-$CD69^+CD103^+CXCR3^+$) of DN1 T ($CD45.2^+$) the lung, lymph nodes and spleen of recipient mice will be determined by flow cytometric analysis at 2, 4, and 10 wks post-immunization. In additional, cytokine producing capacity of DN1 T cells in immunized mice will be examined by intracellular cytokine staining, including IFN-γ, TNF-α, IL-2, IL-17A, and GM-CSF. The presence of conventional T cells ($CD45.1^+$) derived from WT BM will allow us to determine whether immunization of MA-loaded FM-depot induces bystander activation of other T cells.

Determine if chronic activation of CD1-restricted T cells elicits autoreactive responses—To rigorously assess potential autoimmune responses resulting from chronic activation of CD1b-restricted T cells in mice injected with MA- or Mtb total lipids-loaded FM-depots, we will use TCR transgenic mouse model (HJ1Tg) that expressed a CD1b-autoreactive TCR (50) for this experiment. We have previously shown that HJ1 T cells isolated from HJ1Tg/hCD1Tg mice can produce proinflammatory cytokines in response to stimulation with CD1b-exprssing DC (50). Addition of Mtb lipids further enhances the cytokine secretion capacity of these T cells, suggesting HJ1 T cells exhibit dual reactivity, reminiscent of several human-derived CD1b-restricted T cell lines (96). Moreover, chronic activation of HJ1 T cells induces dermatitis in HJ1Tg/hCD1Tg mice (97). Thus, we will immunize HJ1Tg/hCD1Tg with MA- or Mtb total lipids-loaded FM-depots at our previously established effective dose (50 μg) and twice this dose (100 μg). The development of dermatitis will be monitored visually for 10 weeks. PBMC will be isolated weekly to monitor the activation status of HJ1 T cells by flow cytometry. At 10 wks postimmunization, mice will be sacked for multiplex cytokine analysis, skin histology, and T cell phenotype and local recruitment of various leukocytes will be determined by flow cytometry.

Anticipated results and interpretations—Since the protocols for synthesis of FM-depots have been established (48), we anticipate s.c. injected FM-depots to achieve multiple controllable release rates, including mimicry of BCG kinetics. Data using MA-MC administration along with our early stage (7 days of release) MA-loaded FM-depot data both demonstrate that MA-MC released by FM-depots can activate DN1 T cells in vivo. We anticipate that longer durations will continue and possibly strengthen this response, marked by elevated detection of proliferating IFN-γ-producing DN1 T cells. In addition, sustained MA exposure could have an effect on the memory generation of DN1 T cells. In terms of toxicity, low dosage sustained administration of MA is not expected to elicit strong autoreactive response. However, hydrogel containing Mtb total lipids may elicit local inflammatory response in HJ1Tg/hCD1Tg mice. We have already developed immunosuppressive PEG-b-PPS NBM loaded with rapamycin and NF-κB inhibitors (27, 99). Anti-inflammatory nanotherapeutics could locally suppress autoreactivity at the injection site while allowing the MA-MCs to release and controllably elicit responses remotely in the lymph nodes and lung.

It is possible that loaded MA may sufficiently modulate the surface tension of FM to influence long term release kinetics of FM-depots. If adjusting the MA concentration or crosslinking density of the FM-depots does not achieve the desired release kinetics, interfacial tension measurements will be performed via drop shape analysis (DSA) as we have previously performed to further optimize MA-loading and FM chemistry (surface charge, PEG and PPS end-functionalization, etc.) (48). Alternatively, MA-loaded MC can be synthesized separately and then entrapped within the crosslinked FM hydrogel network (FIG. 28A), allowing FM-depot degradation and NBM delivery without MA interference.

REFERENCES

1. Allen S D et al., Benchmarking Bicontinuous Nanospheres against Polymersomes for in Vivo Biodistribution and Dual Intracellular Delivery of Lipophilic and Water-Soluble Payloads. ACS Applied Materials & Interfaces. 2018; 10(40):33857-66
2. Shang S et al., Induction of *Mycobacterium Tuberculosis* Lipid-Specific T Cell Responses by Pulmonary Delivery of Mycolic Acid-Loaded Polymeric Micellar Nanocarriers. Frontiers in Immunology. 2018; 9(2709).
3. Siddiqui S, et al., Role of Group 1 CD1-Restricted T Cells in Infectious Disease. Front Immunol. 2015; 6:337. Epub 2015/07/16.
4. Chancellor A, et al., The versatility of the CD1 lipid antigen presentation pathway. Immunology. 2018; 154(2): 196-203. Epub 2018/02/21.
5. Organization W H. Global tuberculosis report 2018. World Health Organization. whoint/iris/handle/10665/274453.
6. Scott E A, et al., Overcoming Immune Dysregulation with Immunoengineered Nanobiomaterials. Annu Rev Biomed Eng. 2017; 19:57-84
7. Rodrigues L C, et al., Protective effect of BCG against tuberculous meningitis and miliary tuberculosis: a meta-analysis. Int J Epidemiol. 1993; 22(6):1154-8. Epub 1993/12/01. PubMed PMID: 8144299.
8. Shann F. Editorial Commentary: Different Strains of Bacillus Calmette-Guerin Vaccine Have Very Different Effects on Tuberculosis and on Unrelated Infections. Clin Infect Dis. 2015; 61(6):960-2. Epub 2015/06/11.
9. Davenne T, et al., Why don't we have an effective tuberculosis vaccine yet? Expert Rev Vaccines. 2016; 15(8):1009-13.
10. Kaufmann S H, et al., Novel approaches to tuberculosis vaccine development. Int J Infect Dis. 2017; 56:263-7.
11. Tameris M D, et al., Safety and efficacy of MVA85A, a new tuberculosis vaccine, in infants previously vaccinated with BCG: a randomised, placebo-controlled phase 2b trial. Lancet. 2013; 381(9871):1021-8.
12. Tameris M et al., Lessons learnt from the first efficacy trial of a new infant tuberculosis vaccine since BCG. Tuberculosis. 2013; 93(2):143-9.
13. Tameris M et al., A double-blind, randomised, placebo-controlled, dose-finding trial of the novel tuberculosis vaccine AERAS-402, an adenovirus-vectored fusion protein, in healthy, BCG-vaccinated infants. Vaccine. 2015; 33(25):2944-54.
14. De Libero G, et al., The T-Cell Response to Lipid Antigens of *Mycobacterium tuberculosis*. Front Immunol. 2014; 5:219.
15. Gold M C, et al., Human mucosal associated invariant T cells detect bacterially infected cells. PLoS Biol. 2010; 8(6):e1000407. Epub 2010 Jul. 9.
16. Van Rhijn I et al., CD1a, CD1b, and CD1c in immunity against mycobacteria. Advances in experimental medicine and biology. 2013; 783:181-97.

17. Barry C E, 3rd, et al., Mycolic acids: structure, biosynthesis and physiological functions. Prog Lipid Res. 1998; 37(2-3):143-79. PubMed PMID: 9829124.
18. Van Rhijn I, et al., CD1 and mycobacterial lipids activate human T cells. Immunological reviews. 2015; 264(1): 138-53.
19. Montamat-Sicotte D J, et al., A mycolic acid-specific CD1-restricted T cell population contributes to acute and memory immune responses in human tuberculosis infection. J Clin Invest. 2011; 121(6):2493-503.
20. Salio M, et al., Biology of CD1- and MR1-restricted T cells. Annual review of immunology. 2014; 32:323-66.
21. Aagaard C, et al., Protection and polyfunctional T cells induced by Ag85B-TB10.4/IC31 against *Mycobacterium tuberculosis* is highly dependent on the antigen dose. PloS one. 2009; 4(6):e5930.
22. Ballester M, et al., Nanoparticle conjugation and pulmonary delivery enhance the protective efficacy of Ag85B and CpG against tuberculosis. Vaccine. 2011; 29(40): 6959-66.
23. de Jong A. Activation of human T cells by CD1 and self-lipids. Immunol Rev. 2015; 267(1):16-29. Epub 2015 Aug. 19.
24. Li S et al., Autoreactive CD1b-restricted T cells: a new innate-like T-cell population that contributes to immunity against infection. Blood. 2011; 118(14):3870-8. Epub 2011 Aug. 24.
25. Salio M, et al., Modulation of human natural killer T cell ligands on TLR-mediated antigen-presenting cell activation. Proc Natl Acad Sci U.S.A. 2007; 104(51):20490-5. Epub 2007 Dec. 14.
26. Bagchi S, et al., CD1b-autoreactive T cells recognize phospholipid antigens and contribute to antitumor immunity against a CD1b(+) T cell lymphoma. Oncoimmunology. 2016; 5(9):e1213932. Epub 2016 Oct. 21.
27. Allen S, et al., Facile assembly and loading of theranostic polymersomes via multi-impingement flash nanoprecipitation. J Control Release. 2017; 262:91-103. Epub 2017 Jul. 25.
28. Dowling D J, et al., Toll-like receptor 8 agonist nanoparticles mimic immunomodulating effects of the live BCG vaccine and enhance neonatal innate and adaptive immune responses. J Allergy Clin Immunol. 2017; 140 (5):1339-50. Epub 2017 Mar. 28.
29. Scott E A, et al., Dendritic cell activation and T cell priming with adjuvant- and antigen-loaded oxidation-sensitive polymersomes. Biomaterials. 2012; 33(26): 6211-9.
30. Billeskov R, et al., High Antigen Dose Is Detrimental to Post-Exposure Vaccine Protection against Tuberculosis. Front Immunol. 2017; 8:1973. Epub 2018 Jan. 31.
31. Du F, et al., Sequential intracellular release of water-soluble cargos from Shell-crosslinked polymersomes. J Control Release. 2018. Epub 2018 Mar. 31.
32. Han J, et al., A simple confined impingement jets mixer for flash nanoprecipitation. J Pharm Sci. 2012; 101(10): 4018-23.
33. Bobbala S, et al., Flash nanoprecipitation permits versatile assembly and loading of polymeric bicontinuous cubic nanospheres. Nanoscale. 2018; 10(11):5078-88. Epub 2017 Dec. 20.
34. Stano A, et al., Tunable T cell immunity towards a protein antigen using polymersomes vs. solid-core nanoparticles. Biomaterials. 2013; 34(17):4339-46.
35. Vasdekis A E, et al., Precision intracellular delivery based on optofluidic polymersome rupture. ACS nano. 2012; 6(9):7850-7.
36. Napoli A, et al., Oxidation-responsive polymeric vesicles. Nature Materials. 2004; 3:183.
37. Olsen A W, et al., The influence of remaining live BCG organisms in vaccinated mice on the maintenance of immunity to tuberculosis. Scand J Immunol. 2004; 60(3): 273-7. Epub 2004 Aug. 24.
38. Yi S, et al., Tailoring Nanostructure Morphology for Enhanced Targeting of Dendritic Cells in Atherosclerosis. ACS Nano. 2016; 10(12):11290-303.
39. Yi S, et al., Tailoring Nanostructure Morphology for Enhanced Targeting of Dendritic Cells in Atherosclerosis. ACS nano. 2016; 10(12):11290-303.
40. Napoli A, et al., Glucose-oxidase based self-destructing polymeric vesicles. Langmuir. 2004; 20(9):3487-91.
41. Discher B M, et al., Polymersomes: tough vesicles made from diblock copolymers. Science. 1999; 284(5417): 1143-6. Epub 1999 May 15. PubMed PMID: 10325219.
42. Christian D A, et al., Polymersome carriers: from self-assembly to siRNA and protein therapeutics. Eur J Pharm Biopharm. 2009; 71(3):463-74. Epub 2008 Nov. 4.
43. Onaca O, et al., Stimuli-responsive polymersomes as nanocarriers for drug and gene delivery. Macromol Biosci. 2009; 9(2):129-39. Epub 2008 Dec. 25.
44. Allen S D, et al., On the advancement of polymeric bicontinuous nanospheres toward biomedical applications. Nanoscale Horizons. 2019.
45. Vasdekis A E, et al., Precision intracellular delivery based on optofluidic polymersome rupture. ACS nano. 2012; 6(9):7850-7.
46. Dowling D J, et al., Toll-like receptor 8 agonist nanoparticles mimic immunomodulating effects of the live BCG vaccine and enhance neonatal innate and adaptive immune responses. J Allergy Clin Immunol. 2017.
47. Sugita M, et al., Pathways of CD1 and lipid antigen delivery, trafficking, processing, loading, and presentation. Curr Top Microbiol Immunol. 2007; 314:143-64. Epub 2007 Jun. 28. PubMed PMID: 17593660.
48. Karabin N B, et al., Sustained micellar delivery via inducible transitions in nanostructure morphology. Nat Commun. 2018; 9(1):624. Epub 2018 Feb. 13.
49. Felio K, et al., CD1-restricted adaptive immune responses to Mycobacteria in human group 1 CD1 transgenic mice. The Journal of experimental medicine. 2009; 206(11):2497-509.
50. Li S, et al., Autoreactive CD1b-restricted T cells: a new innate-like T-cell population that contributes to immunity against infection. Blood. 2011; 118(14):3870-8.
51. Beckman E M, et al., Recognition of a lipid antigen by CD1-restricted alpha beta+ T cells. Nature. 1994; 372 (6507):691-4.
52. Zhao J, et al., Mycolic acid-specific T cells protect against *Mycobacterium tuberculosis* infection in a humanized transgenic mouse model. Elife. 2015; 4.
53. de Lalla C, et al., High-frequency and adaptive-like dynamics of human CD1 self-reactive T cells. Eur J Immunol. 2011; 41(3):602-10. Epub 2011 Jan. 20.
54. de Jong A, et al., CD1a-autoreactive T cells are a normal component of the human alphabeta T cell repertoire. Nat Immunol. 2010; 11(12):1102-9. Epub 2010 Nov. 3.
55. Yoshida M, et al., Effect of poly(lactic-co-glycolic acid) contact on maturation of murine bone marrow-derived dendritic cells. J Biomed Mater Res A. 2007; 80(1):7-12. Epub 2006 Sep. 8.
56. Prasad S, et al., Tolerogenic Ag-PLG nanoparticles induce tregs to suppress activated diabetogenic CD4 and CD8 T cells. J Autoimmun. 2018; 89:112-24. Epub 2017 Dec. 21.

57. Allen R P, et al., Latent, Immunosuppressive Nature of Poly(lactic-co-glycolic acid) Microparticles. ACS Biomaterials Science & Engineering. 2018; 4(3):900-18.
58. Dascher C C, et al., Immunization with a mycobacterial lipid vaccine improves pulmonary pathology in the guinea pig model of tuberculosis. International immunology. 2003; 15(8):915-25. PubMed PMID: 12882829.
59. Van Rhijn I et al., The bovine CD1 family contains group 1 CD1 proteins, but no functional CD1d. Journal of immunology. 2006; 176(8):4888-93. PubMed PMID: 16585584.
60. Pais V F, et al., OFF-ON-OFF fluorescence switch with T-latch function. Org Lett. 2011; 13(20):5572-5.
61. Aguilo N, et al., Pulmonary but Not Subcutaneous Delivery of BCG Vaccine Confers Protection to Tuberculosis-Susceptible Mice by an Interleukin 17-Dependent Mechanism. J Infect Dis. 2016; 213(5):831-9.
62. Perdomo C, et al., Mucosal BCG Vaccination Induces Protective Lung-Resident Memory T Cell Populations against Tuberculosis. Mbio. 2016; 7(6).
63. Yoshida M et al., Poly(lactic-co-glycolic acid) enhances maturation of human monocyte-derived dendritic cells. J Biomed Mater Res A. 2004; 71(1):45-54. Epub 2004 Sep. 16.
64. Silva J M, et al., Immune system targeting by biodegradable nanoparticles for cancer vaccines. J Control Release. 2013; 168(2):179-99. Epub 2013 Mar. 26.
65. Bobbala S, et al., Novel Injectable Pentablock Copolymer Based Thermoresponsive Hydrogels for Sustained Release Vaccines. AAPS J. 2016; 18(1):261-9. Epub 2015 Nov. 22.
66. Bobbala S, et al., Poloxamer 407-chitosan grafted thermoresponsive hydrogels achieve synchronous and sustained release of antigen and adjuvant from single-shot vaccines. Immunology & Cell Biology. 2018; 96(6):656-65.
67. Panyam J, et al., Rapid endo-lysosomal escape of poly(DL-lactide-co-glycolide) nanoparticles: implications for drug and gene delivery. FASEB J. 2002; 16(10): 1217-26. Epub 2002 Aug. 3.
68. Allen S D, et al., Polymersomes scalably fabricated via flash nanoprecipitation are non-toxic in non-human primates and associate with leukocytes in the spleen and kidney following intravenous administration. Nano Research. 2018.
69. Blaauboer S M, et al., The mucosal adjuvant cyclic di-GMP enhances antigen uptake and selectively activates pinocytosis-efficient cells in vivo. Elife. 2015; 4.
70. Byrne M L, et al., Self-reported parenting style is associated with children's inflammation and immune activation. J Fam Psychol. 2017; 31(3):374-80.
71. Nikitczuk K P, et al., PLGA-polymer encapsulating tumor antigen and CpG DNA administered into the tumor microenvironment elicits a systemic antigen-specific IFN-gamma response and enhances survival. J Cancer Ther. 2013; 4(1):280-90. Epub 2013 Jun. 7.
72. Allahyari M, et al., Peptide/protein vaccine delivery system based on PLGA particles. Hum Vaccin Immunother. 2016; 12(3):806-28. Epub 2015 Oct. 30.
73. Stack T, et al., Modulation of Schlemm's canal endothelial cell stiffness via latrunculin loaded block copolymer micelles. J Biomed Mater Res A. 2018; 106(7):1771-9. Epub 2018 Feb. 23.
74. Wolf A J, et al., Initiation of the adaptive immune response to *Mycobacterium tuberculosis* depends on antigen production in the local lymph node, not the lungs. The Journal of experimental medicine. 2008; 205(1):105-15. Epub 2007 Dec. 26.
75. Du F, et al., Immunotheranostic Polymersomes Modularly Assembled from Tetrablock and Diblock Copolymers with Oxidation-Responsive Fluorescence. Cel Mol Bioeng. 2017.
76. Achkar J M, et al., B cells and antibodies in the defense against *Mycobacterium tuberculosis* infection. Immunol Rev. 2015; 264(1):167-81. Epub 2015 Feb. 24.
77. Du F F, et al., Immunotheranostic Polymersomes Modularly Assembled from Tetrablock and Diblock Copolymers with Oxidation-Responsive Fluorescence. Cell Mol Bioeng. 2017; 10(5):357-70.
78. Moody D B, et al., Structural requirements for glycolipid antigen recognition by CD1b-restricted T cells. Science. 1997; 278(5336):283-6. Epub 1997 Oct. 10. PubMed PMID: 9323206.
79. Gilleron M, et al., Diacylated sulfoglycolipids are novel mycobacterial antigens stimulating CD1-restricted T cells during infection with *Mycobacterium tuberculosis*. The Journal of experimental medicine. 2004; 199(5):649-59. Epub 2004 Feb. 26.
80. Matsunaga I, et al., Mycolyltransferase-mediated glycolipid exchange in Mycobacteria. J Biol Chem. 2008; 283(43):28835-41. Epub 2008 Aug. 16.
81. Goren M B, et al., Lipids of putative relevance to virulence in *Mycobacterium tuberculosis*: correlation of virulence with elaboration of sulfatides and strongly acidic lipids. Infect Immun. 1974; 9(1):142-9. Epub 1974 Jan. 1. PubMed PMID: 4202886; PMCID: PMC414778.
82. Kasmar A G, et al., CD1b tetramers bind alphabeta T cell receptors to identify a mycobacterial glycolipid-reactive T cell repertoire in humans. The Journal of experimental medicine. 2011; 208(9):1741-7. Epub 2011 Aug. 3.
83. Layton E D, et al., Validation of a CD1b tetramer assay for studies of human mycobacterial infection or vaccination. J Immunol Methods. 2018; 458:44-52. Epub 2018 Apr. 24.
84. James C A, et al., CD1b Tetramers Identify T Cells that Recognize Natural and Synthetic Diacylated Sulfoglycolipids from *Mycobacterium tuberculosis*. Cell Chem Biol. 2018; 25(4):392-402 e14. Epub 2018 Feb. 6.
85. Hava D L, et al., Evasion of peptide, but not lipid antigen presentation, through pathogen-induced dendritic cell maturation. Proc Natl Acad Sci USA. 2008; 105(32): 11281-6. Epub 2008 Aug. 8.
86. Goter-Robinson C, et al., Protection against an aerogenic *Mycobacterium tuberculosis* infection in BCG-immunized and DNA-vaccinated mice is associated with early type I cytokine responses. Vaccine. 2006; 24(17):3522-9.
87. Sakai S, et al., Defining features of protective CD4 T cell responses to *Mycobacterium tuberculosis*. Curr Opin Immunol. 2014; 29:137-42. Epub 2014 Jul. 8.
88. Ly D, et al., CD1c tetramers detect ex vivo T cell responses to processed phosphomycoketide antigens. The Journal of experimental medicine. 2013; 210(4):729-41.
89. Moody D B, et al., CD1c-mediated T-cell recognition of isoprenoid glycolipids in *Mycobacterium tuberculosis* infection. Nature. 2000; 404(6780):884-8.
90. Rosenkrands I, et al., Cationic liposomes containing mycobacterial lipids: a new powerful Th1 adjuvant system. Infect Immun. 2005; 73(9):5817-26. Epub 2005 Aug. 23.
91. Lindenstrom T, et al., Tuberculosis subunit vaccination provides long-term protective immunity characterized by 92. Jelley-Gibbs D M, et al., Unexpected prolonged presentation of influenza antigens promotes CD4 T cell memory generation. J Exp Med. 2005; 202(5):697-706. Epub 2005 Sep. 9.
93. Duffy D, et al., Immunological memory transferred with CD4 T cells specific for tuberculosis antigens Ag85B-TB10.4: persisting antigen enhances protection. PLoS One. 2009; 4(12):e8272. Epub 2009 Dec. 17.
94. Beveridge N E, et al., Immunisation with BCG and recombinant MVA85A induces long-lasting, polyfunctional *Mycobacterium tuberculosis*-specific CD4+ memory T lymphocyte populations. Eur J Immunol. 2007; 37(11):3089-100. Epub 2007 Nov. 20.
95. Toyohara M, et al., Studies on the effect of isoniazid upon the antituberculous immunity induced by BCG vaccination. Tubercle. 1959; 40:184-91. Epub 1959 Jun. 1. PubMed PMID: 13839107.
96. Vincent M S, et al., CD1a-, b-, and c-restricted TCRs recognize both self and foreign antigens. Journal of Immunology. 2005; 175(10):6344-51.
97. Bagchi S, et al., CD1b-autoreactive T cells contribute to hyperlipidemia-induced skin inflammation in mice. The Journal of clinical investigation. 2017; 127(6):2339-52. Epub 2017 May 4.
98. Betts R J, et al., Contact sensitizers trigger human CD1-autoreactive T-cell responses. Eur J Immunol. 2017; 47(7):1171-80. Epub 2017 Apr. 26.
99. Yi S, Zhang X, et al., Targeted immunomodulation of dendritic cells via surface engineered polymersomes inhibits atherosclerosis. Nat Commun. In Revision.
100. Consonni M, et al., Potential advantages of CD1-restricted T cell immunotherapy in cancer. Mol Immunol. 2018; 103:200-8. Epub 2018 Oct. 12.
101. Lepore M, et al., Targeting leukemia by CD1c-restricted T cells specific for a novel lipid antigen. Oncoimmunology. 2015; 4(3):e970463. Epub 2015 May 8.
102. Terabe M, et al., Tissue-Specific Roles of NKT Cells in Tumor Immunity. Front Immunol. 2018; 9:1838. Epub 2018 Aug. 31.
103. Wolf B J, et al., Novel Approaches to Exploiting Invariant NKT Cells in Cancer Immunotherapy. Front Immunol. 2018; 9:384. Epub 2018 Mar. 22.

Example 3

In the following experiments we have verified that mycolic acid (MA) loaded bicontinuous nanospheres (BCN) can activate group 1 CD1-restricted T cells both in vitro (FIG. 31) and in vivo (FIGS. 32A-32B). Furthermore, we verified that BCN could also serve as a platform to activate MHC-restricted T cell responses in vivo.

We used CD1b-restricted MA-specific DN1 T cells to compare the potency of MA BCN and standard poly(lactic-co-glycolic acid) (PLGA) nanoparticles in vitro. Briefly, bone marrow derived dendric cells (bmDCs) were pulsed with various concentrations of the nanoparticles and co-cultured with DN1 T cells. The activation of DN1 T cells was assessed by measuring the expression of CD69 and CD25 receptors using flow cytometry. In FIG. 31 we report the percent CD25+CD69+ DN1 T cells in each of the enumerated conditions. We found that MA BCN and MA PLGA can both activate DN1 T cells just as well or better than free MA. While blank BCN has little to no ability to activate DN1 T cells, blank PLGA can non-specifically activate DN1 T cells at higher concentrations. This work confirmed a background immunogenicity of PLGA that may contribute to its extensive stimulation of DN1 T cells. This lack of control over this stimulation make PLGA less suitable for drug and vaccine development using MA. In contrast, MA BCN displayed an excellent dose-response amenable to therapeutic optimization.

We then investigated whether MA-BCN could activate DN1 T cells in vivo by vaccinating hCD1Tg mice with MA-BCN, MA PLGA, blank BCN, and blank PLGA and subsequently adoptively transferring DN1 T cells (FIGS. 32A-32B). We found that MA BCN was superior at increasing CD44 expression and proliferation compared to MA PLGA. Overall, we found that our lipid carrying BCN were the only formulation capable of extensively activating group 1 CD1-restricted T cells in mice.

We also sought to determine whether BCN loaded with protein antigen could activate peptide-specific T cells. We found that BCN loaded with *Mycobacterium tuberculosis* protein Ag85B (Ag85B-BCN) could stimulate p25-specific T cells with equal efficacy as free form protein in an in vitro co-culture titration (FIG. 33A). For in vivo validation, we then assessed increases in Ag85B-specific IFN-γ production by T cells through ELISPOT assay after intranasal vaccination with Ag85B BCN or blank BCN (FIG. 33B). Indeed, we found that in the draining lymph nodes (DLN), there was a significant increase in Ag85B-specific spots in the vaccinated conditions.

Thus, we have established both protein and lipid specific vaccination approaches using BCN nanocarriers, which together can be used to activate both MHC- and CD-1 restricted T cells.

The invention claimed is:

1. A subunit vaccine composition comprising a nanocarrier;
   wherein the nanocarrier is loaded with one or more peptide antigens and one or more lipid antigens;
   wherein the nanocarrier is a bicontinuous nanosphere or a filomicelle; and
   wherein the subunit vaccine elicits a CD1 T cell response against the lipid antigen.

2. The subunit vaccine of claim 1, wherein the lipid antigen is selected from the group consisting of mycolic acid (MA), dieoxymycobactin, mannosyl phosphomycoketide, *Mycobacterium tuberculosis* (Mtb) total lipid extract (Tlip), sulfoglycolipid (SGL), phosphatidyl mannoside 2 (PIM2), phosphotidyl mannoside 6 (PIM6), lipoarabinomannan (LAM), trehalose dimycolate (TDM), glucose monomycolate (GMM).

3. The subunit vaccine of claim 1, wherein the peptide antigen is specific to Mtb.

4. The subunit vaccine of claim 3, wherein the peptide antigen is selected from the group consisting of *Mycobacterium Tuberculosis* major secretory protein antigen 85A (Ag85A), Antigen 85B (Ag85B), Mtb early secretory antigenic target 6 (ESAT-6), and Low Molecular Weight Protein Antigen 7 EsxH (Protein TB10.4).

5. The subunit vaccine of claim 1, wherein the nanocarrier comprises poly(ethylene glycol)-bl-poly(propylene sulfide) (PEG-bl-PPS) or poly(lactic-co-glycolic acid) (PLGA).

6. The subunit vaccine of claim 1, wherein the nanocarrier is a filomicelle.

7. The subunit vaccine of claim 6, wherein the filomicelle comprises vinyl sulfone modified PEG-bl-PPS (VS-PEG-bl-PPS).

8. The subunit vaccine of claim 7, wherein the filomicelle is crosslinked to form a hydrogel.

9. The subunit vaccine of claim 8, wherein the VS-PEG-bl-PPS is crosslinked with thiol modified poly(ethylene glycol).

10. A hydrogel depot comprising the subunit vaccine of claim 9.

11. A composition comprising the subunit vaccine of claim 1 and a pharmaceutically acceptable carrier.

12. A composition comprising the hydrogel of claim 8 and a pharmaceutically acceptable carrier.

13. The composition of claim 11, additionally comprising an adjuvant.

* * * * *